US011172997B2

(12) United States Patent
Kostrzewski et al.

(10) Patent No.: US 11,172,997 B2
(45) Date of Patent: Nov. 16, 2021

(54) APPARATUS AND SYSTEMS FOR PRECISE GUIDANCE OF SURGICAL TOOLS

(71) Applicant: KB Medical SA, Lausanne (CH)

(72) Inventors: Szymon Kostrzewski, Lausanne (CH);
Olivier Chappuis, Lausanne (CH);
Billy Nussbaumer, Preverenges (CH);
Daniel Gehriger, Lausanne (CH);
Roderik Berthelin, La Chapelle Rambaud (FR)

(73) Assignee: KB Medical, SA, Audubon, PA (US)

( * ) Notice: Subject to any disclaimer, the term of this patent is extended or adjusted under 35 U.S.C. 154(b) by 0 days.

(21) Appl. No.: 14/947,674

(22) Filed: Nov. 20, 2015

(65) Prior Publication Data
US 2016/0081754 A1 Mar. 24, 2016

Related U.S. Application Data

(63) Continuation of application No. 14/266,769, filed on Apr. 30, 2014, now Pat. No. 9,283,048.
(Continued)

(51) Int. Cl.
*A61B 34/30* (2016.01)
*A61B 90/11* (2016.01)
(Continued)

(52) U.S. Cl.
CPC .............. *A61B 34/30* (2016.02); *A61B 34/20* (2016.02); *A61B 34/70* (2016.02); *A61B 90/06* (2016.02);
(Continued)

(58) Field of Classification Search
CPC ........ A61B 19/2203; A61B 2019/2211; A61B 2019/2215; A61B 2019/2219;
(Continued)

(56) References Cited

U.S. PATENT DOCUMENTS 4,150,293 A 4/1979 Franke
4,166,602 A 9/1979 Nilsen et al.
(Continued)

FOREIGN PATENT DOCUMENTS

DE 10003051 A1 8/2001
EP 1355765 10/2003
(Continued)

OTHER PUBLICATIONS

Rosa Is a New Stereotactic Neurological Surgery Robot, Neurological Surgery, Jun. 13, 2011 (http://www.medgadget.com/2011/06/rosa-neuro-surgery-robot.html).
(Continued)

*Primary Examiner* — Alexander J Orkin

(57) ABSTRACT

Described herein are systems, apparatus, and methods for precise placement and guidance of tools during a surgical procedure, particularly a spinal surgical procedure. The system features a portable robot arm with an end effector for precise positioning of a surgical tool. The system requires only minimal training by surgeons/operators, is intuitive to use, and has a small footprint with significantly reduced obstruction of the operating table. The system works with existing, standard surgical tools, does not require increased surgical time or preparatory time, and safely provides the enhanced precision achievable by robot-assisted systems.

26 Claims, 29 Drawing Sheets

Related U.S. Application Data

(60) Provisional application No. 61/887,273, filed on Oct. 4, 2013.

(51) Int. Cl.
  *A61B 34/00* (2016.01)
  *A61B 90/00* (2016.01)
  *A61B 34/20* (2016.01)
  *A61B 34/10* (2016.01)

(52) U.S. Cl.
  CPC .............. *A61B 90/11* (2016.02); *A61B 34/10* (2016.02); *A61B 90/37* (2016.02); *A61B 2034/107* (2016.02); *A61B 2034/2055* (2016.02); *A61B 2090/066* (2016.02); *A61B 2090/376* (2016.02); *A61B 2090/3762* (2016.02)

(58) Field of Classification Search
  CPC ...... A61B 2019/2223; A61B 2019/223; A61B 6/4458; A61B 34/30; A61B 34/32; A61B 34/35; A61B 34/37; A61B 2034/301–306; B25J 9/00
  See application file for complete search history.

(56) References Cited

U.S. PATENT DOCUMENTS

| | | | |
|---|---|---|---|
| 4,799,779 A | | 1/1989 | Mesmer |
| 5,246,010 A | | 9/1993 | Gazzara et al. |
| 5,343,385 A | * | 8/1994 | Joskowicz ............ B25J 9/1664 700/255 |
| 5,408,409 A | | 4/1995 | Glassman et al. |
| 5,427,097 A | * | 6/1995 | Depp .................... A61N 5/1049 600/427 |
| 5,436,542 A | * | 7/1995 | Petelin ................... B25J 9/1679 318/567 |
| 5,598,453 A | | 1/1997 | Baba et al. |
| 5,772,594 A | | 6/1998 | Barrick |
| 5,948,002 A | | 9/1999 | Bonutti |
| 5,987,960 A | | 11/1999 | Messner et al. |
| 6,031,888 A | | 2/2000 | Ivan et al. |
| 6,144,875 A | | 11/2000 | Schweikard et al. |
| D435,107 S | | 12/2000 | Blair et al. |
| 6,203,196 B1 | | 3/2001 | Meyer et al. |
| 6,306,126 B1 | | 10/2001 | Montezuma |
| 6,314,311 B1 | | 11/2001 | Williams et al. |
| 6,320,929 B1 | | 11/2001 | Von Der Haar |
| D456,080 S | | 4/2002 | Karlsson |
| D461,484 S | | 8/2002 | Kraft |
| 6,451,027 B1 | | 9/2002 | Cooper et al. |
| 6,477,400 B1 | | 11/2002 | Barrick |
| 6,484,049 B1 | | 11/2002 | Seeley et al. |
| 6,487,267 B1 | | 11/2002 | Wolter |
| 6,490,475 B1 | | 12/2002 | Seeley et al. |
| 6,501,981 B1 | | 12/2002 | Schweikard et al. |
| 6,535,756 B1 | | 3/2003 | Simon et al. |
| 6,604,021 B2 | | 8/2003 | Imai et al. |
| 6,614,453 B1 | | 9/2003 | Suri et al. |
| 6,614,871 B1 | | 9/2003 | Kobiki et al. |
| 6,619,840 B2 | | 9/2003 | Rasche et al. |
| 6,666,579 B2 | | 12/2003 | Jensen |
| 6,723,106 B1 | * | 4/2004 | Charles .................. B25J 9/1065 606/130 |
| 6,757,068 B2 | | 6/2004 | Foxlin |
| 6,782,287 B2 | | 8/2004 | Grzeszczuk et al. |
| 6,856,826 B2 | | 2/2005 | Seeley et al. |
| 6,856,827 B2 | | 2/2005 | Seeley et al. |
| D506,257 S | | 6/2005 | Smith |
| 6,920,347 B2 | | 7/2005 | Simon et al. |
| 6,922,632 B2 | | 7/2005 | Foxlin |
| 6,988,009 B2 | | 1/2006 | Grimm et al. |
| 6,996,487 B2 | | 2/2006 | Jutras et al. |
| 7,016,457 B1 | | 3/2006 | Senzig et al. |
| 7,043,961 B2 | | 5/2006 | Pandey et al. |
| 7,062,006 B1 | | 6/2006 | Pelc et al. |
| 7,063,705 B2 | | 6/2006 | Young et al. |
| 7,072,707 B2 | | 7/2006 | Galloway, Jr. et al. |
| 7,099,428 B2 | | 8/2006 | Clinthorne et al. |
| D528,216 S | | 9/2006 | Korner |
| 7,108,421 B2 | | 9/2006 | Gregerson et al. |
| 7,130,676 B2 | | 10/2006 | Barrick |
| 7,139,418 B2 | | 11/2006 | Abovitz et al. |
| 7,155,316 B2 | | 12/2006 | Sutherland et al. |
| 7,194,120 B2 | | 3/2007 | Wicker et al. |
| 7,196,454 B2 | | 3/2007 | Baur et al. |
| 7,197,107 B2 | | 3/2007 | Arai et al. |
| 7,231,014 B2 | | 6/2007 | Levy |
| 7,231,063 B2 | | 6/2007 | Naimark et al. |
| D548,759 S | | 8/2007 | Kraft |
| D553,655 S | | 10/2007 | Jennings et al. |
| 7,301,648 B2 | | 11/2007 | Foxlin |
| 7,313,430 B2 | | 12/2007 | Urquhart et al. |
| 7,318,805 B2 | | 1/2008 | Schweikard et al. |
| 7,324,623 B2 | | 1/2008 | Heuscher et al. |
| 7,327,865 B2 | | 2/2008 | Fu et al. |
| D572,739 S | | 7/2008 | Jennings et al. |
| 7,460,637 B2 | | 12/2008 | Clinthorne et al. |
| 7,493,153 B2 | | 2/2009 | Ahmed et al. |
| 7,505,617 B2 | | 3/2009 | Fu et al. |
| 7,623,902 B2 | | 11/2009 | Pacheco |
| 7,643,862 B2 | | 1/2010 | Schoenefeld |
| 7,661,881 B2 | | 2/2010 | Gregerson et al. |
| 7,683,331 B2 | | 3/2010 | Chang |
| 7,683,332 B2 | | 3/2010 | Chang |
| 7,702,379 B2 | | 4/2010 | Avinash et al. |
| 7,702,477 B2 | | 4/2010 | Tuemmler et al. |
| 7,711,083 B2 | | 5/2010 | Heigl et al. |
| 7,725,253 B2 | | 5/2010 | Foxlin |
| 7,726,171 B2 | | 6/2010 | Langlotz et al. |
| 7,760,849 B2 | | 7/2010 | Zhang |
| 7,796,728 B2 | | 9/2010 | Bergfjord |
| 7,813,838 B2 | | 10/2010 | Sommer |
| 7,835,778 B2 | | 11/2010 | Foley et al. |
| 7,835,784 B2 | | 11/2010 | Mire et al. |
| 7,840,256 B2 | | 11/2010 | Lakin et al. |
| 7,844,320 B2 | | 11/2010 | Shahidi |
| 7,853,305 B2 | | 12/2010 | Simon et al. |
| 7,853,313 B2 | | 12/2010 | Thompson |
| 7,900,524 B2 | | 3/2011 | Calloway et al. |
| 7,940,999 B2 | | 5/2011 | Liao et al. |
| 7,945,012 B2 | | 5/2011 | Ye et al. |
| 7,945,021 B2 | | 5/2011 | Shapiro et al. |
| 8,019,045 B2 | | 9/2011 | Kato |
| 8,021,310 B2 | | 9/2011 | Sanborn et al. |
| D646,703 S | | 10/2011 | Wong |
| 8,052,688 B2 | | 11/2011 | Wolf, II |
| 8,086,299 B2 | | 12/2011 | Adler et al. |
| 8,098,914 B2 | | 1/2012 | Liao et al. |
| 8,100,950 B2 | | 1/2012 | St. Clair et al. |
| D654,503 S | | 2/2012 | Sapper |
| 8,116,430 B1 | | 2/2012 | Shapiro et al. |
| 8,121,249 B2 | | 2/2012 | Wang et al. |
| D655,324 S | | 3/2012 | Wong |
| 8,150,494 B2 | | 4/2012 | Simon et al. |
| D660,845 S | | 5/2012 | Schmauch et al. |
| 8,208,708 B2 | | 6/2012 | Homan et al. |
| 8,224,024 B2 | | 7/2012 | Foxlin et al. |
| 8,311,611 B2 | | 11/2012 | Csavoy et al. |
| 8,335,557 B2 | | 12/2012 | Maschke |
| 8,358,818 B2 | | 1/2013 | Miga et al. |
| 8,379,791 B2 | | 2/2013 | Forthmann et al. |
| 8,386,019 B2 | | 2/2013 | Camus et al. |
| D679,016 S | | 3/2013 | Jarva |
| 8,394,099 B2 | | 3/2013 | Patwardhan |
| 8,462,911 B2 | | 6/2013 | Vesel et al. |
| D685,479 S | | 7/2013 | Charles |
| 8,509,503 B2 | | 8/2013 | Nahum et al. |
| D690,421 S | | 9/2013 | Charles |
| 8,526,700 B2 | | 9/2013 | Isaacs |
| 8,541,970 B2 | | 9/2013 | Nowlin et al. |
| D692,139 S | | 10/2013 | Charles |
| 8,560,118 B2 | | 10/2013 | Green et al. |

(56) References Cited

U.S. PATENT DOCUMENTS

| | | |
|---|---|---|
| 8,597,198 B2 | 12/2013 | Sanborn et al. |
| 8,611,985 B2 | 12/2013 | Lavallee et al. |
| 8,630,389 B2 | 1/2014 | Kato |
| 8,634,897 B2 | 1/2014 | Simon et al. |
| 8,660,635 B2 | 2/2014 | Simon et al. |
| 8,678,647 B2 | 3/2014 | Gregerson et al. |
| D702,841 S | 4/2014 | Wyrozub |
| 8,696,458 B2 | 4/2014 | Foxlin et al. |
| 8,706,185 B2 | 4/2014 | Foley et al. |
| 8,727,618 B2 | 5/2014 | Maschke et al. |
| 8,738,115 B2 | 5/2014 | Amberg et al. |
| 8,740,882 B2 | 6/2014 | Jun et al. |
| D708,332 S | 7/2014 | Kim |
| 8,781,186 B2 | 7/2014 | Clements et al. |
| 8,781,630 B2 | 7/2014 | Banks et al. |
| 8,787,520 B2 | 7/2014 | Baba |
| 8,792,704 B2 | 7/2014 | Isaacs |
| 8,798,231 B2 | 8/2014 | Notohara et al. |
| 8,812,077 B2 | 8/2014 | Dempsey |
| 8,814,793 B2 | 8/2014 | Brabrand |
| 8,818,105 B2 | 8/2014 | Myronenko et al. |
| 8,821,511 B2 | 9/2014 | Von Jako et al. |
| 8,867,703 B2 | 10/2014 | Shapiro et al. |
| 8,888,821 B2 | 11/2014 | Rezach et al. |
| 8,964,934 B2 | 2/2015 | Ein-Gal |
| D724,738 S | 3/2015 | Dorris et al. |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,125,680 B2 | 9/2015 | Kostrzewski et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0193800 A1* | 12/2002 | Kienzle, III ........ A61B 17/1703 606/80 |
| 2003/0056561 A1* | 3/2003 | Butscher ............ A61C 7/04 72/295 |
| 2003/0097060 A1 | 5/2003 | Yanof et al. |
| 2004/0034282 A1 | 2/2004 | Quaid |
| 2004/0076259 A1 | 4/2004 | Jensen et al. |
| 2004/0128026 A1 | 7/2004 | Harris et al. |
| 2004/0143168 A1 | 7/2004 | Hu et al. |
| 2004/0254680 A1* | 12/2004 | Sunaoshi ............ A61B 34/37 700/253 |
| 2005/0245817 A1 | 11/2005 | Clayton et al. |
| 2006/0036264 A1 | 2/2006 | Selover et al. |
| 2006/0142657 A1 | 6/2006 | Quaid et al. |
| 2006/0161136 A1 | 7/2006 | Anderson et al. |
| 2006/0161138 A1 | 7/2006 | Orban et al. |
| 2006/0184396 A1 | 8/2006 | Dennis et al. |
| 2006/0291612 A1 | 12/2006 | Nishide et al. |
| 2007/0005189 A1 | 1/2007 | Furubo |
| 2007/0021738 A1* | 1/2007 | Hasser ............ A61B 19/22 606/1 |
| 2007/0032906 A1 | 2/2007 | Sutherland et al. |
| 2007/0038059 A1 | 2/2007 | Sheffer et al. |
| 2007/0055291 A1 | 3/2007 | Birkmeyer et al. |
| 2007/0073133 A1 | 3/2007 | Schoenefeld |
| 2007/0119123 A1 | 5/2007 | Clark et al. |
| 2007/0144298 A1* | 6/2007 | Miller ............ B25J 9/1676 74/490.01 |
| 2007/0156157 A1 | 7/2007 | Nahum et al. |
| 2007/0270685 A1 | 11/2007 | Kang et al. |
| 2008/0004523 A1 | 1/2008 | Jensen |
| 2008/0013809 A1 | 1/2008 | Zhu et al. |
| 2008/0082109 A1 | 4/2008 | Moll et al. |
| 2008/0108991 A1 | 5/2008 | Von Jako |
| 2008/0144906 A1 | 6/2008 | Allred et al. |
| 2008/0161680 A1 | 7/2008 | Von Jako et al. |
| 2008/0215181 A1 | 9/2008 | Smith et al. |
| 2008/0221520 A1 | 9/2008 | Nagel et al. |
| 2008/0235052 A1 | 9/2008 | Node-Langlois et al. |
| 2008/0269596 A1 | 10/2008 | Revie et al. |
| 2008/0287781 A1 | 11/2008 | Revie et al. |
| 2008/0287862 A1 | 11/2008 | Weitzner et al. |
| 2008/0300477 A1 | 12/2008 | Lloyd et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0088848 A1 | 4/2009 | Martz et al. |
| 2009/0185655 A1 | 7/2009 | Koken et al. |
| 2009/0198121 A1 | 8/2009 | Hoheisel |
| 2009/0259412 A1* | 10/2009 | Brogardh ............ B25J 9/1633 702/41 |
| 2009/0326318 A1 | 12/2009 | Tognaccini et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0166496 A1 | 7/2010 | Bennett et al. |
| 2010/0192720 A1 | 8/2010 | Helmer et al. |
| 2010/0210939 A1 | 8/2010 | Hartmann et al. |
| 2010/0228117 A1 | 9/2010 | Hartmann |
| 2010/0240989 A1* | 9/2010 | Stoianovici ............ A61B 34/70 600/429 |
| 2010/0274120 A1 | 10/2010 | Heuscher |
| 2010/0292843 A1* | 11/2010 | Kariyazaki ............ B25J 9/1676 700/264 |
| 2010/0319713 A1 | 12/2010 | Byers et al. |
| 2011/0082462 A1 | 4/2011 | Suarez et al. |
| 2011/0087238 A1 | 4/2011 | Wang et al. |
| 2011/0098553 A1 | 4/2011 | Robbins et al. |
| 2011/0126844 A1 | 6/2011 | Cinquin et al. |
| 2011/0190789 A1 | 8/2011 | Thiran et al. |
| 2011/0282189 A1 | 11/2011 | Graumann |
| 2011/0286573 A1 | 11/2011 | Schretter et al. |
| 2012/0035507 A1 | 2/2012 | George et al. |
| 2012/0051498 A1 | 3/2012 | Koishi |
| 2012/0059378 A1 | 3/2012 | Farrell |
| 2012/0143084 A1 | 6/2012 | Shoham |
| 2012/0226145 A1 | 9/2012 | Chang et al. |
| 2012/0235909 A1 | 9/2012 | Birkenbach et al. |
| 2012/0283746 A1* | 11/2012 | Hu ............ A61B 34/30 606/130 |
| 2012/0294498 A1 | 11/2012 | Popovic |
| 2013/0016889 A1 | 1/2013 | Myronenko et al. |
| 2013/0060146 A1 | 3/2013 | Yang et al. |
| 2013/0081636 A1 | 4/2013 | Schuele |
| 2013/0094742 A1 | 4/2013 | Feilkas |
| 2013/0113791 A1 | 5/2013 | Isaacs et al. |
| 2013/0113798 A1 | 5/2013 | Nahum et al. |
| 2013/0131867 A1* | 5/2013 | Olds ............ B25J 9/10 700/260 |
| 2013/0165937 A1 | 6/2013 | Patwardhan |
| 2013/0172902 A1 | 7/2013 | Lightcap et al. |
| 2013/0211590 A1* | 8/2013 | Diolaiti ............ B25J 9/1689 700/257 |
| 2013/0281821 A1 | 10/2013 | Liu et al. |
| 2013/0307955 A1 | 11/2013 | Deitz et al. |
| 2013/0317344 A1 | 11/2013 | Borus et al. |
| 2013/0342578 A1 | 12/2013 | Isaacs |

(56) References Cited

U.S. PATENT DOCUMENTS

| | | |
|---|---|---|
| 2013/0345757 A1 | 12/2013 | Stad |
| 2014/0046132 A1 | 2/2014 | Hoeg et al. |
| 2014/0049629 A1 | 2/2014 | Siewerdsen et al. |
| 2014/0052150 A1* | 2/2014 | Taylor ............... A61F 9/00727 606/130 |
| 2014/0052151 A1 | 2/2014 | Hingwe et al. |
| 2014/0066944 A1 | 3/2014 | Taylor et al. |
| 2014/0080086 A1 | 3/2014 | Chen |
| 2014/0096369 A1 | 4/2014 | Matsumoto et al. |
| 2014/0121676 A1 | 5/2014 | Kostrzewski et al. |
| 2014/0135796 A1 | 5/2014 | Simon et al. |
| 2014/0142592 A1* | 5/2014 | Moon ................ A61B 34/30 606/130 |
| 2014/0148950 A1* | 5/2014 | Ogawa ............... A61B 17/29 700/257 |
| 2014/0130810 A1 | 8/2014 | Azizian et al. |
| 2014/0221819 A1 | 8/2014 | Sarment |
| 2014/0234804 A1 | 8/2014 | Huang et al. |
| 2014/0303643 A1* | 10/2014 | Ha .................... A61B 19/2203 606/130 |
| 2014/0371577 A1 | 12/2014 | Maillet et al. |
| 2015/0032164 A1 | 1/2015 | Crawford et al. |
| 2015/0039034 A1 | 2/2015 | Frankel et al. |
| 2015/0045764 A1 | 2/2015 | Kaplan et al. |
| 2015/0045813 A1 | 2/2015 | Kostrzewski et al. |
| 2015/0085970 A1 | 3/2015 | Bouhnik et al. |
| 2015/0100066 A1 | 4/2015 | Kostrzewski et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0196365 A1 | 7/2015 | Kostrzewski et al. |
| 2015/0202009 A1 | 7/2015 | Nussbaumer et al. |
| 2015/0213633 A1 | 7/2015 | Chang et al. |
| 2015/0223897 A1 | 8/2015 | Kostrzewski et al. |
| 2015/0305817 A1 | 10/2015 | Kostrzewski |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

FOREIGN PATENT DOCUMENTS

| | | |
|---|---|---|
| EP | 1693011 A1 | 8/2006 |
| EP | 1987406 | 11/2008 |
| WO | WO-98/02107 A1 | 1/1998 |
| WO | WO-2004/014244 A2 | 2/2004 |
| WO | WO-2005/122916 A1 | 12/2005 |
| WO | WO-2006/091494 A1 | 8/2006 |
| WO | WO-2007/136768 A2 | 11/2007 |
| WO | WO-2008/097540 A2 | 8/2008 |
| WO | WO-2009/013406 A2 | 1/2009 |
| WO | 2012018816 A2 | 2/2012 |
| WO | WO-2012/131660 A1 | 10/2012 |
| WO | WO-2012/133912 A1 | 10/2012 |
| WO | WO-2013/079843 A1 | 6/2013 |
| WO | WO-2013/098496 A1 | 7/2013 |
| WO | WO-2013/160239 A1 | 10/2013 |
| WO | WO-2013/192598 A1 | 12/2013 |
| WO | WO-2015/049109 A1 | 4/2015 |
| WO | WO-2015/107099 A1 | 7/2015 |
| WO | WO-2015/110542 A1 | 7/2015 |
| WO | WO-2015/121311 A1 | 8/2015 |
| WO | WO-2015/162256 A1 | 10/2015 |

OTHER PUBLICATIONS

Written Opinion of the International Search Authority for WO/2012/131660 dated Oct. 1, 2013.

Zemiti, N. et al., A new Robot for Force Control in Minimally Invasive Surgery, Proceedings of 2004 IEEE/RSJ International Conference on Intelligent Robots and Systems, 4:3643-3648 (2004).

* cited by examiner

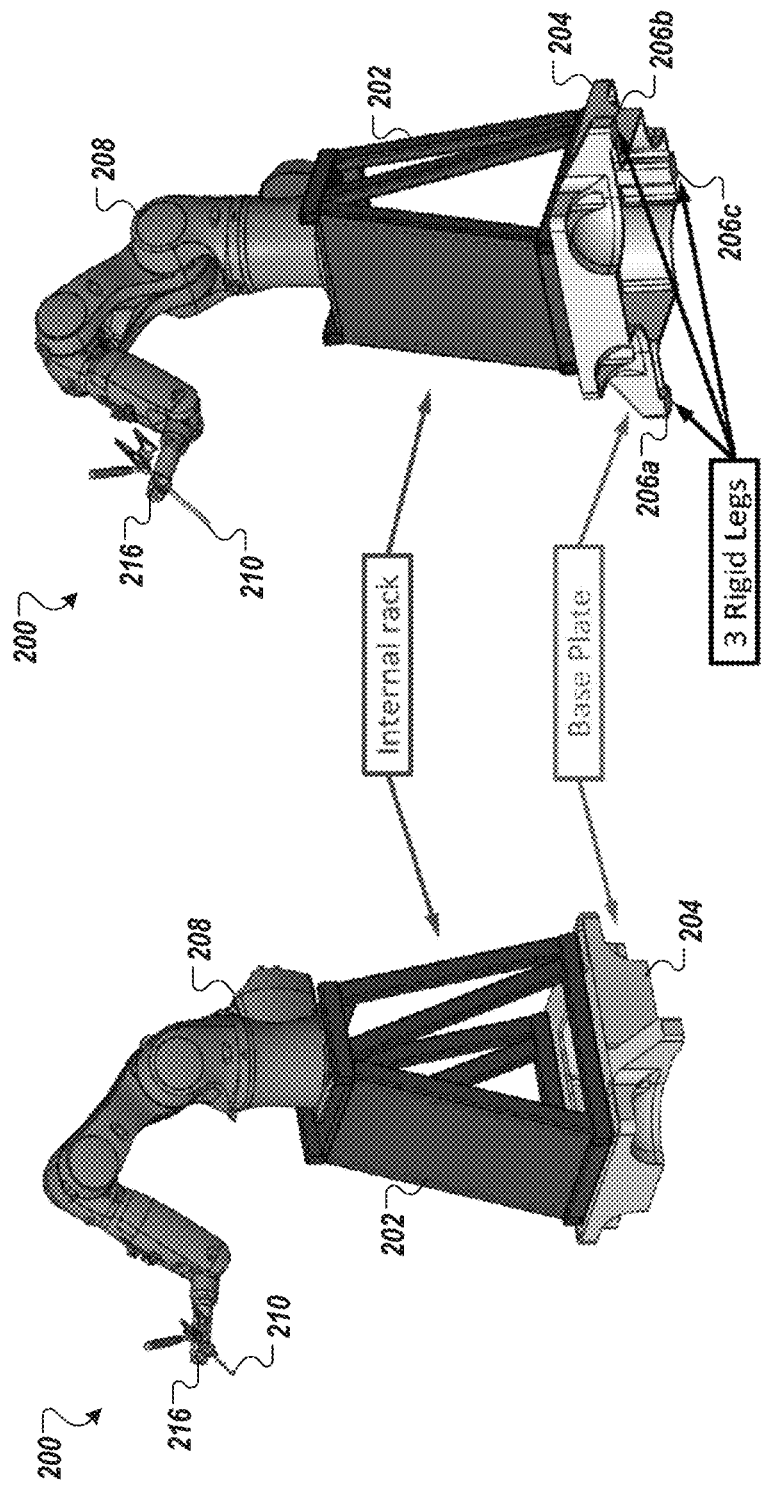

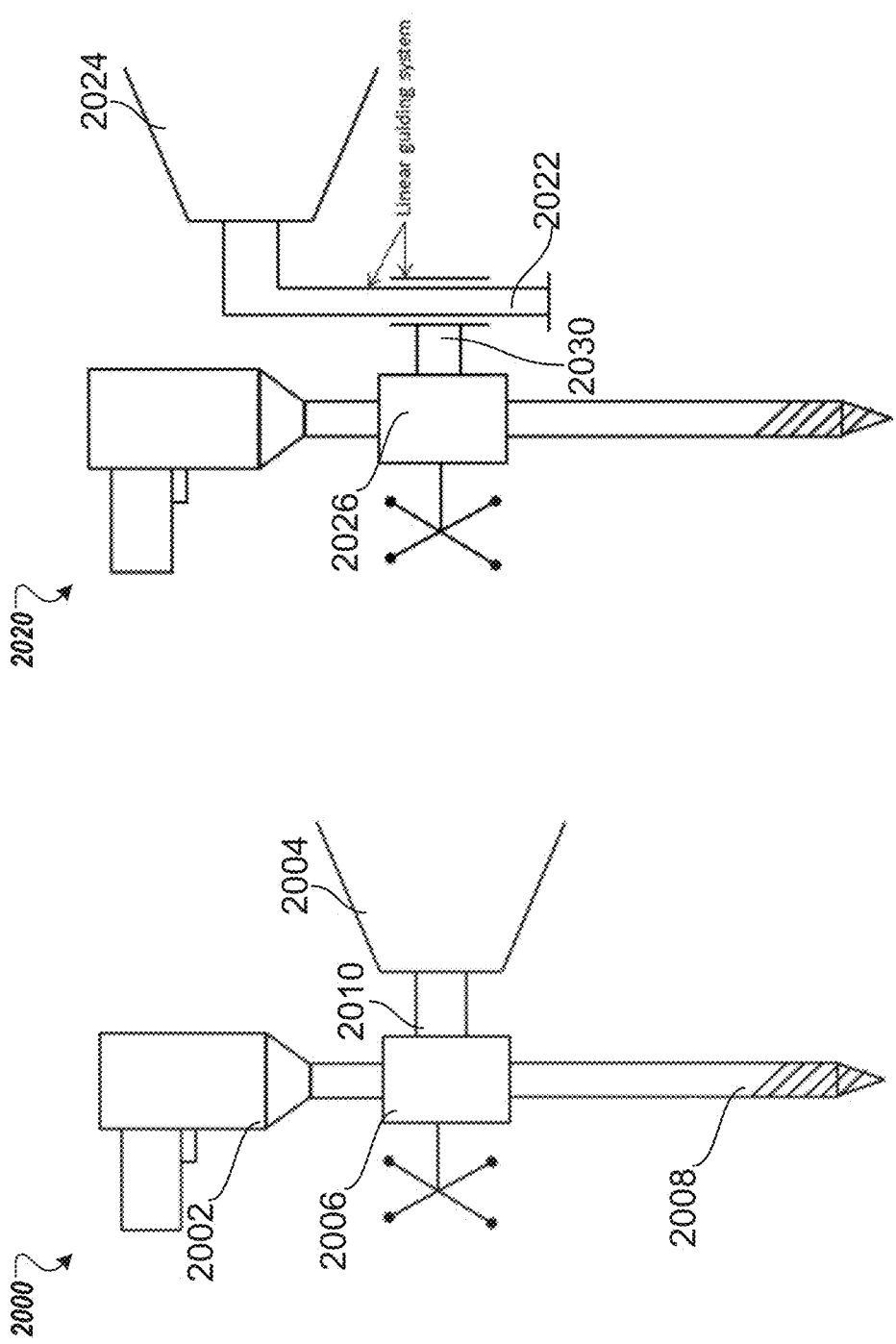

2300

```
┌─────────────────────────────────────────────┐
│ Generate Virtual Representation of Patient Situation │
│                                        2302 │
└─────────────────────────────────────────────┘
                      │
                      ▼
┌─────────────────────────────────────────────┐
│   Place Robot Arm into Surgical Preparation │
│              Configuration            2304  │
└─────────────────────────────────────────────┘
                      │
                      ▼
┌─────────────────────────────────────────────┐
│           Stabilize Robot Mobile Cart       │
│                                        2306 │
└─────────────────────────────────────────────┘
                      │
                      ▼
┌─────────────────────────────────────────────┐
│ Place Robot Arm into Force Control Mode for Surgeon │
│  to Position the Tool Guide for Alignment with a    │
│           Determined Trajectory        2308 │
└─────────────────────────────────────────────┘
                      │
                      ▼
┌─────────────────────────────────────────────┐
│   Manipulate Tool According to Calculated   │
│  Trajectory to Perform Surgical Procedure   │
│                                        2310 │
└─────────────────────────────────────────────┘
```

FIG. 23

APPARATUS AND SYSTEMS FOR PRECISE GUIDANCE OF SURGICAL TOOLS

The present application claims priority to U.S. patent application Ser. No. 14/266,769, filed Apr. 30, 2014, entitled "Apparatus and Systems for Precise Guidance of Surgical Tools," which claims priority to U.S. Provisional Patent Application No. 61/887,273, entitled "Apparatus, Systems, and Methods for Precise Guidance of Surgical Tools" and filed Oct. 4, 2013, the contents of all of which are hereby incorporated by reference in their entireties.

BACKGROUND OF THE INVENTION

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeon's field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Spinal surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

Image-guided spinal surgeries involve optical tracking to aid in screw placement. However, such procedures are currently performed manually, and surgical tools can be inaccurately positioned despite virtual tracking. A surgeon is required to coordinate his real-world, manual manipulation of surgical tools using images displayed on a two dimensional screen. Such procedures can be non-intuitive and require training, since the surgeon's eye must constantly scan both the surgical site and the screen to confirm alignment. Furthermore, procedural error can result in registration inaccuracy of the image-guiding system, rendering it useless, or even misleading.

Certain force feedback systems are used by surgeons in certain procedures; however such systems have a large footprint and take up valuable, limited space in the operating room. These systems also require the use of surgical tools that are specially adapted for use with the force feedback system, and the training required by surgeons to operate such systems can be significant. Moreover, surgeons may not be able to use expertise they have developed in performing spinal surgeries when adapting to use of the current force feedback systems. Such systems, while precise, may require more surgical time and more operating room preparation time to ready placement of the equipment for surgery. Thus, there is a need for systems, apparatus, and methods that provide enhanced precision in performing surgeries such as spinal surgeries.

SUMMARY OF THE INVENTION

Described herein are systems, apparatus, and methods for precise placement and guidance of tools during surgery, particularly spinal surgery. The system features a portable robot arm with end effector for precise positioning of a surgical tool. The system requires only minimal training by surgeons/operators, is intuitive to use, and has a small footprint with significantly reduced obstruction of the operating table. The system works with existing, standard surgical tools, does not require increased surgical time or preparatory time, and safely provides the enhanced precision achievable by robotic-assisted systems. Moreover, the system allows for a desired trajectory (e.g., for a drill guide during spinal surgery) to be set in a variety of manners based on the circumstances of the surgery. For example, some surgical procedures are planned pre-operatively with the surgeon defining the desired position of an implant using imaging technology, such as CT images (e.g., 3D CT images). The desired position of the implant may also be determined and proposed by the system. In the operating room the surgeon may be guided by the robotic system (e.g., robotic guidance of the surgical tools) to accurately execute the planning.

Some operations are performed with little or no pre-operative planning. For example, the surgery may be an emergency surgical operation and the surgery planning may be performed intra-operatively. In some implementations, the robotic surgical system permits the surgeon to define the trajectory intra-operatively with little or no pre-operative planning. The surgeon may define the trajectory by positioning the end-effector in a desired position. As the surgeon moves the end effector, a projected trajectory may be displayed based on the position of the end-effector. The surgeon may view this display to adjust the position of the end-effector until he/she positions the end-effector such that a desired trajectory is obtained. Thus, the surgeon may define the trajectory in the operating room with little or no pre-operative planning. In some implementations, the surgeon may utilize images (e.g., CT scans) taken during a pre-operative planning session to assist with defining the trajectory. Moreover, the disclosed technology provides the surgeon with reliable instruments and techniques to successfully perform his/her surgery. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient. Once in the desired position, the tool holder can serve as a stable, secure guide through which a tool may be moved through or slid at an accurate angle. An accurate trajectory may be determined by real-time monitoring of a patient situation during a surgical procedure, e.g., via markers placed at certain key locations, coupled with 3D images of the patient obtained prior to surgery or during the surgical procedure. In certain embodiments, the robot secures the tool holder in place, and the tool holder does not move during operation of the tool. For example, the tool holder may be shaped to allow sliding of a drill bit through the tool holder at the precisely determined, continually held trajectory. In other embodiments, the robot provides real time compensation of the position/trajectory of the tool holder due to movement of the vertebrae or other movement of the patient during a surgical procedure, such that the angle at which the tool holder is placed adjusts according to such movement, thereby maintaining the proper trajectory during the procedure.

A mobile cart houses a robot arm with an end effector that holds various standard surgical tools/implants, such as a drill or screw. Positioning such surgical tools with precision is critical. The robot arm provides more precise, stable placement of such tools than can be achieved manually, where placement is guided, yet intuitive. The mobile cart permits easy set-up and use of the system. Once stabilization is engaged, the mobile cart is secured in place on the operating room floor and cannot move. In certain embodiments, the robot cart houses the robot, robot controller, supervisor interlock system, power system, riding system, and interface to the navigation system.

In one aspect, described herein is a robotic surgical system for performing a surgical procedure that includes a robotic arm comprising a force controlled end-effector configured to hold a first surgical tool. The surgical system includes a manipulator configured to allow robotically-assisted or unassisted positioning and/or movement of the end-effector by a user with at least four degrees of freedom (e.g., six degrees of freedom—three translations and three rotations). The surgical system includes an actuator for controlled movement of the robotic arm and/or positioning of the end-effector. The surgical system, in some implementations, includes a tracking detector for real time detection of a surgical tool position and/or end-effector position and patient position. The surgical system may also include a processor and a non-transitory computer readable medium storing instructions thereon wherein the instructions, when executed, cause the processor to access or generate a virtual representation of a patient situation (e.g., a 3D model of the patient's spinal column and surrounding tissue, medical images shown in typical medical planes, etc.). In some implementations, when executed, the instructions cause the processor to calculate a desired trajectory from the virtual representation of the patient situation. In some implementations, a surgeon defines the trajectory. The surgeon may define the trajectory by positioning the end-effector in a desired position. As the surgeon moves the end effector, a projected trajectory may be displayed based on the position of the end-effector. The surgeon may view this display to adjust the position of the end-effector until he/she positions the end-effector such that a desired trajectory is obtained. Thus, the surgeon may define the trajectory in the operating room with little or no pre-operative planning. In some implementations, the surgeon may utilize images (e.g., CT scans) taken during a pre-operative planning session to assist with defining the trajectory.

When executed, the instructions may cause the processor to obtain or calculate a real-time surgical tool position and/or end-effector position and patient position from the tracking detector. In some implementations, when executed, the instructions cause the processor to render and display a real-time representation of the desired trajectory, the surgical tool position and/or the end-effector position in relation to the real-time patient position. When executed, the instructions cause the processor to detect a force applied by a user to the end-effector, via the manipulator, in real-time and determine whether the force exceeds a predetermined minimum force required for movement of the end-effector. In some implementations, the minimum force required is zero. Upon detection of a force applied to the end-effector that exceeds the predetermined minimum force, the processor is instructed to controlling the actuator to move the end-effector (e.g., in a direction corresponding to a direction of application of the force) at a predetermined measured pace (e.g., at a steady, slow velocity, or at an initially very slow velocity, gradually increasing in a controlled manner to a greater velocity) for positioning of the surgical tool position and/or end-effector position in relation to (e.g., in alignment with) the calculated desired trajectory.

In some embodiments, the robotic arm is configured to releasably hold the first surgical tool, allowing the first surgical tool to be removed and replaced with a second surgical tool without re-registration, or with automatic or semi-automatic re-registration of position of the end-effector. In some embodiments, the manipulator is a handle attached directly or indirectly to the end-effector such as a serial manipulator, or a part of the end-effector itself. In some embodiments, the tracking detector monitors patient position by monitoring the position of one or more vertebrae, or markers placed in spatial relation to one or more vertebrae.

In some embodiments, the instructions further cause the processor to, upon entry of a user command, control the actuator to translate the end-effector an identified distance (e.g, 5 mm) in an identified direction (e.g., move the end-effector by 1 mm in a given direction) and/or to adjust angle of rotation of the end-effector (e.g., adjust the roll, yaw, or pitch by 0.1 degree).

In some embodiments, there is a supervisory interlock system, separate from the processor, that controls the actuator to move the end-effector. The supervisory interlock system, in some implementations, is configured to brake any movement of the robotic arm upon detection by the supervisory interlock system of an anomaly or problem. In some implementations, in response to detection of an anomaly or problem, the supervisory interlock system slows motion down, triggers alarms, requires additional checks be performed, and/or requires user confirmation.

In some embodiments, the manipulator comprises a switch mechanism such as a pair of push buttons. Upon activation of the switch mechanism by a user, an end-effector previously controlled in a force control mode (e.g., the impedance controlled movement at the predetermined measured pace upon application and detection of user force applied to the end-effector in excess of the predetermined minimum force) is switched to an active holding position (e.g., the end-effector will not move), and/or an end-effector previously in an active holding position is switched to a force control mode. The switch mechanism may be push buttons, pedals, voice based input device, gesture based input device, touch screen, touch pad, presence detectors, other types of operator activated switches, or a combination thereof.

In some embodiments, the switch mechanism is configured to require deliberate manipulation of more than one physical component (e.g., more than one push-button), thereby avoiding accidental activation of the switch mechanism.

In another aspect, described herein is a mobile cart for use with a robotic surgical system for performing a surgical procedure (e.g., spinal surgical procedure), which includes a housing with one or more wheels (or other means of translocation) and an attached or embedded handle for locomotion of the mobile cart by an operator. The mobile cart includes a stabilizing/braking/locking mechanism for preventing movement of the mobile cart upon engagement of the mechanism. The mobile cart also includes a robot that includes an arm with an end-effector configured to hold a first surgical tool (e.g., configured to releasably hold the first surgical tool, allowing the first surgical tool to be removed and replaced with a second surgical tool, e.g., without re-registration, or with automatic or semi-automatic re-registration of position of the end-effector). The robot is configured to control and/or allow positioning and/or movement of the end-effector with at least four degrees of freedom (e.g., six degrees of freedom, three translations and three rotations). The robot also includes an actuator for moving the arm and a power source (e.g., battery and back-up battery) for powering the actuator. The robot further includes a processor for controlling movement of the robot arm (e.g., and/or for controlling, engaging, and/or disengaging the stabilizing/braking/locking mechanism of the mobile cart—or, the braking/locking mechanism may be entirely mechanical for simplicity). The mobile cart further includes a control panel configured for selection by an operator of one of a plurality of preset positions of the robot arm (e.g., via pressing a corresponding physical button or touch-sensitive printed button on the control panel) (e.g., and for selection by an operator of an on-off power button/switch) (e.g., and for engagement or disengagement of the stabilizing/braking/locking mechanism) (e.g., and for engagement or disengagement of a surgical procedure mode) (e.g., wherein the selectable preset positions of the robot arm correspond to (i) a drape configuration, (ii) a preparation configuration, and (iii) a stand-by configuration) (e.g., wherein the display comprises printed (not digital) buttons, e.g., less than 15 buttons for simplicity).

In some embodiments, the footprint of the mobile cart is no greater than 1.0 $m^2$, or no greater than 0.5 $m^2$ (e.g., the footprint is 1 m or less in width and 1 m or less in depth; or the footprint is 600 mm or less in width and 700 mm or less in depth), thereby permitting improved access by a surgeon of both sides of an operating table at which the mobile cart is positioned during an operation. In some implementations, the mobile cart is 682 mm in width and 770 mm in depth. In some implementations, the cart may include rigid legs that extend on the sides of the cart for more stable positioning.

In some embodiments, the end-effector comprises a tool connector that accommodates a sterile drape covering the mobile cart. The sterile drape may cover the entire mobile cart, including the robot arm and the end-effector. In some implementations, the sterile drape may cover the whole robot arm and a portion of the cart (e.g., the majority of the cart excluding the bottom and the control panel).

In another aspect, described herein is a method of performing a surgical procedure (e.g., a spinal surgical procedure) with a robotic surgical system, the method including: obtaining or accessing an image of a patient situation (e.g., a 3D CT scan or 3D fluoroscopy); moving a mobile cart transporting a robotic surgical system comprising a robotic arm in proximity to an operating table, wherein the robotic arm comprises an end effector (e.g., surgical tool holder); stabilizing the mobile cart (e.g., onto the operating room floor); computing, by a processor of a computing device, a desired trajectory for a surgical tool from the image of the patient situation and from a detected real-time position of the surgical tool and/or end effector of the robotic arm (e.g., wherein the computed trajectory is a desired path of the surgical tool, e.g., drill, through the tissue, e.g., vertebrae, bone); aligning (e.g., via force control mode operation) (e.g., manually, semi-manually, and/or automatically) the end effector in accordance with the computed and/or desired trajectory; and maneuvering the surgical tool into/onto patient tissue, wherein the surgical tool is constrained by the end effector (e.g., end effector is a drill bit tube, the surgical tool comprises a drill bit, and the drill bit is maneuvered through the tube). In certain embodiments, the robotic surgical system is an embodiment of the robotic surgical system described above or elsewhere herein. In some embodiments, the desired trajectory is determined automatically or semi-automatically, using a software algorithm and/or using input from the surgeon. In some implementations, the surgeon determines the desired trajectory. The surgeon may define the trajectory based on images (e.g., CT scans) taken during a pre-operative planning session. In some implementations, the surgeon may define the trajectory in the operating room with little or no pre-operative planning. Thus, the disclose technology enables surgeons to quickly plan and perform surgical procedures with assistance from a robot.

The disclosed technology, in some implementations, includes a robotic surgical system for performing surgery. The robotic surgical system may be configured to permit a surgeon to manually move the end-effector to a position for an operation without pre-operative planning. The system may include a robotic arm comprising a force control end-effector configured to hold a first surgical tool; a manipulator configured to allow robotically-assisted or unassisted positioning and/or movement of the end-effector by a user with at least four degrees of freedom; an actuator for controlled movement of the robotic arm and/or positioning of the end-effector; a tracking detector (e.g., camera) for real time detection of (i) surgical tool position and/or end-effector position and (ii) patient position (e.g, a position of one or more vertebrae); and a processor and a non-transitory computer readable medium storing instructions thereon wherein the instructions, when executed, cause the processor to: access or generate a virtual representation of a patient situation; obtain a real-time (i) surgical tool position and/or end-effector position and (ii) patient position from the tracking detector; determine a projected trajectory based on the (a) surgical tool position and/or end-effector position and (b) patient position from the tracking detector; and render and display a real-time representation of the projected trajectory, the surgical tool position and/or the end-effector position in relation to the real-time patient position, wherein the determination of the projected trajectory and the rendering and display of the projected trajectory is updated as the position of the end-effector is changed, thereby providing visual feedback to the user to assist the user in positioning the end-effector at a desired position.

The system may include a supervisory interlock system, separate from the processor that controls the actuator to move the end-effector, wherein the supervisory interlock system is configured to influence any movement of the robotic arm upon detection by the supervisory interlock system of an anomaly or problem.

In some implementations, the manipulator includes a switch mechanism, and wherein, upon activation of the switch mechanism by a user, an end-effector previously controlled in a force control mode is switched to an active holding position, and/or an end-effector previously in the active holding position is switched to a force control mode. The switch mechanism may be configured to require deliberate manipulation of more than one physical component, thereby avoiding accidental activation of the switch mechanism. The end-effector may be configured to releasably hold the first surgical tool, allowing the first surgical tool to be removed and replaced with a second surgical tool without re-registration. In some implementations, the end-effector is configured to releasably hold the first surgical tool, allowing the first surgical tool to be removed and replaced with a second surgical tool with automatic or semi-automatic re-registration of position of the end-effector. A handle (e.g, a sterile handle) may be attached directly or indirectly to the end-effector. The manipulator may be a serial manipulator. The manipulator may be part of the end-effector itself.

The virtual representation of a patient situation may be a 3D model of a spinal column and surrounding tissue. The virtual representation of a patient situation is based on one or more surgical planes of a spinal column and surrounding tissue.

In some implementations, the end-effector is configured to move at a predetermined measured pace upon application and detection of user force applied to the end-effector in excess of the predetermined minimum force and the predetermined measured pace is an initially very slow velocity, gradually increasing in a controlled manner to a greater velocity. In some implementations, as the position of the end-effector is changed, the processor continuously determines and displays a real-time representation of the projected trajectory, the surgical tool position and/or the end-effector position in relation to the real-time patient position.

The disclosed technology, in some implementations, includes a method of performing surgery with a robotic surgical system. The method may include moving a mobile cart transporting a robotic surgical system comprising a robotic arm in proximity to an operating table, wherein the robotic arm comprises an end effector (e.g., surgical tool holder); stabilizing the mobile cart; positioning the end effector based at least in part on a real-time (i) surgical tool (e.g., a drill bit, pedicle finder, screw-based implant, awl, surface-pointing device, screw driver, tap, implant, and implant with extender) position and/or end-effector position and (ii) patient position from a tracking detector, wherein a processor of a computing device is configured to: determine a projected trajectory based on the (a) surgical tool position and/or end-effector position and (b) patient position from the tracking detector, and render and display a real-time representation of the projected trajectory, the surgical tool position and/or the end-effector position in relation to the real-time patient position, wherein the determination of the projected trajectory and the rendering and display of the projected trajectory is updated as the position of the end-effector is changed, thereby providing visual feedback to a user to assist the user in positioning the end-effector at a desired position; and maneuvering the surgical tool in a manner that is constrained by the end effector. The projected trajectory (e.g., desired path of the surgical tool), in some implementations, is identified by a surgeon. The surgery, in some implementations, is spinal surgery. In some implementations, the method includes, prior to positioning the end effector, obtaining or accessing a CT scan, 3D CT scan, fluoroscopy, 3D fluoroscopy, or natural landmark-based image of a patient situation.

The mobile cart, in some implementations, is stabilized onto the operating room floor. Stabilizing the mobile cart may include retracting one or more wheels on the mobile cart such that the mobile cart rests on one or more rigid legs of the mobile cart. Stabilizing the mobile cart may include extracting one or more rigid legs on the mobile cart such that the mobile cart rests on the one or more rigid legs of the mobile cart. The method may include maneuvering the surgical tool in a manner that is constrained by the end effector to the desired position comprises moving the tool along a fixed trajectory constrained by the end-effector.

In some implementations, the method includes maneuvering the surgical tool through the instrument tube. For example, the instrument tube may be a drill bit tube and the surgical tool may be a drill bit and the method may include maneuvering the drill bit through the drill bit tube. The feedback, in some implementations, is via a force control mode operation. The force control mode operation is a manual, semi-manual, automatic force control mode. The disclosed technology, in some implementations, includes a robotic surgical system for performing surgery. The system may include a robotic arm comprising a force control end-effector configured to hold a first surgical tool; a manipulator configured to allow robotically-assisted or unassisted positioning and/or movement of the end-effector by a user with at least four degrees of freedom; an actuator for controlled movement of the robotic arm and/or positioning of the end-effector; a tracking detector for real time detection of (i) surgical tool position and/or end-effector position and (ii) patient position; and a processor and a non-transitory computer readable medium storing instructions thereon wherein the instructions, when executed, cause the processor to: access or generate a virtual representation (e.g., 3D model of a spinal column and surrounding tissue) of a patient situation; calculate a desired trajectory from the virtual representation of the patient situation; obtain a real-time (i) surgical tool position and/or end-effector position and (ii) patient position from the tracking detector; render and display a real-time representation of the desired trajectory, the surgical tool position and/or the end-effector position in relation to the real-time patient position; detect a force applied by a user to the end-effector in real-time and determine whether the force exceeds a predetermined minimum force required for movement of the end-effector; and upon detection of a force applied to the end-effector that exceeds the predetermined minimum force, controlling the actuator to move the end-effector at a predetermined measured pace for positioning of the surgical tool position and/or end-effector position in relation to the calculated desired trajectory.

In some implementations, positioning of the surgical tool position and/or end-effector position in relation to the calculated desired trajectory includes positioning of the surgical tool position and/or end-effector position in alignment with the calculated desired trajectory. In some implementations, determining whether the force exceeds a predetermined minimum force required for movement of the end-effector is for impedance control, and resistance to small, accidental movements.

The disclosed technology, in some implementations, a mobile cart for use with a robotic surgical system for performing surgery. The mobile cart may include a housing with one or more wheels and an attached or embedded handle for locomotion of the mobile cart by an operator; and a stabilizing mechanism for preventing movement of the mobile cart upon engagement of the mechanism; a robot including an arm comprising an end-effector configured to hold a first surgical tool, wherein the robot is configured to control and/or allow positioning and/or movement of the end-effector with at least four degrees of freedom, an actuator for moving the arm, a power source (e.g., a battery and/or a back-up battery) for powering the actuator, and a processor for controlling movement of the robot arm; and a control panel configured for selection by an operator of one of a plurality of preset positions of the robot arm. The footprint of the mobile cart may be no greater than 1.0 m$^2$, or no greater than 0.5 m$^2$ (e.g., the footprint is 682 mm or less in width and 770 mm or less in depth) thereby permitting improved access by a surgeon of both sides of an operating table at which the mobile cart is positioned during an operation. The end-effector may include a tool connector that accommodates a sterile drape covering the mobile cart.

The processor may be configured to control, engage, and/or disengage at least one of a stabilizing, braking, and/or locking mechanism of the mobile cart. The stabilizing mechanism includes a mechanical braking mechanism and an electro-mechanical stabilization system. The control panel may be configured for selection by an operator of one of a plurality of preset positions of the robot arm via pressing a corresponding physical button or touch-sensitive printed button on the control panel. For example, the control panel may be configured for selection by an operator of an on-off power button/switch. The control panel may be configured for engagement or disengagement of at least one of a stabilizing, braking, and/or locking mechanism. The control panel may be configured for engagement or disengagement of a surgery mode. The selectable preset positions of the robot arm may correspond to (i) a drape configuration, (ii) a preparation configuration, and (iii) a stand-by configuration.

In some implementations, the mobile cart includes a display. The display may include printed buttons that are not digital. For example, the display may include less than 15 buttons. In some implementations, the sterile drape covers the entire mobile cart, including the robot arm and the end-effector.

The disclosed technology, in some implementations, includes a method of performing surgery with a robotic surgical system. The method may include obtaining or accessing an image of a patient situation; moving a mobile cart transporting a robotic surgical system comprising a robotic arm in proximity to an operating table, wherein the robotic arm comprises an end effector; stabilizing the mobile cart; computing, by a processor of a computing device, a desired trajectory for a surgical tool from the image of the patient situation and from a detected real-time position of the surgical tool and/or end effector of the robotic arm; aligning (e.g., via a force control mode operation) the end effector in accordance with the computed, desired trajectory; and maneuvering the surgical tool into/onto patient tissue, wherein the surgical tool is constrained by the end effector.

In some implementations, the method includes determining, by a processor of a computing device, a real-time position of the surgical tool and/or end effector of a robot arm of a robotic surgical system, wherein the robotic surgical system is configured to be moved in proximity to an operating table and stabilized on an operating room floor; determining, by a sensor, forces and torques applied to a surgical tool held by an end-effector of a mobile cart during a surgical operation; determining, by the processor, linear and angular correction of a position of the end-effector, wherein the linear and angular correction of the position of the end-effector is based at least in part on a desired trajectory for the surgical tool from an image of a patient situation and from the determined real-time position of the surgical tool and/or end effector of the robot arm; and providing, to one or more motors, by the processor, commands to adjust a position of the end-effector to maintain the desired trajectory for the surgical tool and thereby simplify preoperative surgery planning.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 2A-E are diagrams illustrating an example system for stabilizing a mobile cart during a surgical procedure performed with a surgical robot;

FIGS. 20A-D are diagrams illustrating example configurations of a surgical tool and a surgical end effector attached to a robotic arm of a robotic surgical system, in accordance with various embodiments of the disclosed technology;

FIG. 23 is a flow chart describing an example method for performing a surgical procedure using a robotic surgical system, in accordance with various embodiments of the disclosed technology;

Figure 1:
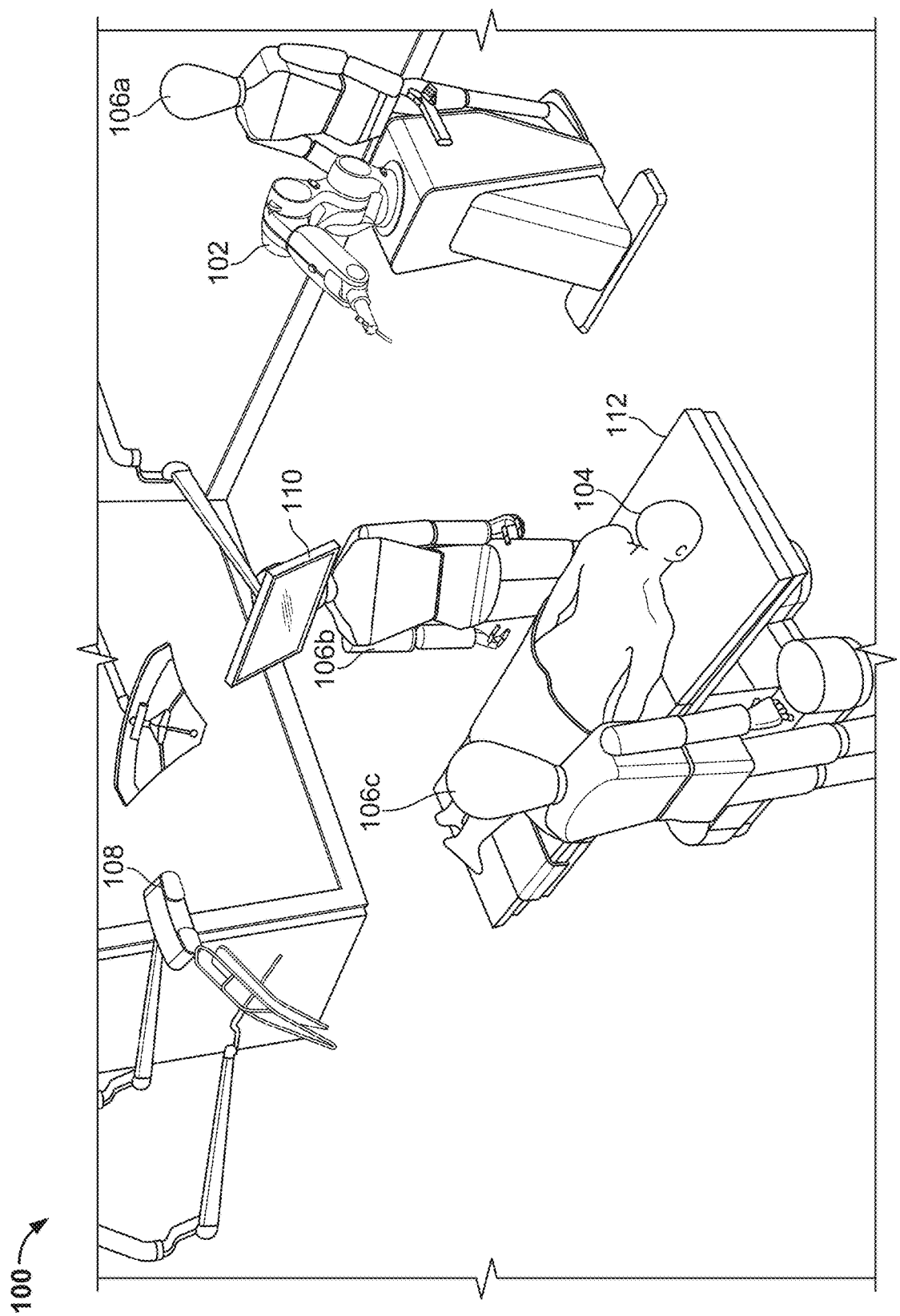
FIG. 1 is a diagram of an operating room in which a mobile cart housing a robotic system for a robotic-assisted spinal surgical procedure is positioned, in accordance with various embodiments of the disclosed technology.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements. Additionally, material disclosed in the background section shall not be construed as an admission of prior art.

DETAILED DESCRIPTION OF THE INVENTION

FIG. 1 illustrates an example surgical robotic system in an operating room 100. In some implementations, one or more surgeons, surgical assistants, surgical technologists and/or other technicians, (106a-c) perform an operation on a patient 104 using a robotic-assisted surgical system. In many surgeries, surgeons do not have time or enough data (e.g. medical images which are obtained pre-operatively) to plan a surgical procedure pre-operatively. The disclosed technology enables a surgeon to plan intra-operatively through the systems hands-on control.

In some implementations, the surgeon defines the trajectory intra-operatively with little or no pre-operative planning. The surgeon may define the trajectory by positioning the end-effector in a desired position. As the surgeon moves the end effector, a projected trajectory may be displayed based on the position of the end-effector. The surgeon may view this display to adjust the position of the end-effector until he/she positions the end-effector such that a desired trajectory is obtained. Thus, the surgeon may define the trajectory in the operating room with little or no pre-operative planning. In some implementations, the surgeon may utilize images (e.g., CT scans) taken during a pre-operative planning session to assist with defining the trajectory. Moreover, the disclosed technology provides the surgeon with reliable instruments and techniques to successfully perform his/her surgery.

In some implementations, the surgical procedure is planned pre-operatively. In one example, the surgeon may define the desired trajectory (e.g., position of an implant) using imaging technology, such as CT images (e.g., 3D CT images). In the operating room the surgeon may be guided by the robotic system to accurately execute the planning. This may be achieved by robotic guidance of the surgical tools.

In another example, the computer of the robotic surgical system assists in defining/identifying the trajectory (e.g., the computer of the robotic surgical system identifies/defines a trajectory which is presented to and/or approved by the surgeon or automatically approved). The computer of the robotic surgical system may analyze digital medical images to define the trajectory. The trajectory may be defined and/or displayed in relation to a marker, a vertebrae, or other physical landmark of the body, by additionally processing input received from a scanning system that identifies the location of such marker, vertebrae, or physical landmark during the surgical procedure, in real time. The trajectory may make use of scans conducted during the procedure, scans conducted prior to the procedure, or both. The scanning conducted prior to the surgical procedure may involve different equipment than scanning performed during the surgical procedure. The scanning may be conducted using a medical imaging device such as a computer tomography scanner, a magnetic resonance image scanner, a nuclear magnetic resonance image scanner, an ultrasound machine, a photoacoustic imager, cardiac sonographer, a thermographic camera, a tactile imager, a 3D fluoroscopy device, or the like.

The computer of the robotic surgical system may also use data regarding prior surgeries, data inputted by a surgeon (e.g., regarding areas to avoid), rankings or ratings for various trajectories that may be used, as well as other information to determine the trajectory. The determined trajectory may be stored by the robotic surgical system for later use during the surgery. For example, in the operating room the surgeon may be guided by the robotic system (e.g., robotic guidance of the surgical tools) to accurately execute at least a portion of the surgical procedure in accordance with the planned trajectory. In some embodiments, the operation may be a spinal surgical procedure, such as a discectomy, a foraminotomy, a laminectomy, or a spinal fusion. In some implementations, the surgical robotic system includes a surgical robot 102 on a mobile cart. The surgical robot 102 may be positioned in proximity to an operating table 112 without being attached to the operating table, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

In some implementations, the footprint of the mobile cart is small (for example, no greater than 682 millimeters by 770 millimeters), thereby permitting improved access by a surgeon of both sides of an operating table at which the mobile cart is positioned during an operation.

The mobile cart may permit a user (operator) 106a, such as a technician, nurse, surgeon, or any other medical personnel in the operating room, to move the surgical robot 102 to different locations before, during, and/or after a surgical procedure. The mobile cart enables the surgical robot 102 to be easily transported into and out of the operating room 100. For example, a user 106a may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

In some implementations, the wheels include a locking mechanism that prevents the cart from moving. The stabilizing, braking, and/or locking mechanism may be activated when the machine is turned on. In some implementations, the mobile cart includes multiple stabilizing, braking, and/or locking mechanisms. In some implementations, the stabilizing mechanism is electro-mechanical with electronic activation. The stabilizing, braking, and/or locking mechanism(s) may be entirely mechanical. The stabilizing, braking, and/or locking mechanism(s) may be electronically activated and deactivated.

In some implementations, the surgical robot 102 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector. Registration spatially aligns the robot, patient (e.g., spine) and the desired trajectory. A marker may be coupled or associated with a vertebrae or other bone to assist with the registration process. The location of the marker is determined by the system. The system stores this position. The position of the vertebrae is thus known. The position of other bones may also be determined with reference to the marker. Once the registration is complete, tracking and/or immobilization ensure that the registration (e.g., spatial orientation) is maintained Immobilization typically fixes the patient or bone (e.g., spine) with respect to the robot. In contrast, tracking system tracks the position of the patient or the bone (e.g., by tracking the movement of the marker or position of the marker relative to the robot) as described in relation to FIGS. 1 and 3.

In some implementations, the surgical robot 102 includes a robotic arm comprising joints allowing the arm to be automatically positioned upon user command into various different predetermined configurations convenient for various preparatory, readying, and storage procedures. For example, the surgical robot 102 may be arranged in a standby configuration. In a standby configuration, the robotic arm of surgical robot 102 may be arranged in a compacted standby configuration that, for example, facilitates easy and compact storage of surgical robot 102 when it is not in use. Other configurations may include a drape configuration in which the robot arm is extended to facilitate placement of a sterile surgical drape over the robot and cart, and a preparation configuration in which the robot arm is positioned prior to movement to the operating table whereupon more precise movement of the robot arm will be performed for alignment of the trajectory of the end effector (surgical tool holder).

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, when the surgical robot 102 is powered on, robot 102 switches from the standby configuration to another configuration, e.g., a preparation configuration. In some implementations, preset positions of the robotic arm and the arrangement of each moveable portion of the robotic arm of surgical robot 102 may be stored in a memory of the surgical system.

In some implementations, the mobile cart includes a power source for powering the robotic system, including, for example, the actuator. The power source may include a battery and/or a battery backup. In some implementations, the mobile cart is charged and/or powered by an electrical socket in the operating room. The mobile cart may be capable of being powered by a battery on the cart and/or via an electrical outlet. In some implementations, power is provided via an electrical outlet during the surgical procedure. A battery may be used to provide power to the system when the system is being moved or in case of a power cut.

In some implementations, different elements of the surgical system work in tandem by communicating with each other wirelessly. In some implementations, a tracking detector 108 monitors the location of patient 104 and the surgical robot 102. The tracking detector may be a camera, a video camera, an infrared detector, field generator and sensors for electro-magnetic tracking or any other motion detecting apparatus. In some implementation, based on the patient and robot position, the display screen displays a projected trajectory and/or a proposed trajectory for the robotic arm of robot 102 from its current location to a patient operation site. By continuously monitoring the patient and robotic arm positions, using tracking detector 108, the surgical system can calculate updated trajectories and visually display these trajectories on display screen 110 to inform and guide surgeons and/or technicians in the operating room using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae or other part of the patient during the surgical procedure.

For safety reasons, the mobile cart is provided with a stabilization system that may be used during a surgical procedure performed with a surgical robot. The stabilization mechanism increases the global stiffness of the mobile cart relative to the floor in order to ensure the accuracy of the surgical procedure.

FIG. 2A-E illustrate an example stabilization system for stabilizing a mobile cart during a surgical procedure performed with a surgical robot. In some implementations, the global stiffness of the system is ensured by a combination of elements, such as the high rigidity of the internal rack 202, rigid legs 206, base plate 204, robot arm 208, tool holder 216 and surgical instrument 210.

As shown in FIG. 2A-B, a mobile cart 200, in some implementations, includes an internal rack 202. The internal rack may be mounted on a baseplate 204 that includes rigid legs 206. The internal rack may support the robotic arm 208 that holds tool 210 and/or provide a fastening interface for integrated components. The internal rack 202 may be made of profiled bars that are assembled by welding to provide a high stiffness. The internal rack may also be made using bent and welded sheet metal or casting. In some implementations, the internal rack is integrated with the base plate.

The baseplate 204 may be made out of melded aluminum and the legs 206 may be directly machined in the plate 204 to provide stiffness to the part. Mobile cart includes three rigid legs (206a-c), however, more or less rigid legs may be used. Rigid legs of different shapes and sizes may be used. In some implementations, a thin anti-sliding layer made out of, for example, rubber, is glued on the contact surface of the rigid legs 206 to ensure stability of the system on the floor even in the case of a lateral force applied to the system. The baseplate 204 may also protect the cart and robotic system from rough handling.

Figure 2C:
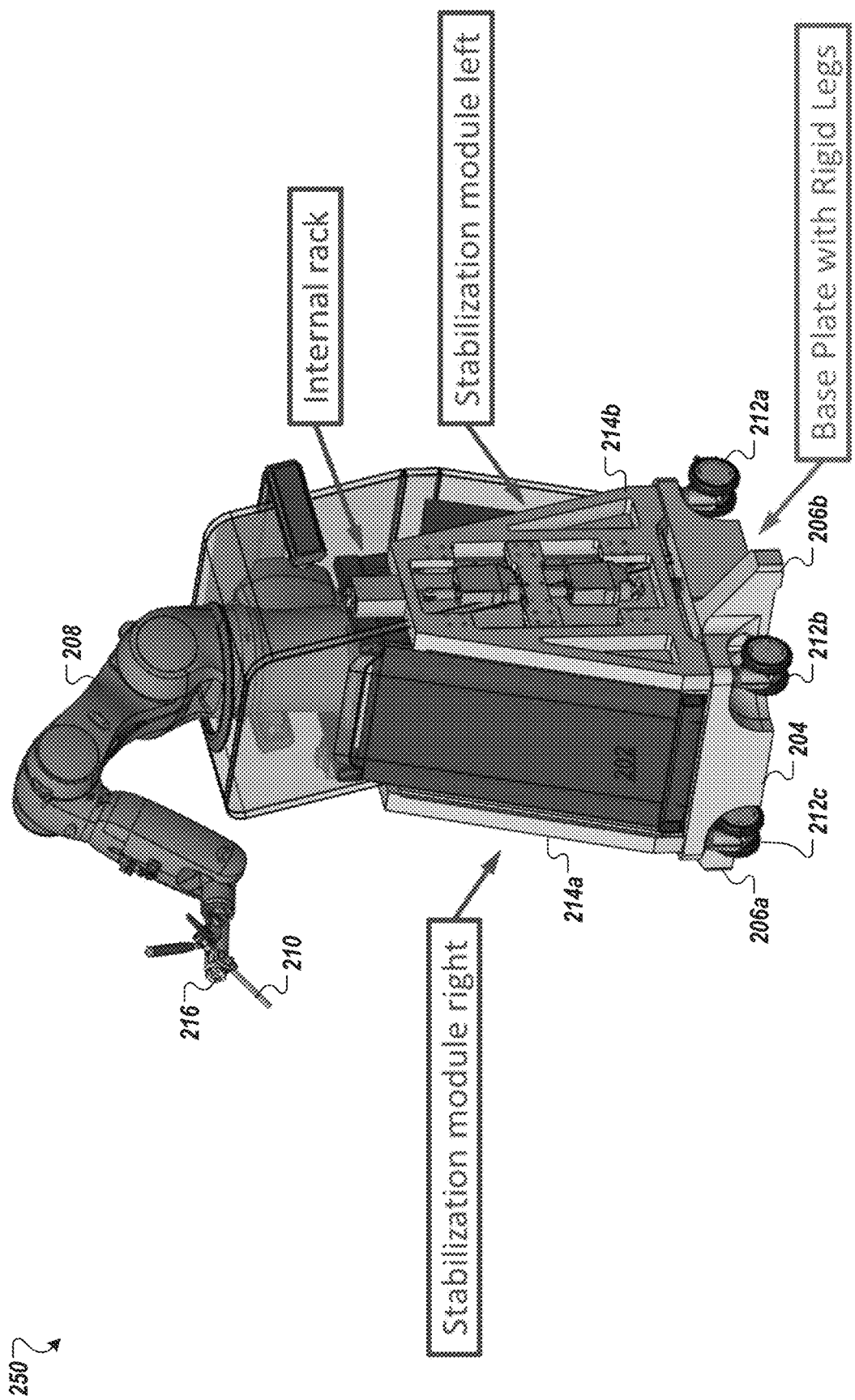

FIG. 2C illustrates a mobile cart 250 with extracting/retracting wheels 212 (e.g., casters). The mobile cart 250 is configured to use four wheels, although alternative arrangements may be used. The mobile cart 250 includes a stabilization module 214. The stabilization module includes a right 214a and left 214b side, each attached to the side of an internal rack 202. The stabilization system 214 enables system 250 to be moved up onto the wheels 212 allowing it to be rolled for positioning, moving, and storage. The stabilization mechanism 214 also lowers the system 250 onto rigid legs 206 to provide a stable platform during a surgical procedure.

Figure 2D:
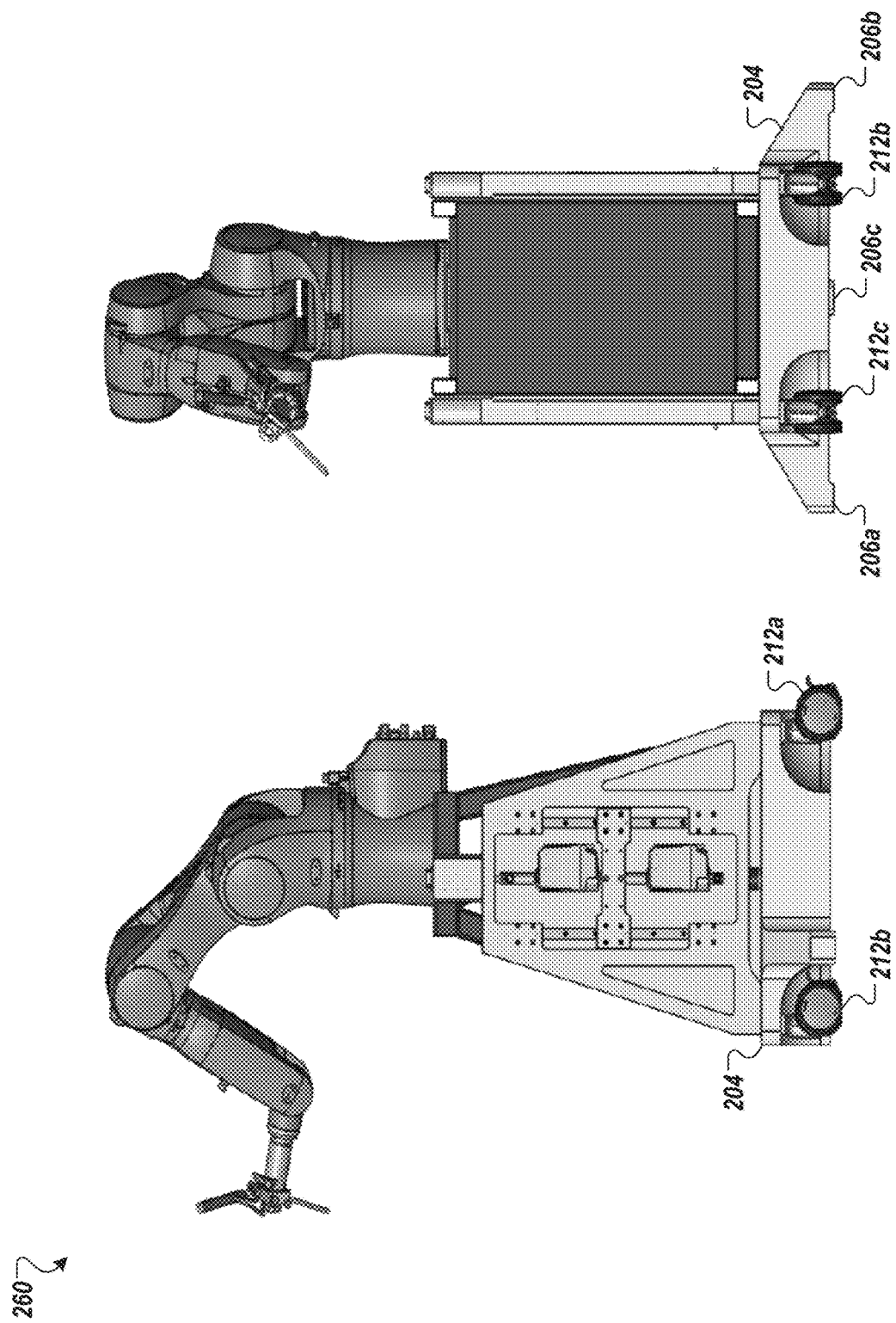
Figure 2E:
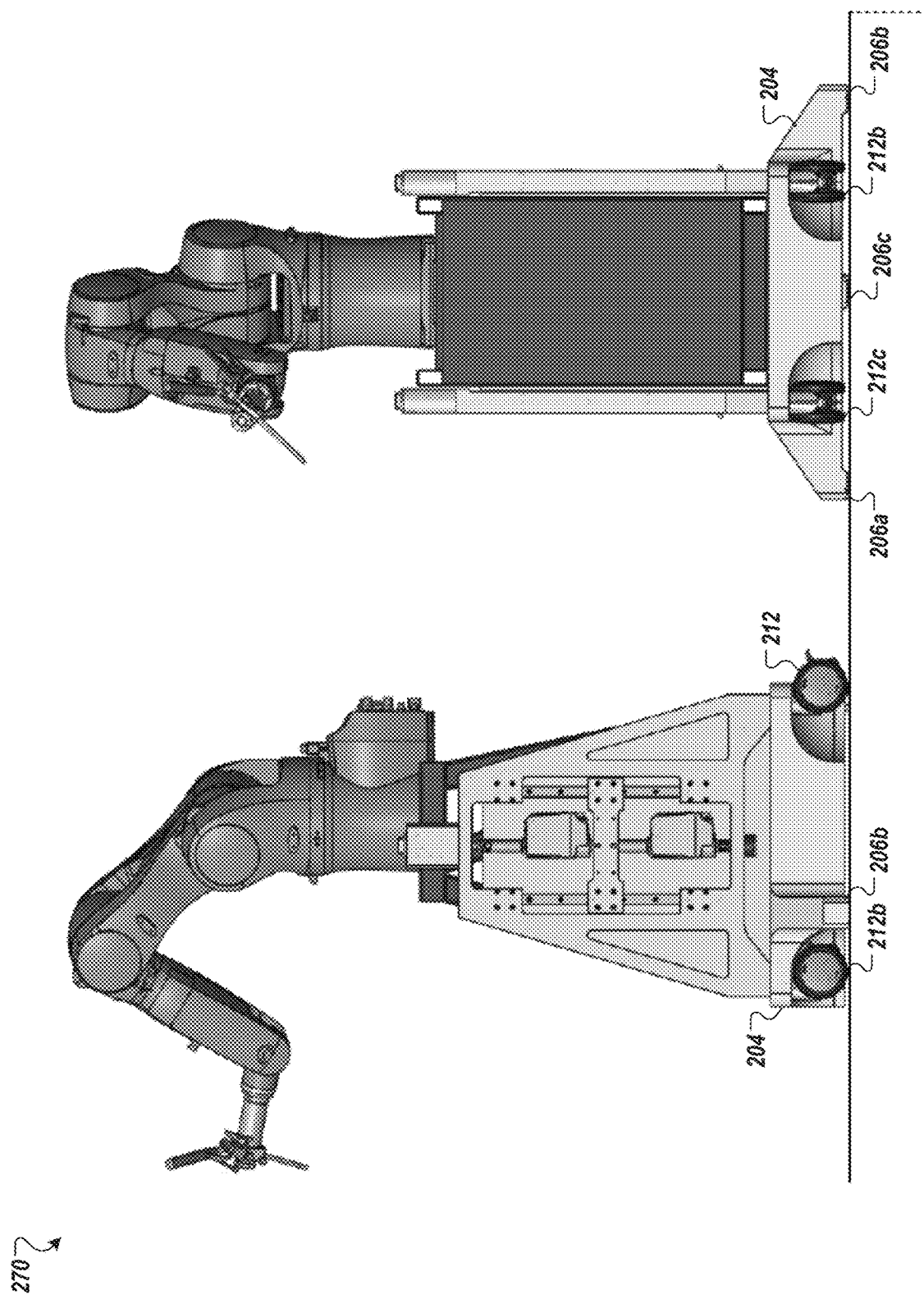

In some implementations, the wheels of the mobile cart are raised to lower the mobile cart such that the cart sits on its base when the wheels are fully raised. FIG. 2D illustrates an example system 260 (shown in two views) with the wheels 212 extended to provide a riding state. The system 260 is positioned on wheels 212 (e.g., casters) and can be moved from room to room. When the robot is moved into position for an operation, the wheels 212 may be retracted. FIG. 2E illustrates an example mobile cart 270 (shown in two views) with the wheels 212 retracted. The wheels 212 may be retracted by hydraulics, an electric motor, or other similar system. When the wheel 212 are retracted, the mobile cart sits on legs 206 of the base plate 204 and is stabilized on the operating room floor.

In some implementations, the mobile cart includes a stabilizing, braking, and/or locking mechanism for preventing movement of the mobile cart upon engagement of the mechanism. In some implementations, one or more members may be lowered to raise the mobile cart off the wheels. In some implementations, both one or more members are lowered and the wheels are raised to stabilize the mobile cart for operation.

Figure 3:
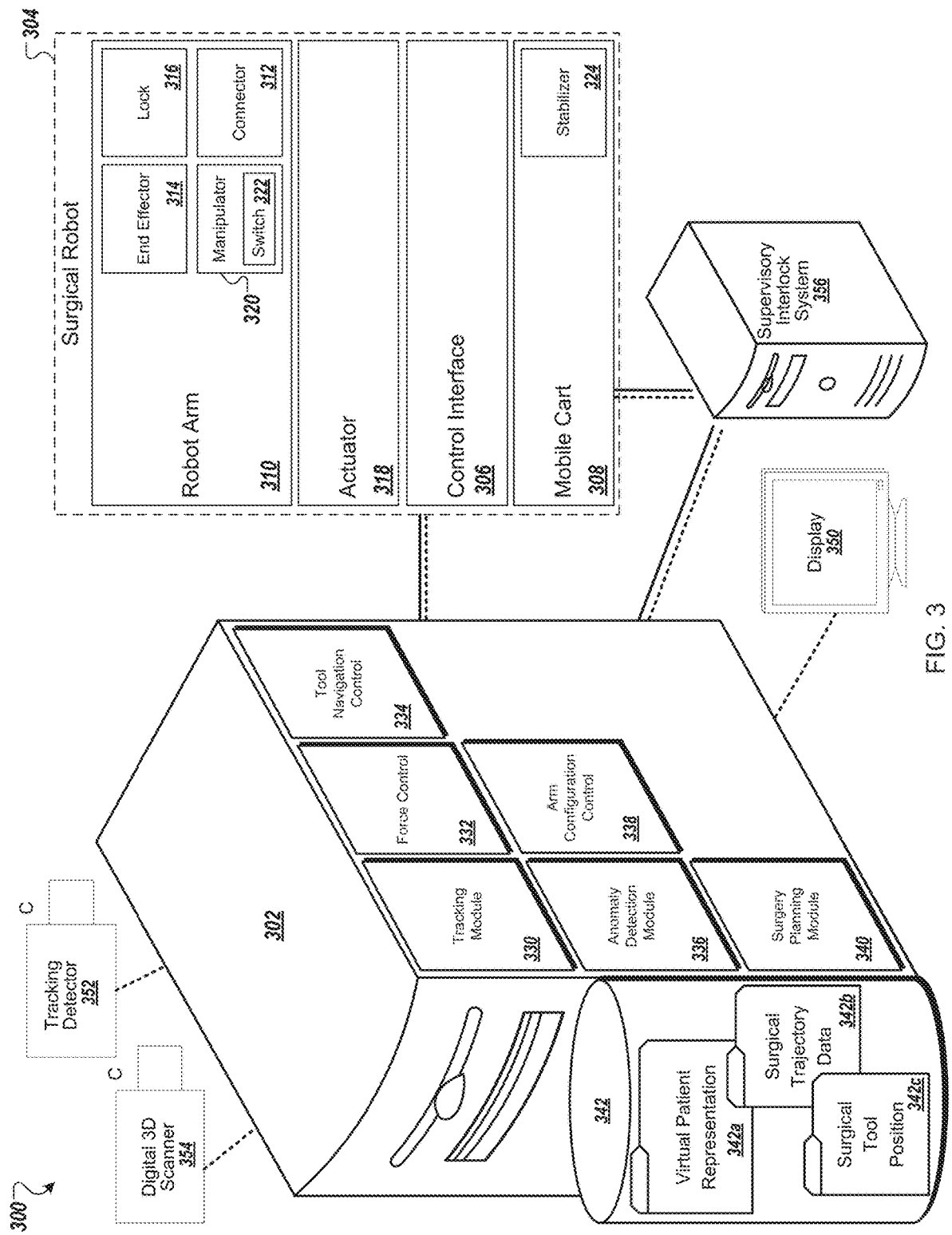
FIG. 3 is a block diagram of an example system for performing robotic-assisted surgical procedures, in accordance with various embodiments of the disclosed technology.

FIG. 3 illustrates an example of a surgical system 300 for performing robotically assisted surgeries. As illustrated in FIG. 3, surgical system 300 may include a computing system 302, a memory unit 342, a surgical robot 304, a supervisory interlock system 356, a display 350, a tracking detector 352, and/or a digital three dimensional scanner 354. In some implementations, surgical robot 304 corresponds to surgical robot 102 of FIG. 1, whereas display 350 and tracking detector 352 correspond to display 110 and tracking detector 108 of FIG. 1, respectively.

In some implementations, surgical robot 304 includes a control interface 306, also referred to as a control panel, that receives commands entered by an operator of the surgical robot 304 to control operation of the surgical robot 304. Surgical robot 304 may include a mobile cart 308 on which the control interface 306, robot arm 310 and other hardware components of surgical robot 304 rest. The robotic arm 310 includes several components such as a connector 312 and/or an end effector 314 (e.g., tool holder). The moveable components of robot arm 310 can change position and orientation with respect to one another to place the robot arm 304 into various different preset configurations. The robot arm 310 also includes a locking mechanism 316 that, when triggered by either computing system 302 or supervisory interlock system 356, locks movement of all of the moveable components of robot arm 310. In some implementations, the locking mechanism is mechanically and/or electrically activated. The locking behavior may be obtained by using a mechanism of the robot actuator or robot arm with the appropriate mechanism, such as non-backdrivable gears. Surgical robot 304 includes an actuator 318 that controls movement of robotic arm 310 and positions the end effector 314 according to commands received from computing system 302 of surgical system 300. Manipulator 320, which may be attached to robot arm 310 directly or indirectly through intermediate structures, allows for robotically assisted or unassisted positioning and movement of the end effector 314 by an operator of surgical robot 304. In some implementations, a robot controller controls the actuator 318. The computing system 302 may be responsible for navigation related tasks while the robot controller is responsible for robot related tasks (e.g., force control, arm configuration control, collision avoidance, robot workspace calculations, etc.).

Computing system 302 controls the surgical system 300 and processes implemented by the various components of system 300. Computing system 302 may include more than one processor. The computing system 302 may be a processor or a computing device, such as a mobile phone, tablet, desktop computer, laptop computer, server, or other computing device. Computing system 302 receives input data from the tracking detector 352, digital three dimension scanner 354, various hardware components of surgical robot 304, and/or the supervisory interlock system 356. It may process such input data to implement functions that allow for robotically assisted surgeries. Computing system 302 communicates with memory 342 to store and retrieve data at various stages of the surgical process. The computer system 302 may communicate with supervisory interlock system 356 to determine whether to suspend all or most of the processes run by various components of surgical system 300 upon detection of an anomaly. In some implementations, the supervisory interlock system 356 detects anomalies. The supervisory interlock system 356 may determine whether an anomaly has occurred using anomaly detection module 336. Upon detection of an anomaly, the supervisory interlock system 356 and/or computing system 302 may coordinate a shutdown of various components of surgical robot 304.

In some implementations, the computing system 302 generates a patient map based on data received from digital three dimension scanner 354. It may calculate trajectories for various components of robot arm 310. The computing system 302 may command display 350 to display the calculated trajectories, patient images, three dimensional maps of the patient surgical site, and/or other information. Warnings may also be communicated to surgeons and operators of the surgical robot 304. The display of such information in display 350 may be updated in real time during a surgical procedure as the robot arm 310 moves. The display of such information on display 350 allows surgeons to perform hands on surgical planning in the operating room and move the robot arm 310 using information displayed on display 350.

In some implementations, such as the one illustrated in FIG. 3, supervisory interlock system 356 is a processor that is located separately from computing system 302 and surgical robot 304. In some implementations, the supervisory interlock system 356 communicates with computing system 302 and surgical robot 304 wirelessly over a wireless network or via an industrial bus. In some implementations, supervisory interlock system 356 is part of the surgical robot 304 and is connected to surgical robot 304 through a wired connection. In some implementations, supervisory interlock system 356 is performed on computing system 302 or is connected to computing system 302 and is connected to computing system 302 through a wired connection. The supervisory interlock system 356 may control a software or firmware layer of various components of surgical robot 304 in order to immediately suspend operation of processes implemented by such components. Such components of surgical robot 304 may implement processes as commanded by computing system 302 until they are disabled by one or more commands received from the supervisory interlock system 356.

In some implementations, supervisory interlock system 356 is a processor that controls the firmware of surgical robot 304 to cause all hardware components of surgical robot 304 to stop moving and lock into their current position. Supervisory interlock system 356 may receive an indication that an anomaly in the surgical process has occurred from anomaly detection module 336. Such an anomaly may include a surgical emergency or a surgical complication that requires surgical robot 304 to halt its processes in order to avoid further intensifying the surgical anomaly. Other examples of anomalies include a hardware error, software error, or usage error. In response to receiving an anomaly indication signal from anomaly detection module of computing system 302, supervisory interlock system 356 may send a command to mobile cart 308, robot arm 310, tool holder 312, end effector 314, and/or manipulator 320 to become locked and/or resist any movement, even in response to external forces and/or torques applied on them. Supervisory interlock system 356 may execute a program, which can control the firmware of surgical robot 304 or on programs implemented on computing system 302 that control surgical robot 304, that provides instructions to halt movement of mobile cart 308, robot arm 310, tool holder 312, end effector 314, and manipulator 320. For instance, supervisory interlock system 356 may trigger a firmware interrupt on the firmware of surgical robot 304 or on programs implemented on computing system 302 that causes the processes running on the components of surgical robot 304 to pause and locks these components. Such locking of the mobile cart 308, robot arm 310, tool holder 312, end effector 314, and manipulator 320 to external forces and/or torques allows for an emergency braking mechanism to be implemented on surgical system 300 in case of an emergency or errors.

In some implementations, computing system 302 may be integrated into the surgical robot 304. For example, surgical robot 304 may have the processor on board that controls all of the features of the surgical robot, communicates and controls with the supervisory interlock system 356, display 350, digital three dimensional scanner 354, and tracking detector 352. In some implementations, each of these tasks may each be performed by an application specific processor. In some implementations, one or more processors performing these functions are located separately from the surgical robot 304. In some implementations, tasks performed by computing system 302 are performed multiple processors, that are located both on and off surgical robot 304, in tandem. In some implementations, the system includes a robot controller (such as robot controller) that is responsible for robot related tasks (e.g., force control, arm configuration control, collision avoidance, robot workspace calculations, etc) and a processor for navigation related tasks.

In some implementations, tracking detector 352 provides real-time detection of a surgical robot position and patient position. The tracking detector may include one or more camera, a video camera, an infrared detector, or any other motion detecting apparatus. As illustrated in FIG. 1, a tracking detector may be positioned over the operating table on which the patient is resting during a surgical procedure. In an embodiment, tracking detector 352 can identify different surgical tools and parts of the patient body. For example, tracking detector may include a motion detection apparatus coupled to a processor that can resolve the captured images or video to identify and motion track the patient's position (e.g., position of one or more organs, vertebrae, bones, organic tissue, veins, nerves, etc.) and surgical robot position (e.g., position of one more of end effector 314, tool holder 312, and a surgical tool). In another embodiment, tracking detector 352 can track, in real time, the position of markers embedded on the patient and surgical robot 304 to track both patient position and robot position using image detection and tracking algorithms. Tracking detector 352 may detect the position of the surgical robot and the patient in free space or with relation to each other. The tracking detector 352 may detect the position of other surgical tools and objects used in the operating room. Tracking detector may communicate surgical robot and patient position to computing system 302 wirelessly over a wireless network. Computing system 302 may store the surgical robot and patient position in memory 342 as surgical tool position data 342c and virtual patient representation data 342a, which are used, by computing system 302, to calculate the trajectory of tool holder 312 and end effector 314.

In some implementations, digital scanner 354 records images of the patient to create a virtual patient representation. In some implementations, the digital scanner 354 is a three dimensional scanner. In some implementations, the digital scanner 354 captures two dimensional images. Two dimensional images may be captured from, for example, fluoroscopy. Digital scanner 354 may be a medical imaging device such as a computer tomography scanner, a magnetic resonance image scanner, a nuclear magnetic resonance image scanner, an ultrasound machine, a photoacoustic imager, cardiac sonographer, a thermographic camera, a tactile imager, a 3D fluoroscopy device, or the like. Digital scanner 354 generates a three dimension virtual image of the patient and transmits such a virtual image wirelessly to computing system 302. Computing system 302 may store such a virtual image as virtual patient representation data in memory 342. Computing system 302 may display such a three dimension virtual patient representation on display 350 during a surgical procedure in conjunction with the calculated trajectories of the robotic end effector and surgical tool.

Display 350 may be a display screen in an operating room that displays the virtual patient representation and a calculated trajectory of the surgical tool, tool holder, or robotic end effector for the surgical process. Display 350 is a display device (e.g., a CRT (cathode ray tube) or LCD (liquid crystal display) monitor). In some implementations, display 350 may be positioned above the operating table separate from surgical robot 304 and may receive, for display, real time images of virtual patient representation, surgical trajectory position, and surgical tool position from computing system 302 wirelessly over a wireless network. In some implementations, display 350 is integrated into the surgical robot 304 and may be mounted on mobile cart 308. The display may a flat panel display such as LCD display, plasma display, LED display, or a wearable display (e.g., a display on glasses), holographic display, or a rendering directly on a patient's anatomy.

In some implementations, the surgical robot 304 rests on mobile cart 308. The mobile cart 308 is a housing with one or more wheels or a continuous track propulsion system. In some implementations, a handle is attached to or embedded in the housing of mobile cart 308 for locomotion of the mobile cart by an operator. In some implementations, the mobile cart may include stabilizing 324, braking, and/or locking mechanism to prevent movement of the mobile cart upon engagement of surgical robot 304. Such a mobile cart containing the surgical robot, allows surgical robot 304 to be near the operating table without being attached to the operating table, thereby providing maximum operating area and mobility to surgeons around the operating table and reducing clutter on the operating table. The stabilizing 324, braking, and/or locking mechanism allow the robot to be fixed during a surgical procedure and prevents any accidental movement or slippage of surgical robot 304 during a surgical procedure. Placing surgical robot 304 on a mobile cart allows for easy transportation and storage of the surgical robot.

In some implementations, the control interface 306 of surgical robot 304 provides an operator with a simple user interface to control surgical robot 304. Control interface 306, as discussed below in relation with FIG. 9 and FIG. 19, includes a switch to power on the device, switches to set robot arm 310 into a preset configuration, a switch to toggle between a force control mode and active holding position for surgical robot 304. Control interface 306 also displays which preset configuration surgical robot 304 is in and displays the operation status of surgical robot 304 (i.e., whether surgical robot 304 has malfunctioned). An error code may be displayed to identify a malfunction. Errors and faults may be divided into recoverable and non-recoverable errors and faults. This information may also be displayed to a user. Control interface 306 may consist of virtual switches (e.g., a graphical user interface with a touchscreen input), pushbuttons, rotary or toggle switches, a footswitch, or a another form of a tactile switch. In an implementation, the control interface 306 includes less than fifteen touch sensitive printed buttons to provide a simple uncluttered user interface to the operator, allowing for ease of use. The control interface may be a touch screen, voice control, movement (e.g., hand control) or visual-based gesture control, standard computer inputs such as a mouse and keyboard, or other similar input devices.

In some implementations, robot arm 310 is a programmable mechanical arm comprising several moveable parts. The robot arm 310 includes an end effector 314 to hold a surgical tool, a connector 312 that connects the end effector to the rest of the robot arm 310, and a lock 316 that, when activated by computing system 302 or supervisory interlock system, prevents movement of robot arm 310. In some implementations, the robotic end effector 314 is attached indirectly to a manipulator 320 that allows robotically-assisted or unassisted positioning movement of the end-effector 314 by a user with at least four degrees of freedom. Robot arm 310 is also attached to an actuator that controls movement of the robotic arm and positioning of the end effector 314. End effector 314 can position a surgical tool accurately and guide movement of the surgical tool. End effector 314 is configured to releasably hold a surgical tool and allows the surgical tool to be removed and replaced with another tool without re-registration or with automatic or semi-automatic re-registration of the end-effector position.

In some implementations, manipulator 320 is a handle attached directly or indirectly to the end-effector configured to allow robotically-assisted or unassisted positioning and movement of the end-effector by a user with at least four degrees of freedom. For example, the manipulator may allow robot arm to move with six degrees of freedom (i.e., three translations and three rotations). In some embodiments, the robot arm is capable of movement of the end-effector 314 in 2, 3, 4, 5, or 6 degrees of freedom. The end-effector may be placed in various modes including a translations only mode or a rotations only mode. In some implementations, the manipulator 320 is a serial manipulator. In some implementations, manipulator 320 is a part of end-effector 314 itself.

In some implementations, the manipulator 320 may be a sterile handle. The manipulator 320 may detect the presence of a user's hand. This ensures the end-effector is only moved when the user manipulates the sterile handle and reduces the likelihood that the end-effector is moved unintentionally. For example, robotic surgical system may permit the movement of the end-effector only in circumstances when the presence detector is activated (e.g., a hand of a surgeon is detected as present because the surgeon is holding the sterile handle). In some implementations, the manipulator 320 comprises one or more sensors configured to detect a presence of a surgeon's hand in proximity to the sterile handle. In some implementations, the one or more sensors include a presence mechanism that is engaged by a surgeon's hand when the surgeon holds the manipulator 320 such that presence of the hand is detected. The presence mechanism may be a lever-button mechanism. In some implementations, the presence mechanism includes one or more capacitive or resistive sensors, or a combination thereof.

Manipulator 320 may include a switch 322 that is activated by two buttons. When both buttons are simultaneously pressed, the manipulator can be moved. In some implementations, only when both buttons are pressed together is the manipulator 320 movable. Simultaneous pressing of two buttons, or other deliberate physical manipulation of a switching mechanism reduces the risk of accidental movement of the robotic end effector 314 due to an accidental button press.

In some implementations, for example, in some embodiments, the operator must activate switch 322 in order to place the robot arm 310 into force control mode. Once surgical robot 304 is placed in force control mode, the robot actuator 318 will allow controlled movement of the end effector 314 in response to a force applied on the robotic manipulator 320 or on the end effector 314.

In some implementations, a user may select to enter a translation mode, positioning mode, axis rotation mode, axis insertion mode and/or axis position mode. In some implementations, the manipulator includes an enabling button, rotation button and a translation button. In some implementations, the enabling button must be selected with one or more other buttons to enable movement of the end effector. For example, to rotate the end effector, the user may need to select the enabling button and the rotation button. Similarly, to enable translations of the end effector, the user may need to select the enabling button and the translations button. In some implementations, the end effector may enter a course positioning mode when a user selects the enabling button, translations button, or rotations button. In some implementations, selection of the enabling button causes the robotic arm to enter the positioning mode in which the user is able to position the tool appropriately and allows the operator to freely move the robotic arm (e.g., via course movements).

Selection of the translation mode allows the end effector to be purely translated (e.g., along a plane in line with the end of a tool such as a drill guide). An operator may use the translation mode to make fine movements with the end effector and to find an entry point. Selection of the rotation mode locks movement of the end effector except rotations (e.g., the manipulator may only be rotated). In some implementations, activation of the rotation mode permits an operator to make fine rotations around an entry point. In axis rotation mode an operator may rotate the end effector around a specific axis or point (e.g., the axis formed by a drill guide, vertebrae entry point). In axis position mode, an operator may move the end effector without changing an axis (e.g., the axis formed by a drill guide). In axis insertion mode, an operator may move the end effector along a trajectory.

The various positioning modes allow an operator to quickly and accurately move the end effector to a desired position (e.g., on or along a determined trajectory). When all of the buttons are released, in some implementations, the robot actively holds the position of the end effector. For example, if a drill guide is coupled to the end effector, an operator may insert a drill into the drill guide without moving the position of the end effector or drill guide. Thus, after carefully positioning the drill guide along a desired trajectory, an operator may accurately drill along the desired trajectory.

In some implementations, actuator 318 allows computing system 302 to move the end-effector upon receiving a force from the manipulator. Actuator 318 allows for controlled movement of the end-effector in the direction corresponding to the direction of application of force on the manipulator 320, at a predetermined measured pace. In some implementations, the actuator 318 moves the end effector 314 at a constant velocity. In some implementations, the actuator 318 moves the end effector 314 at a slow velocity. In some implementations, the actuator 318 moves the end effector 314 at a very slow velocity initially, and gradually increases the velocity gradually in a controlled manner to a greater velocity. In some implementations, actuator 318 moves the end effector 314 along a trajectory calculated by computing system 302. In another implementations, actuator 318 moves the end effector 314 in a manner such that the surgical tool position will be in alignment with the desired trajectory calculated by computing system 302. As described above, the surgical tool position may be moved along the trajectory and the configuration of the robotic arm may be changed without changing the trajectory of the surgical tool (e.g., using axis rotation mode and axis insertion mode).

In some implementations, computing system 302 tracks the position of the patient and the surgical tool, for example using tracking module 330. The computing system 302 receives images of the patient, surgical tool position, and end effector positions from tracking detector 352. In some implementations, images of the patient are received from a digital 3D scanner. Tracking module 330, for example, may calculate the position of the surgical tool and the patient in real time. In an implementation, tracking module 330 may track the position of the surgical tool and the patient in free space. In another implementation, tracking module 330 may track the position of the surgical tool and the patient with relation to each other. In an implementation tracking module 330 may identify, from the images received from the tracking detector 352, the portion of the patient to be operated on and the surgical tool and track these identified objects. In another implementation, tracking module 330 may track markers attached to the portion of the patient to be operated on and the surgical tool. Tracking module 330 may identify the markers from images received from tracking detector 352 and identify that these markers are attached to the patient and to the surgical tool and accordingly, track the patient position and surgical tool position.

In some implementations, computing system 302 determines a trajectory for the surgical tool, for example using surgery planning module 340. In some implementations, the surgeon determines the trajectory in an operation mode. The surgeon may record the trajectory by drawing on the virtual patient representation displayed on touchscreen of display 350 in hands on planning mode in the operating room. Surgery planning module 340 may be configured to accept surgeon identified trajectories in hands on planning mode. In some other implementations, surgery planning module 340 may calculate a trajectory using the virtual representation 342a of the patient situation stored in memory 342 and the surgical tool position 342c and store the calculated trajectory as surgical trajectory data 342b in memory 342. Surgery planning module 340 may also display the trajectory on display 350, superimposed on the virtual patient representation or in a separate screen to guide the surgeon as he positions the robotic manipulator 320.

In some implementations, computing system 302 controls actuator 318 to move the end effector 314 in a controlled manner, for example using tool navigation control 334. Tool navigation control 334 may detect a force applied to the manipulator 320 and determine whether the force exceeds a predetermined minimum force. In some implementations, the tool navigation control 334 communicates with a sensor that detects forces (i.e., forces and/or torques) applied to the manipulator 320 and the tool navigation control 334 determines whether the force exceeds a predetermined minimum force. If the detected force applied to manipulator 320 is determined to exceed a predetermined value stored in memory 342, tool navigation control 334 may control the actuator 318 to move the end effector 314 at a measured pace along a calculated desired trajectory (i.e., surgical trajectory data 342b). This functionality may also be implemented using sensors and signal processing implemented before the processor. Comparing the force applied to the manipulator against a predetermined minimum force provides impedance control and provides resistance to accidental small movements. In some implementations, the predetermined minimum force may be zero.

In some implementations, computing system 302 controls the actuator to place the end effector in force control mode or in an active holding position, for example using force control 332. When surgical robot 304 is placed in force control mode, the actuator 318 is allowed to translate the end-effector 314 an identified distance in an identified direction (e.g., move the end-effector by 1 mm in a given direction) and to adjust an angle of rotation of the end-effector (e.g., adjust the roll, yaw, or pitch by 0.1 degree). However, in some implementations, when surgical robot 304 is placed in an active holding position, force control 332 activates lock 316 and prevents the actuator from moving the end effector regardless of the amount of force applied to manipulator 320 or any other part of the surgical robot 304. In some implementations, the active holding position does not activate a lock and instead the robot controller monitors the position of the end effector and instructs the actuator to compensate actively (e.g., using axis motors) for movement's out of the pre-defined position. This improves rigidity as active motors are used instead of passive brakes. Once force control 332 places surgical robot 304 in active holding position, the tool guide attached to the end effector will be held in position and the surgeon can manipulate the tool within the tool guide that is fixed in position to prevent the surgeon from accidentally straying off the optimum patient position for the surgical procedure.

In some implementations, computing system 302 detects whether there is an anomaly or an accident during the surgical procedure, for example using anomaly detection module 336. The anomaly detection module 336 may be implemented on the robot controller and/or supervisory interlock system. Anomaly detection module 336 may continuously monitor the images from tracking detector 352 to determine if an anomaly exists. In another implementation, anomaly detection module may monitor user press of an emergency stop switch on control interface 306. Other examples of anomalies that may be detected by the anomaly detection module are a surgical emergency, surgical complication, hardware or software errors, or usage errors. Once anomaly detection module has flagged an anomaly, computing system 302 sends an emergency signal to supervisory interlock system 356 to suspend all surgical robot movement.

In some implementations, computing system 302 controls the position of the robot arm to be in one of the preset arm configuration modes, for example using arm configuration control 338. Arm configuration control 338 may instruct the moveable components of robot arm 310 to move and orient themselves to be arranged in a predetermined arm configuration based on the arm configuration that an operator selects from control interface 306.

Figure 4:
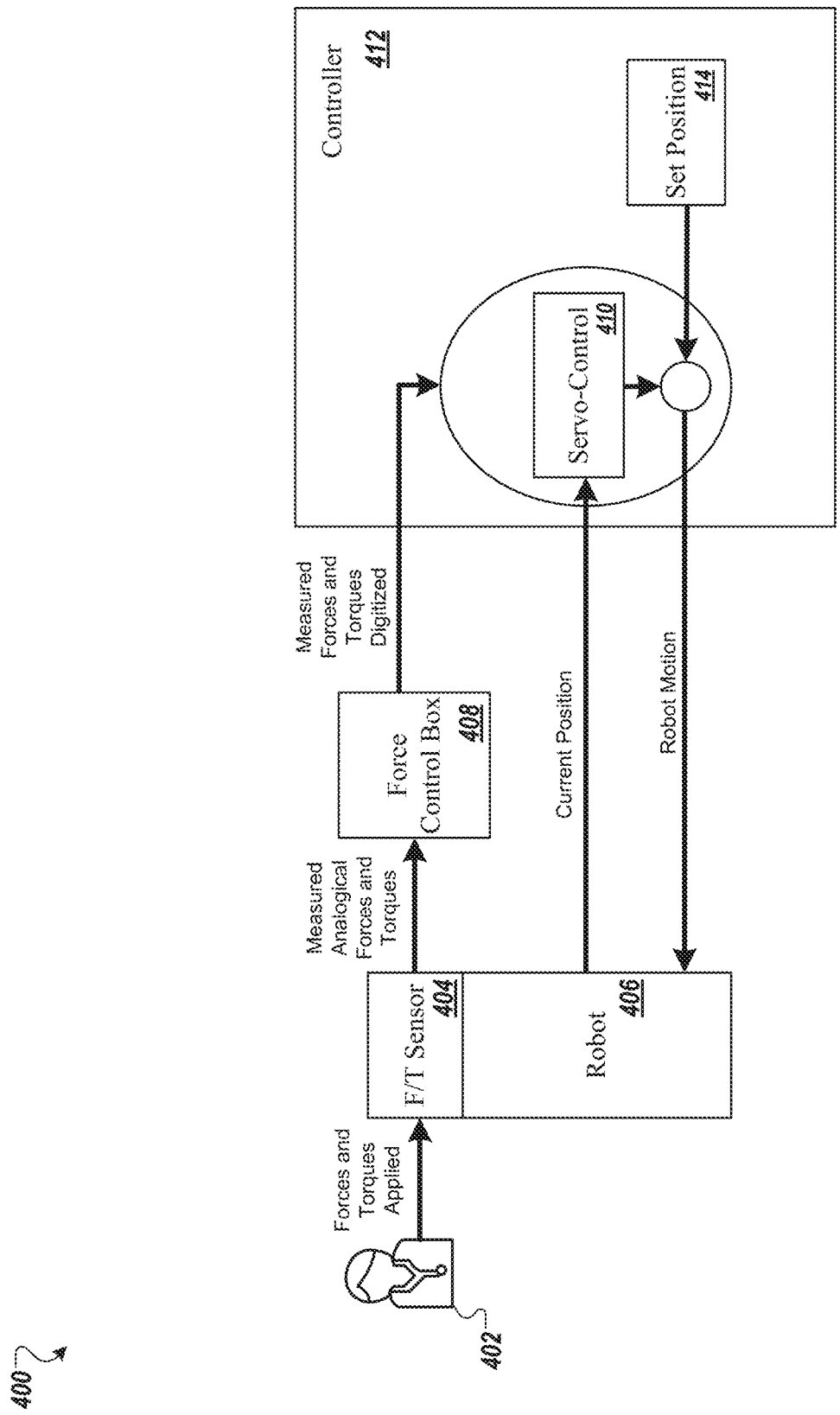
FIG. 4 is a diagram illustrating an example force control system.
Figure 5:
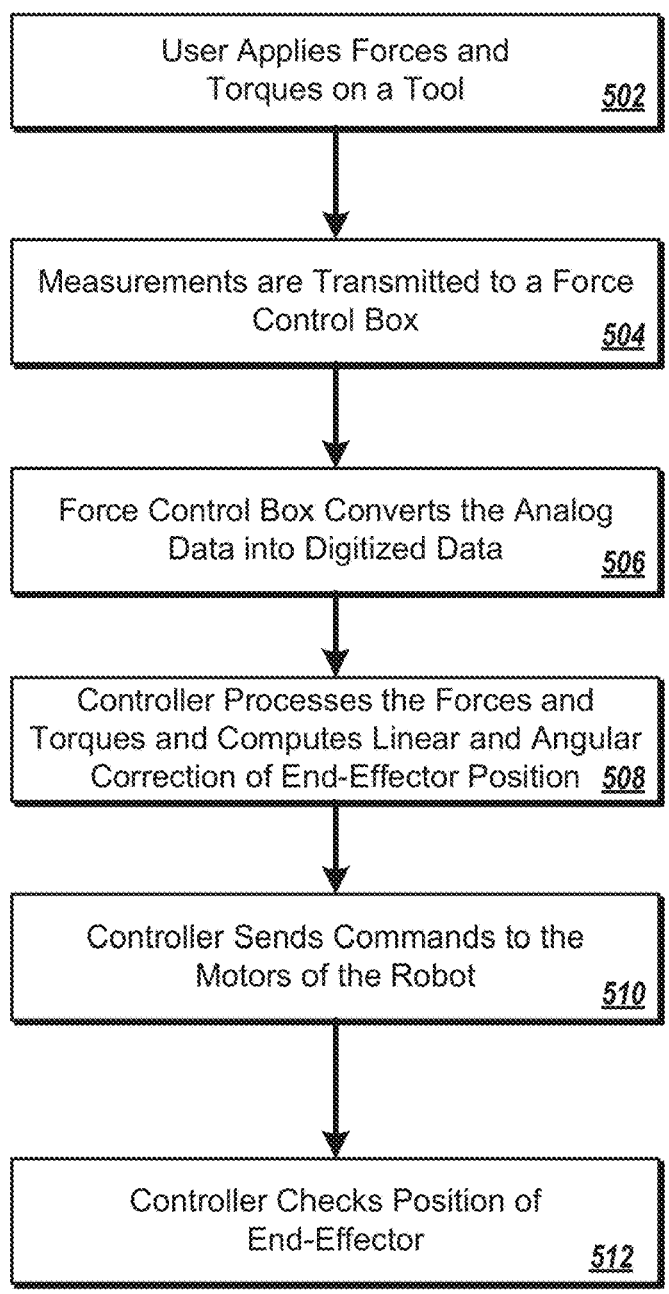
FIG. 5 is a flow chart describing an example method for using a force control system.

FIG. 4 illustrates an example force control system 400 and FIG. 5 illustrates an example method 500 of using a force control system. In some implementations, a user 402 applies forces and torques on a tool (step 502) attached to a force/torque sensor 404. The force/torque sensor may be attached to a flange on the robot 406 and measures the forces and torques applied to the tool. The force sensor may be attached to system in a variety of configurations, including the example configurations shown in FIGS. 6A-C. In some implementations, the measurements are transmitted to a force control box 408 (step 504). In some implementations, the force control box 408 converts the analog data into digitized data and transmits them to the controller 412 (step 506). In some implementations, the measurements from force/torque sensor 404 are sent directly to the controller 412. The controller 412 processes the forces and torques and computes linear and angular correction of the end-effector position of the robot (step 508). The controller 412 sends commands to the motors of the robot to update the position of the end effector to a setpoint position 414 (step 510). The controller may check the current position of the position of the end-effector (step 512) and stops sending commands to the motors if the setpoint 414 position is reached. In some implementations, this process is performed continuously. In some implementations, the motors are servo or electric motors that are controlled by a servo control 410.

Figure 6C:
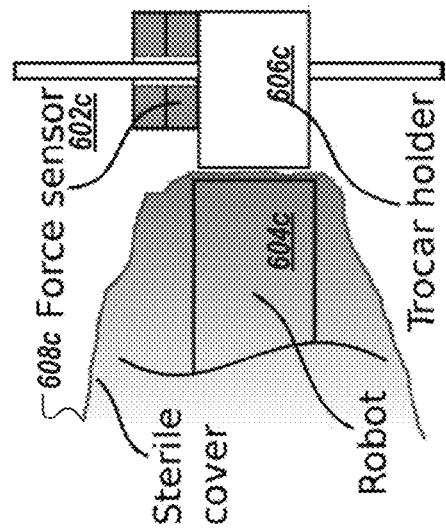
FIG. 6A-C are diagrams illustrating example locations for mounting a force sensor and sterile drape.
Figure 6B:
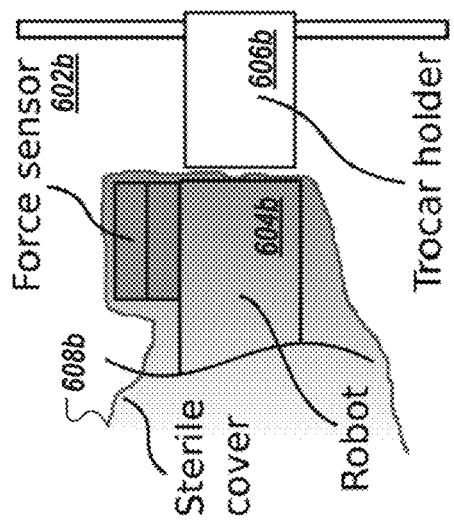
Figure 6A:
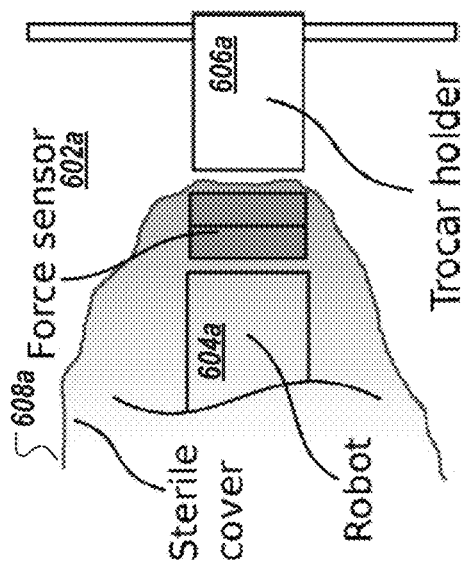

FIG. 6A-C illustrates example locations for mounting a force sensor (e.g., force/torque sensor 404). In some implementations, as shown in FIG. 6A, the force sensor 602a is located between the tool holder 606a and robot 604a. Using this configuration, the sterile cover 608a may be wrapped around the robot arm and between the force sensor and the tool holder to ensure sterilization. The force sensor 602a may provide for direct measurement of forces (e.g., forces and/or torques) on the tool. The force sensor 602a may be designed to resist flexing. The force sensor 602a may be designed to flex under the stress of certain external forces, The displacement caused when an external force is applied may be calculated based on the force and/or torque applied to the tool, torque applied to the tool, radial force stiffness, axial torque stiffness, and the diameter of the holder to which the tool is attached.

As shown in FIGS. 6B and 6C, respectively, the force sensor (e.g., 602b in FIG. 6B or 602c in FIG. 6C) may be located on the robot or the tool holder. These configurations may exclusively measure the forces and/or torques applied by the user. The force sensor 608 may be connected to the robot with an intermediary analog box which measures forces and torques and transmits them via a network (e.g., Ethernet, CAN, wireless, internet, private LAN, public LAN, etc.). Combinations of the above mentioned force sensor positions are possible to achieve pre-defined behavior (e.g. the first sensor in the base FIG. 6A and the second one in the handle FIG. 6B may be positioned to allow the feedback control system to decouple forces applied to the surgical tool from forces and/or torque applied by a user).

Figure 7:
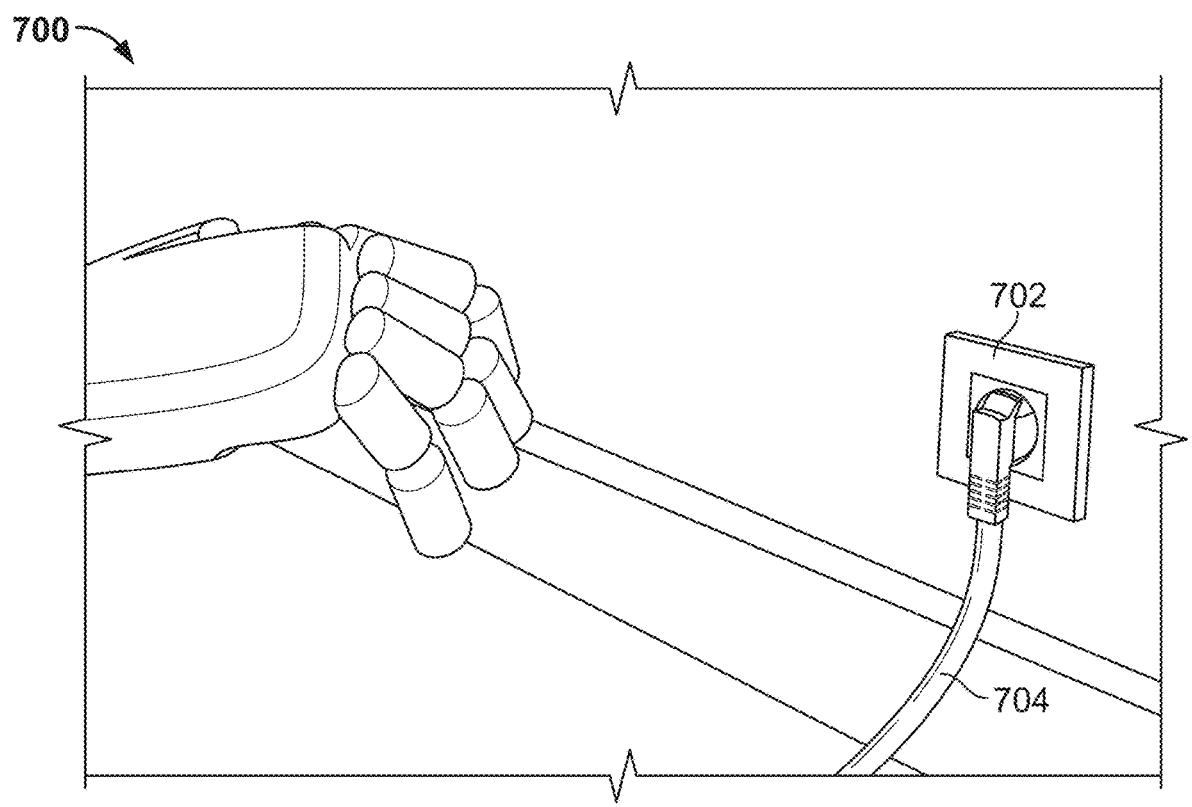
FIG. 7 is a diagram illustrating an example power source for the mobile robotic surgical system of FIG. 2, in accordance with various embodiments of the disclosed technology.

Starting from FIG. 7, an illustrative surgical process using the robotic surgical system is described. FIG. 7 illustrates a standard electrical outlet 702 which serves to charge the battery for the robot and/or serves as a power source or backup power source for the robot. Once an operator introduces the surgical robot into an operating room on its mobile cart, the surgical robot can be plugged into a power socket 702 to provide power, and/or the surgical robot may operate solely on battery and/or battery-backup power. The power source may be a conventional wall or floor power socket. The surgical robot may have a battery pack that is charged using a power plug 704 from a wall socket 702. Once the surgical robot is connected to the power socket 702 and/or once battery charging is complete, the operator powers on the surgical robot by pressing a power switch on the control panel of the surgical robot.

Figure 8:
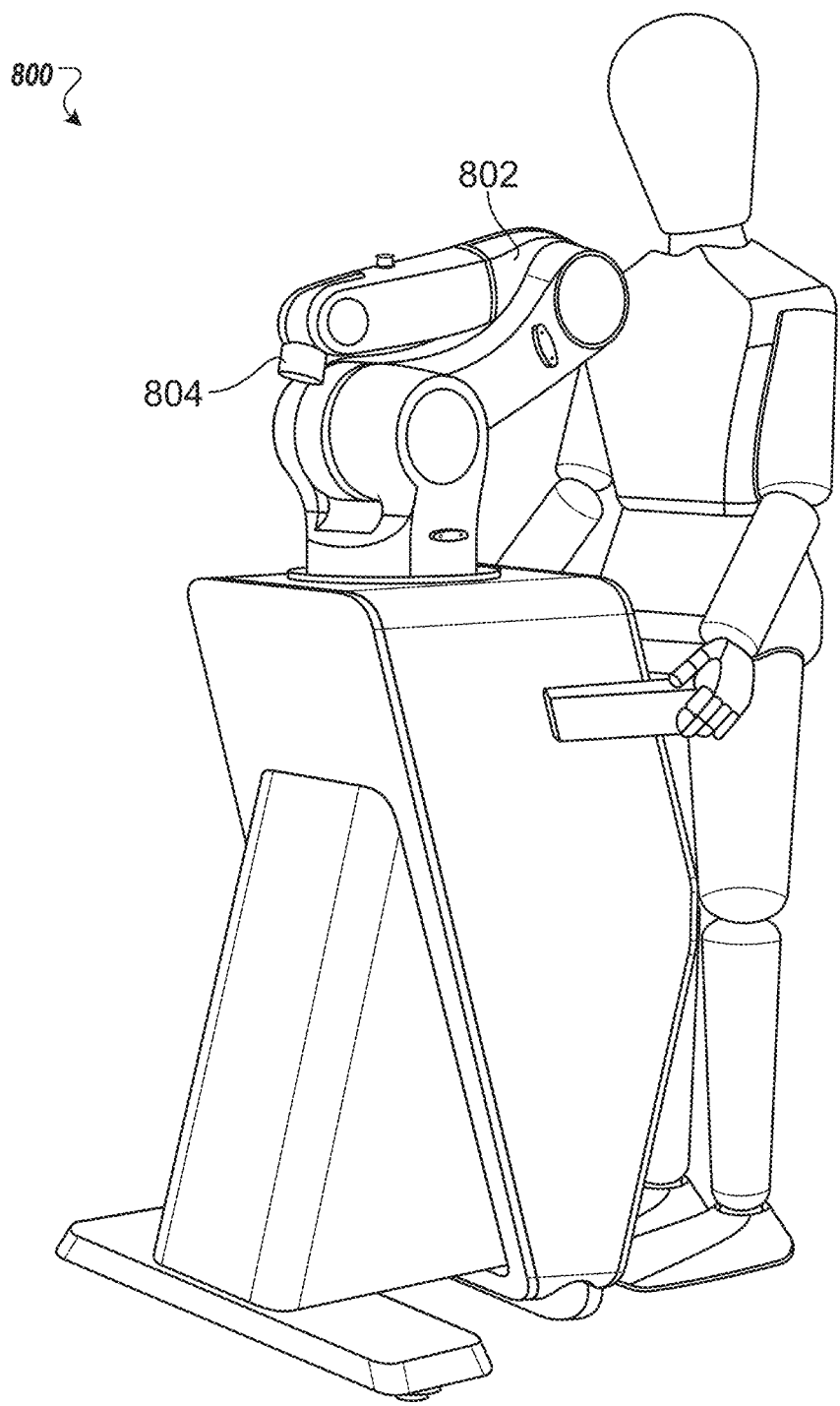
FIG. 8 is a diagram illustrating an exemplary configuration of a robotic system in standby mode, in accordance with various embodiments of the disclosed technology.

FIG. 8 illustrates an exemplary configuration of a robotic system in standby mode. Surgical robot 800 is initially configured to be positioned in standby mode as shown in FIG. 8. In some embodiments, the robotic arm 802 of the surgical robot is positioned in a folded and compact configuration, while in standby mode, without the robot arm protruding away from the mobile cart. This allows the surgical robot 800 to be stored in a compact manner. In standby mode, arm configuration control 338 of processor 302 shown in FIG. 3 may instruct the robotic arm 802 to position a connector 804 attached to the robotic arm 802 to be placed downwards. In standby mode, an end effector may not be attached to the robotic arm 802. When the robot 800 is placed into standby mode from another arm configuration mode, the robot arm connector 804 may release the end effector previously connected to it. Typically, the robot 800 is placed into standby mode at the very end of the surgical process prior to being powered off and stored. Once the surgical robot 800 is powered on by an operator using the control panel of the surgical robot, the operator can place the robot 800 into a different arm configuration using the control panel.

Figure 9:
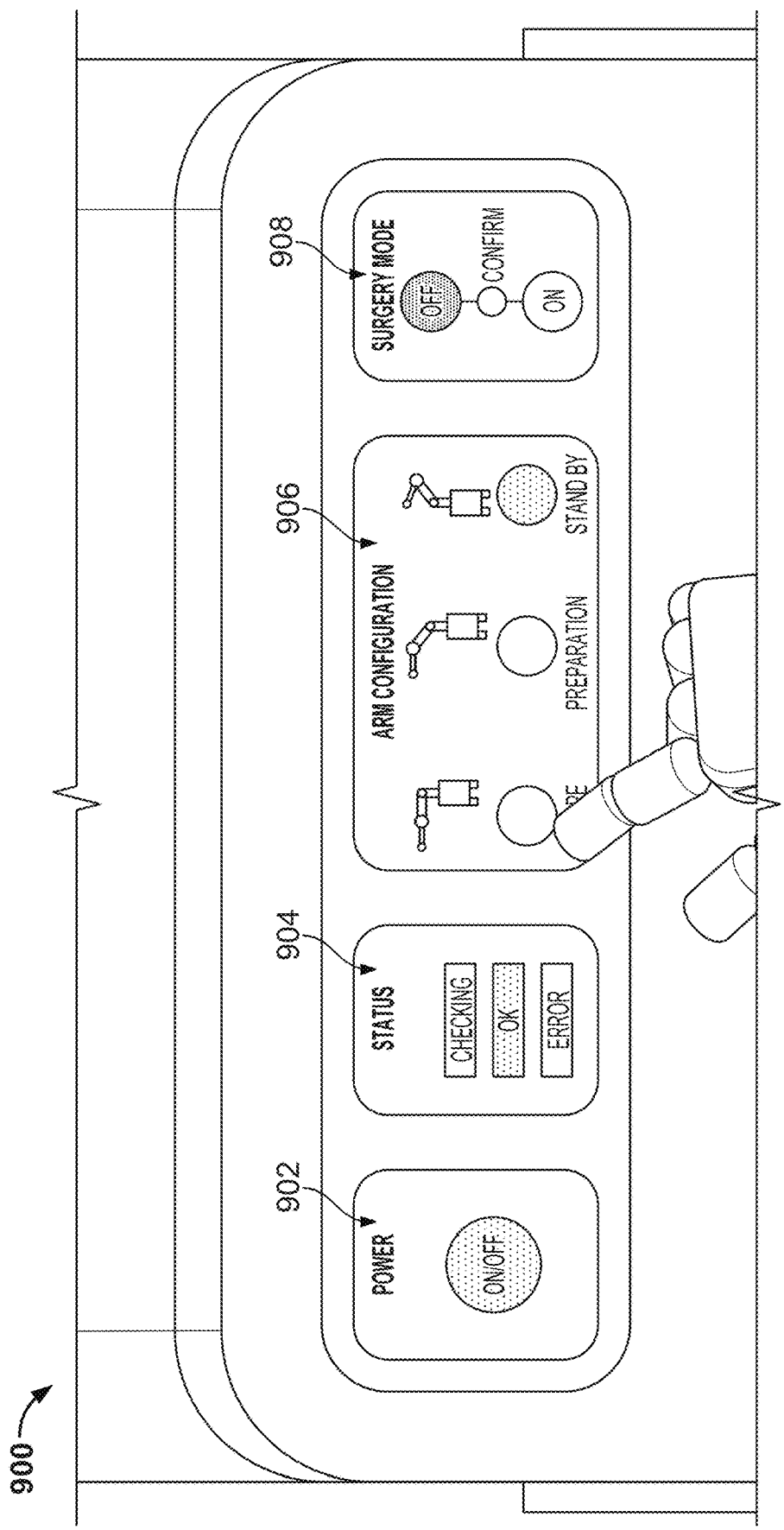
FIG. 9 is a diagram illustrating an example control panel of a robotic surgical system, in accordance with various embodiments of the disclosed technology.

FIG. 9 illustrates an example control panel 900 of a robotic surgical system. The control panel includes a power switch 902, a status display 904, an arm configuration subpanel 906 including switches for different preset arm configurations and surgery mode subpanel 908 including switches to place the surgical robot into surgery mode. Once the surgical robot is powered on, the surgical robot checks its operational status and reflects the status in the status display 904, by highlighting one of the status fields (i.e., checking status, OK, and Error). The error codes may be shown on a display. Once status check is completed, an operator may change the arm configuration of the surgical robot from a standby mode to drape mode by pressing the drape mode switch from the arm configuration subpanel 906 as shown in FIG. 9. Once the drape mode switch is toggled, for example, arm configuration control 338 of computing system 302 as shown in FIG. 3 instructs the surgical robot arm to arrange itself into a preset configuration known as drape mode in which the surgical robot can be covered in a sterile surgical drape. Similarly, an operator may change the robot arm configuration from drape mode into surgical preparation mode after the robot has been covered with the sterile drape by pressing the Preparation mode switch. In some implementations, the operator may activate surgery mode on the robot. In some implementations, the operator activates surgery mode by pressing an On button. A confirm button on the surgery mode subpanel 908 may light up once the On button is pressed once. Upon selection of the confirmation button by the operator (e.g., after selecting the On button), the system may enter a surgery mode. Requiring the operator to press the on button and confirm button reduces the risk of the robot being accidentally being placed into surgery mode as a result of an accidental button push. In some implementations, the operator may exit the operating mode by selecting an Off button and subsequently selecting of the confirmation button within a predefined time window (e.g., 10 seconds).

In some implementations, the display panel in FIG. 9 is a simple design, with relatively few buttons and/or indicators (e.g., no more than 20, no more than 15, or no more than 10). The buttons can be printed, permanent buttons, e.g., touch sensitive button switches, or other non-tactile, or tactile (physical) button switches. Some of the buttons may have graphical cues (e.g., the arm configuration buttons) and/or alphanumeric labels. Printed buttons do not require a special operating system to display them, and provide other advantages. The display panel may be a digital display with touch-sensitive buttons indicated by digital graphics rather than printed graphics. The control interface may be a touch screen, voice control, movement (e.g., hand control) or visual-based gesture control, standard computer inputs such as a mouse and keyboard, or other similar input devices.

Figure 10:
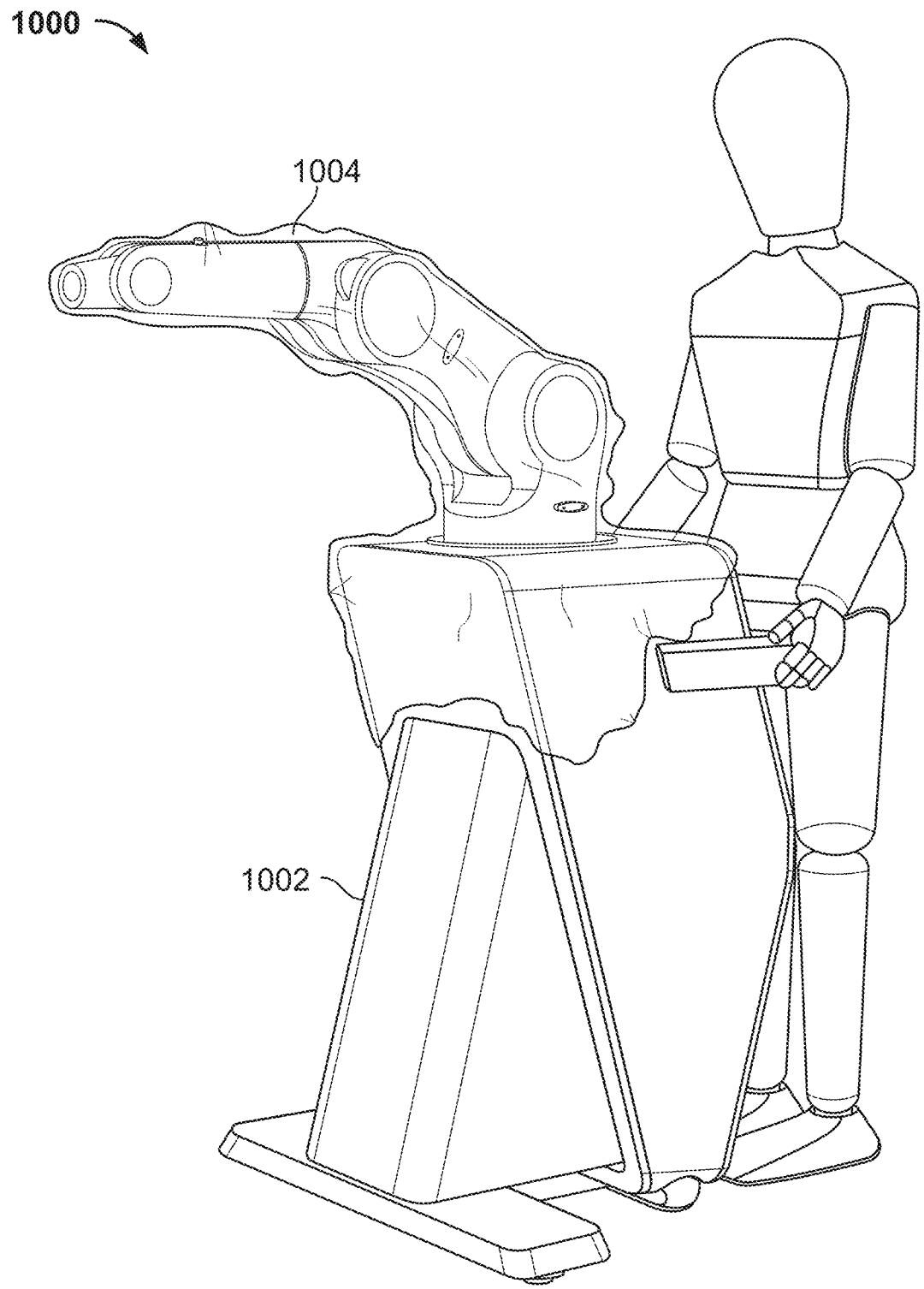
FIG. 10 is a diagram illustrating an exemplary configuration of a robotic system in a draping mode, in accordance with various embodiments of the disclosed technology.

FIG. 10 illustrates an exemplary configuration of a surgical robot 1000 in a draping mode. The arm configuration of surgical robot 1000 changes from a compact position in standby mode to one in which the robot arm protrudes away from the mobile cart 1002. In drape mode, the arm configuration of the surgical robot is arranged such that a sterile surgical drape 1004 can be easily placed on the robot 1000. In some embodiments, the sterile drape 1004 may cover all of the surgical robot body, including the entire mobile cart, robot arm, robot arm connector, and an end effector attached to the robot arm connector, thereby protecting the patient from exposure to non-sterile surfaces, dust, or other material originating from the robotic system, and protecting the equipment from surgical waste and fluids.

Figure 11:
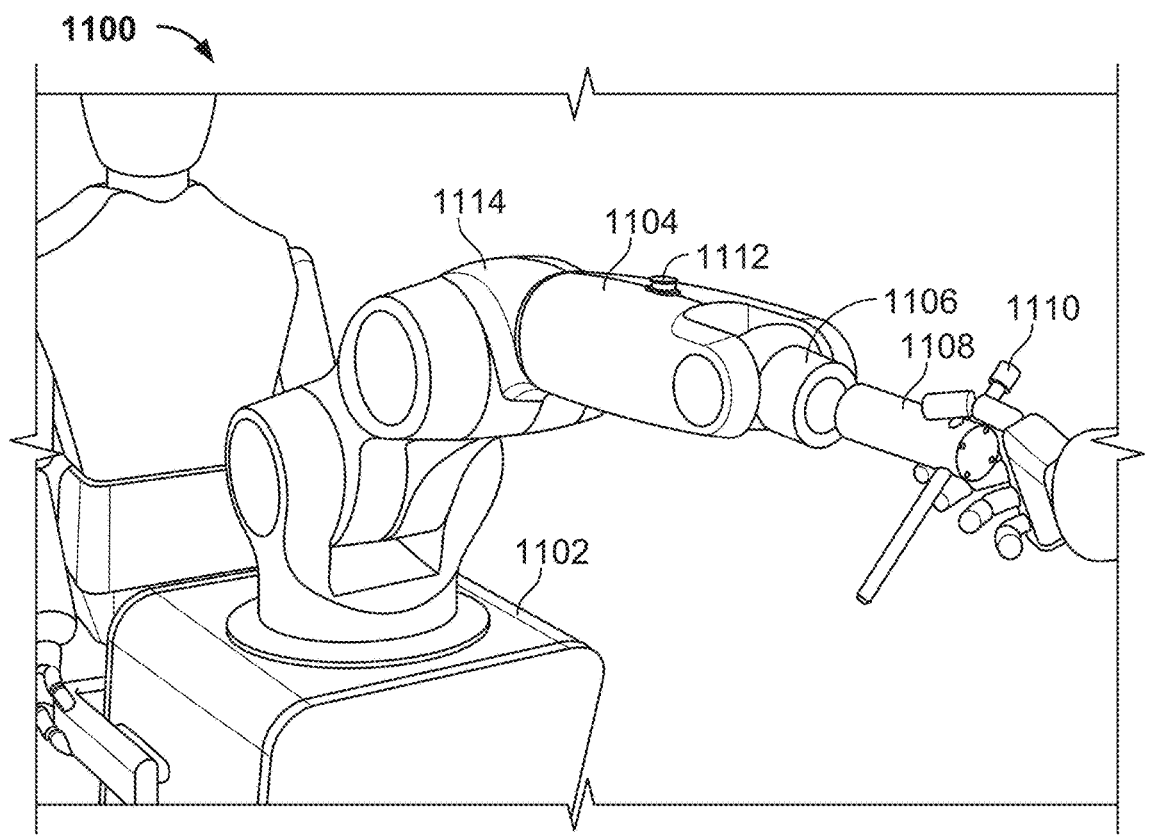
FIG. 11 is a diagram illustrating the attachment of a surgical end effector onto a robot in drape mode, in accordance with various embodiments of the disclosed technology.

FIG. 11 illustrates the attachment of a surgical end effector 1108 to the robot arm connector 1106 in drape mode. In drape mode, the robot arm 1114 is extended so that an end effector 1108 may be placed on the robot arm connector 1106. In some embodiments, the robot arm connector 1106 is located at the end of the robot manipulator 1104. Although not shown in FIG. 11, the surgical drape will typically be in place over the robot arm 1114 and cart 1102 when the end effector 1108 is inserted into, or otherwise attached to, the connector 1106. The connector 1106 may be configured to at least partially protrude from the surgical drape, such that a sterile cap, collar, or other covering of the connector may be installed prior to attachment of the end effector 1108 into the connector 1106 to maintain sterile seal.

The robot arm connector 1106 is configured to pass electrical signals from the rest of robot arm 1114 to end effector 1108. The electrical signals may be passed by a separate cable that passes through the sterile drape. The cable may be integrated with the sterile drape to simplify handling for the user. An operator attaches the end effector 1108 to the robot arm connector 1106. Once attached to the surgical end effector 1108, the robot arm connector 1106 secures lock of the end effector 1108. In the embodiment shown in FIG. 11, the robot end effector 1108 is a surgical tool connector that is attached to a surgical tool guide 1110. Surgical tool guide 1110 can contain different surgical tools and/or allow insertion of one or more surgical tools/implements therethrough. Surgical tool guide 1110 provides an accurate tool guide for surgical bone drilling, e.g., by providing a precisely aligned shaft through which a drill bit or drill may be inserted. Examples of different manners of guiding tools are shown in FIGS. 20A-20D. Surgical tool guide 1110 is used in spinal surgeries to allow for accurate surgical instrument placement. The surgical tool may be, for example, a tap such as the StealthStation® CR Horizon Legacy Taps from Medtronic, Inc. of Minneapolis, Minn. Other surgical instruments may be used by the system such as a drill bit, pedicle finder, screw-based implant, awl, surface-pointing device, screw based implant, screw driver, tap, implants, implants with extenders, or other similar instruments. For example, the surgical instrument guide may be configured to be used to guide a screw implant and a tissue protector. For example, once properly positioned near the target patient surgical site (i.e., vertebrae in spinal fusion surgery), in accordance with a trajectory, the surgical tool guide 1110 provides an accurate tool in which to insert a surgical drill bit for bone drilling. In some implementations, the surgeon defines the trajectory intra-operatively with little or no pre-operative planning. The surgeon may define the trajectory by positioning the end-effector in a desired position. As the surgeon moves the end effector, a projected trajectory may be displayed based on the position of the end-effector. The surgeon may view this display to adjust the position of the end-effector until he/she positions the end-effector such that a desired trajectory is obtained. Thus, the surgeon may define the trajectory in the operating room with little or no pre-operative planning. In some implementations, the surgeon may utilize images (e.g., CT scans) taken during a pre-operative planning session to assist with defining the trajectory. In some implementations, the trajectory is computed via initial 3D measurement of the patient. In some implementations, the desired trajectory is updated in real-time via real-time scanning In some embodiments, the robot arm manipulator 1104 includes an emergency stop switch 1112. The emergency stop switch may be placed on the robot arm, robot cart, or on the operator's panel.

Figure 12:
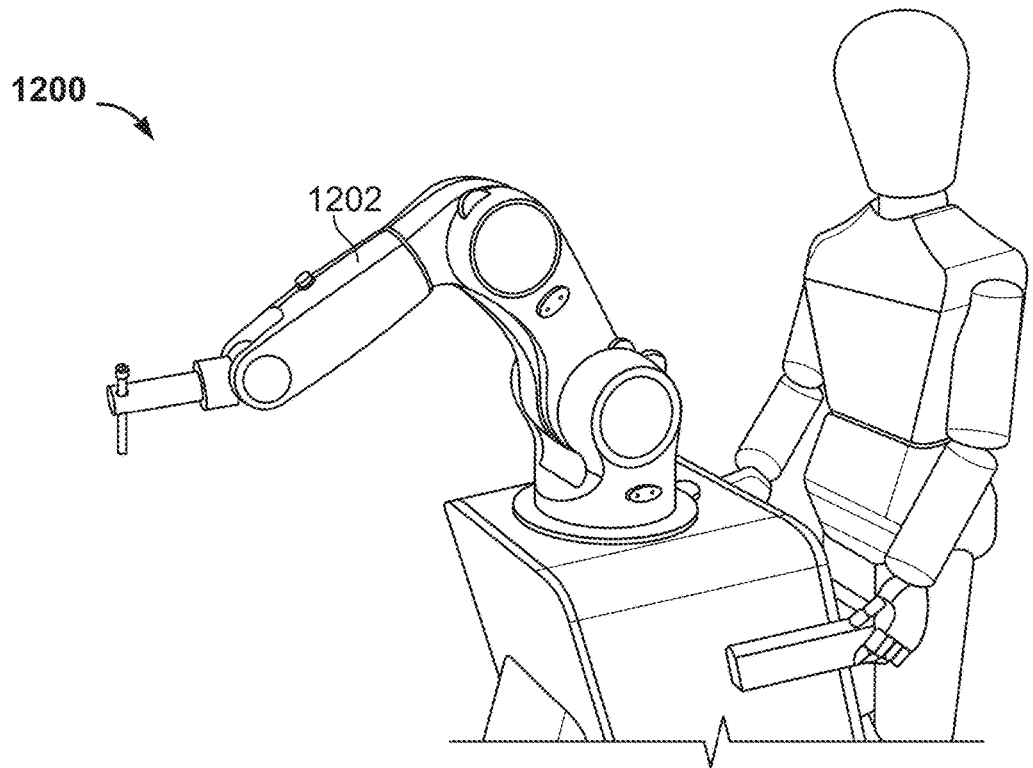
FIG. 12 is a diagram illustrating an exemplary configuration of a robotic system in a surgical procedure preparation mode, in accordance with various embodiments of the disclosed technology.

FIG. 12 illustrates an exemplary configuration of surgical robot 1200 in a surgery preparation mode. Once the surgical end effector has been securely attached to robot arm connector, the operator changes the arm configuration of the surgical robot arm 1202 from a draping arm configuration of FIG. 11 to a surgical preparation arm configuration depicted in FIG. 12 by pressing a surgical preparation mode switch on the surgical robot control panel. In an embodiment, the surgical arm 1202 is slightly lowered in surgical preparation mode from that of drape mode to be placed at the same elevation as the patient lying on an operation table.

Figure 13:
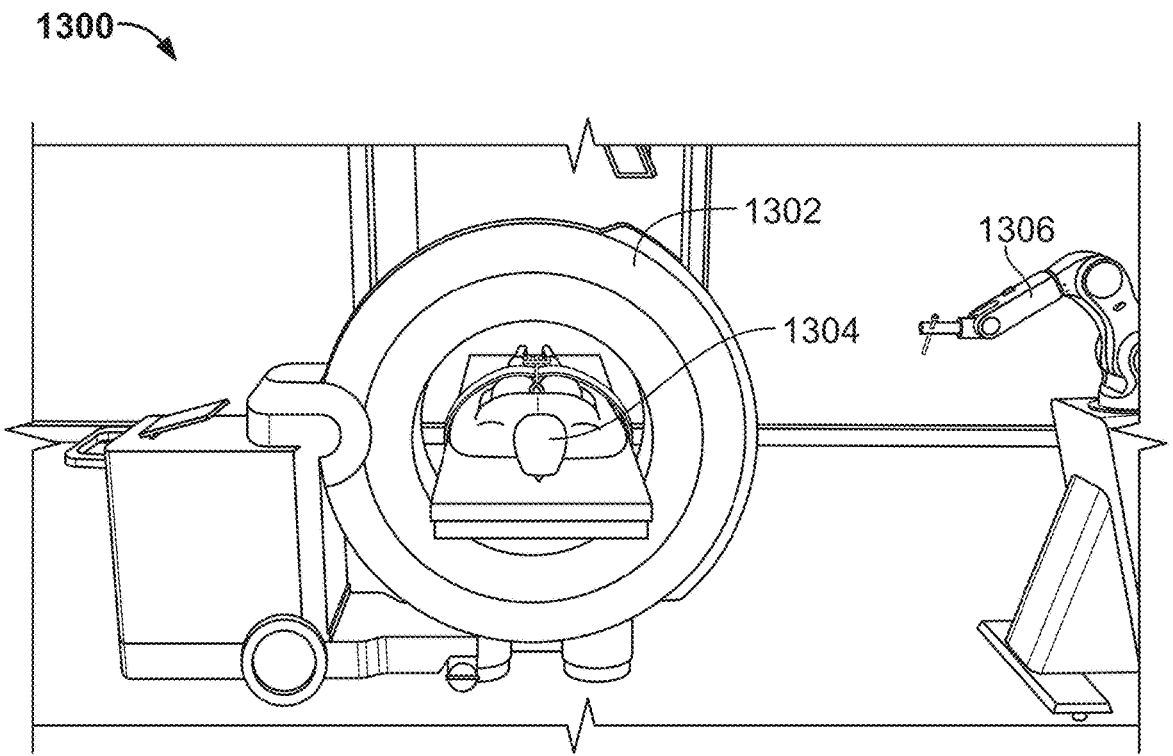
FIG. 13 is a diagram illustrating an example system for capturing 3D patient images to be used by a robotic surgical system, in accordance with various embodiments of the disclosed technology.

FIG. 13 illustrates an example system 1300 for capturing patient images prior to a surgical procedure, which may be used by a robotic surgical system 1306 during a surgical procedure in determining a desired trajectory for the end effector. A digital three dimensional scanner 1302 records images of patient 1304 to create a virtual patient representation. In the embodiment pictured in FIG. 13, the digital three dimension scanner is a 3D fluoroscopy. For example, the scanner may be the O-Arm® Surgical Imaging System for Medtronic, Inc. of Minneapolis, Minn. In other embodiments, digital three dimension scanner 1302 may be another medical imaging device such as a magnetic resonance image scanner, a nuclear magnetic resonance image scanner, an ultrasound machine, a photoacoustic imager, cardiac sonographer, a thermographic camera, a tactile imager, computed tomography scanner, fluoroscopy, 3D fluoroscopy, etc. Digital three dimension scanner 1302 generates a three dimension virtual image of the patient and transmits such a virtual image wirelessly to the processor of surgical system 1300. The processor may display such a two or three dimensional virtual patient representation on a display screen during the surgical procedure in conjunction with the calculated trajectories of the robotic end effector and surgical tool.

In some embodiments, the patient 1304 is scanned using the digital three dimension scanner 1302 before the surgical robot 1306 is positioned near the operating table on which patient 1304 lies.

Figure 14:
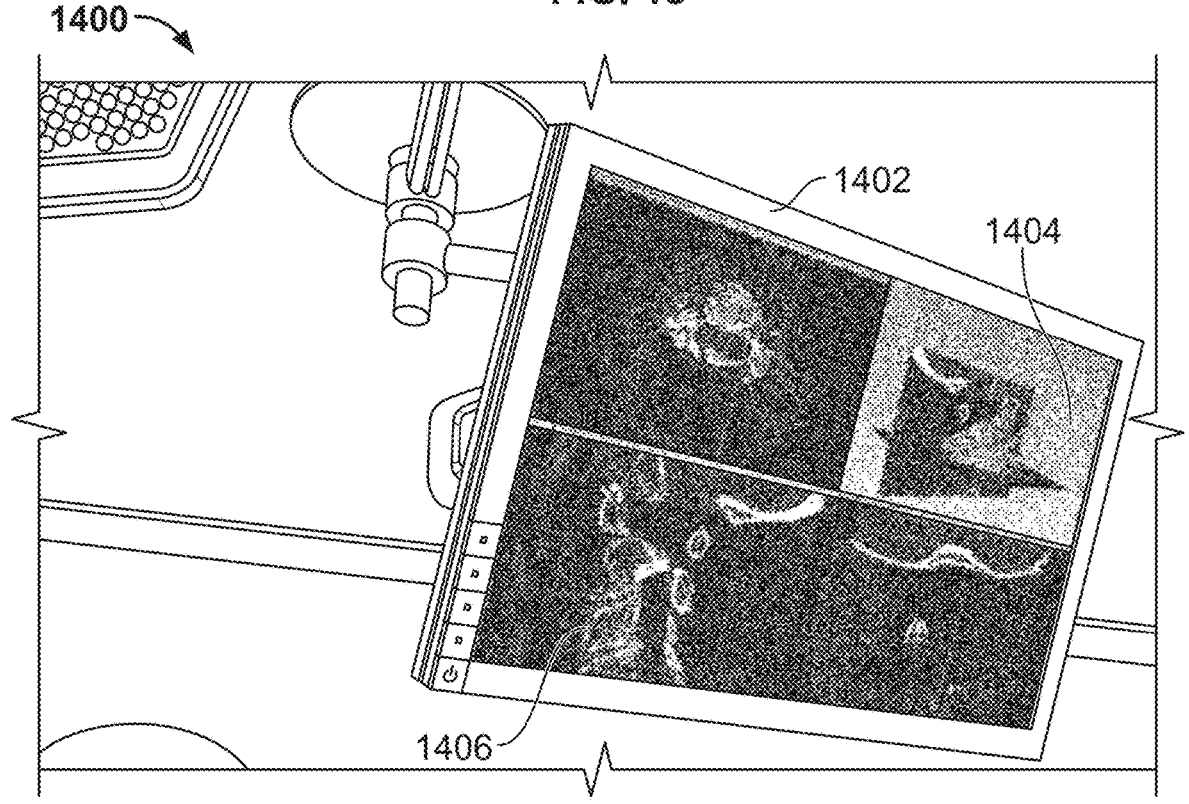
FIG. 14 is a diagram illustrating an example display screen displaying images of the patient and a surgical trajectory, in accordance with various embodiments of the disclosed technology.

FIG. 14 illustrates an example display screen 1402 displaying virtual model images 1404 and 1406 of the patient and a surgical trajectory. Here, the computed trajectory is the path of the surgical tool (e.g., drill) through the tissue (e.g., vertebrae, bone), which is defined by the angle and position of the end effector/tool holder and the patient situation. Such a display screen 1402 may be positioned in the operating room above or near the operating table. The display screen 1402 may display virtual models of the patient's organs, bones, and other surgical targets that are generated by the processor of surgical system 1400 after the patient has been scanned using a three dimensional scanner shown in FIG. 13. In some embodiments, the processor of surgical system 1400 superimposes a computed surgical tool trajectory and/or actual tool trajectory on an image of 1404 of the patient virtual model displayed on display screen 1402. The computed trajectory may be approved and/or modified by the surgeon. In some embodiments, the surgeon may sketch or select a planned trajectory on the patient virtual model image 1404 or 1406 displayed on display screen 1402. In some embodiments, a computed trajectory may be superimposed on the display screen 1402. In some embodiments, the system disallows selection of any trajectory determined to pose danger to the spinal cord or arteries and/or disallows movement of the tool into predefined no-go zones. In some implementations, images are used to give feedback to the surgeon allowing him to determine the trajectory and/or make changes to a trajectory.

In some embodiments, the processor of the surgical system 1400 is configured to calculate a path by which the robotic end effector is to move from its current location in 3D space to the location at which the end effector is positioned in proper alignment with respect to the computed trajectory for drilling. The surgical system processor may calculate such a path based on the determined patient position and surgical tool/end effector position, and may be guided by markers placed in select locations on the patient and/or robot. The path, itself, may be indicated on the display to help guide a surgeon who is maneuvering the end effector in force control mode. A signal (e.g., visual, audible, or combination) may be provided when the desired position of the end effector is achieved, in accordance with the desired, computed trajectory, to indicate to the surgeon or other operator that the end effector is properly aligned for the procedure, and the system can be switched from force control mode to active holding position, where the end effector may be held in place by the robot without any movement, or with small movements in accordance with real time compensation for vertebrae and/or other patient movement during the surgical procedure.

In some embodiments, during positioning of the end effector by the surgeon or other operator in advance of the surgical procedure, the surgical system 1400 continuously monitors surgical tool position and updates the path displayed on the display screen 1402 for moving the tool to the desired position. For example, the tracking detector continuously monitors the position of the robot arm, end effector, surgical tool guide and patient position.

Figure 15:
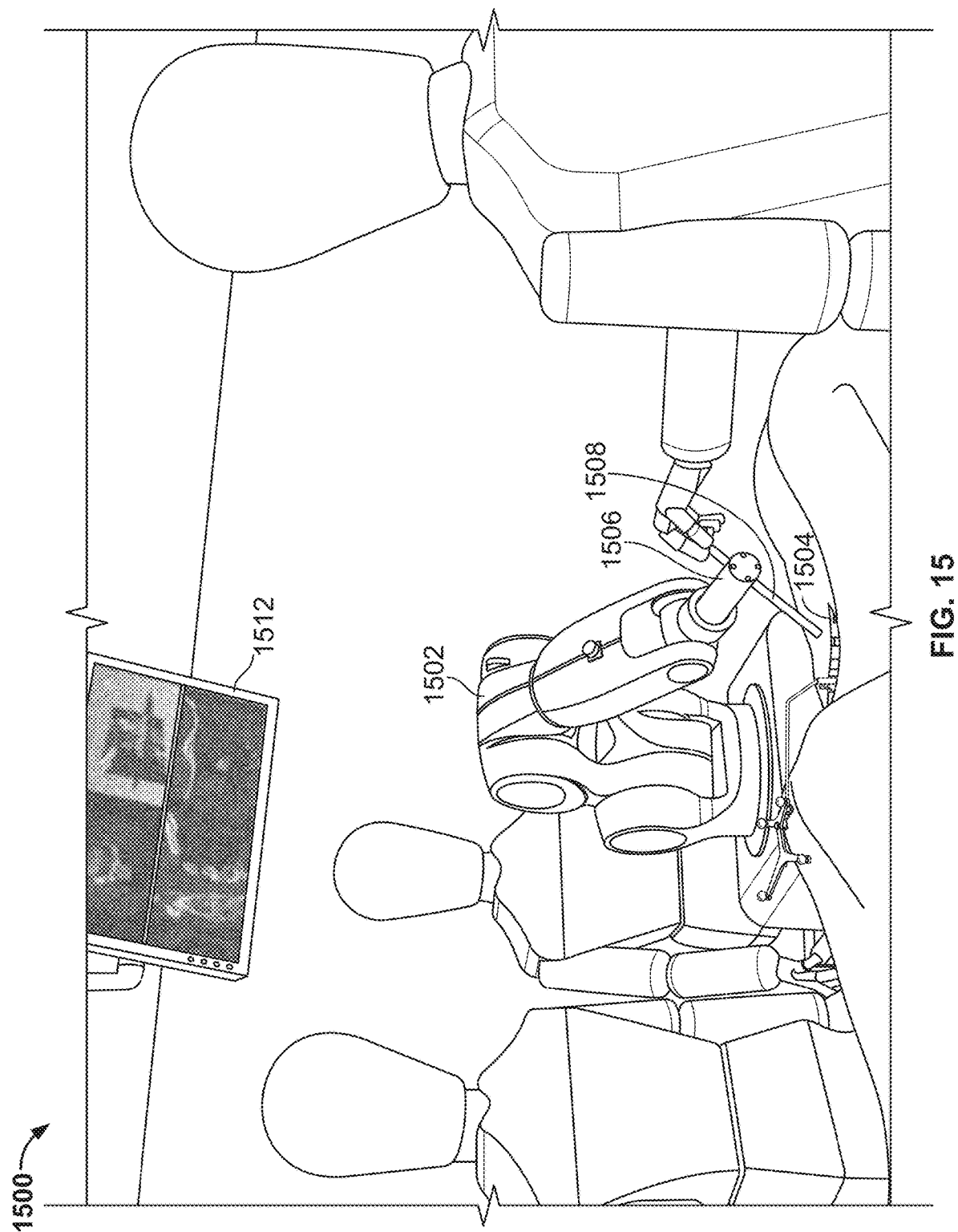
FIG. 15 is a diagram illustrating a surgeon positioning a robotic arm in preparation of a surgical procedure, in accordance with various embodiments of the disclosed technology.

FIG. 15 illustrates positioning by a surgeon of the end effector of the robotic arm in preparation for a surgical procedure. Once the patient has been scanned with the three dimensional image scanner, the surgical robot 1502 is placed into surgery mode as described in relation to FIG. 9.

Once the robot is placed into surgery mode by the operator, the processor of the surgical system 1500 allows the mobile cart to be moved from a position away from the operating table, to a position at or close to the operation table, such that the robot arm is within reach of the region of the patient's body to be operated on. An operator/surgeon can place the robot into force control mode as described in relation to FIG. 3. Upon entering force control, surgical robot 1502 allows its actuator to move the end effector 1506 at a controlled pace in the direction of the force applied by the operator/surgeon on the manipulator or the end effector 1506. In some implementations, the tracking detector of surgical system 1500 continually monitors the position of the surgical tool guide 1508, end effector 1506 and patient 1504, and displays updates on display screen 1512, thereby guiding the surgeon to position the end effector in accordance with the desired trajectory (e.g., a computed trajectory or a trajectory identified by a surgeon).

Figure 16:
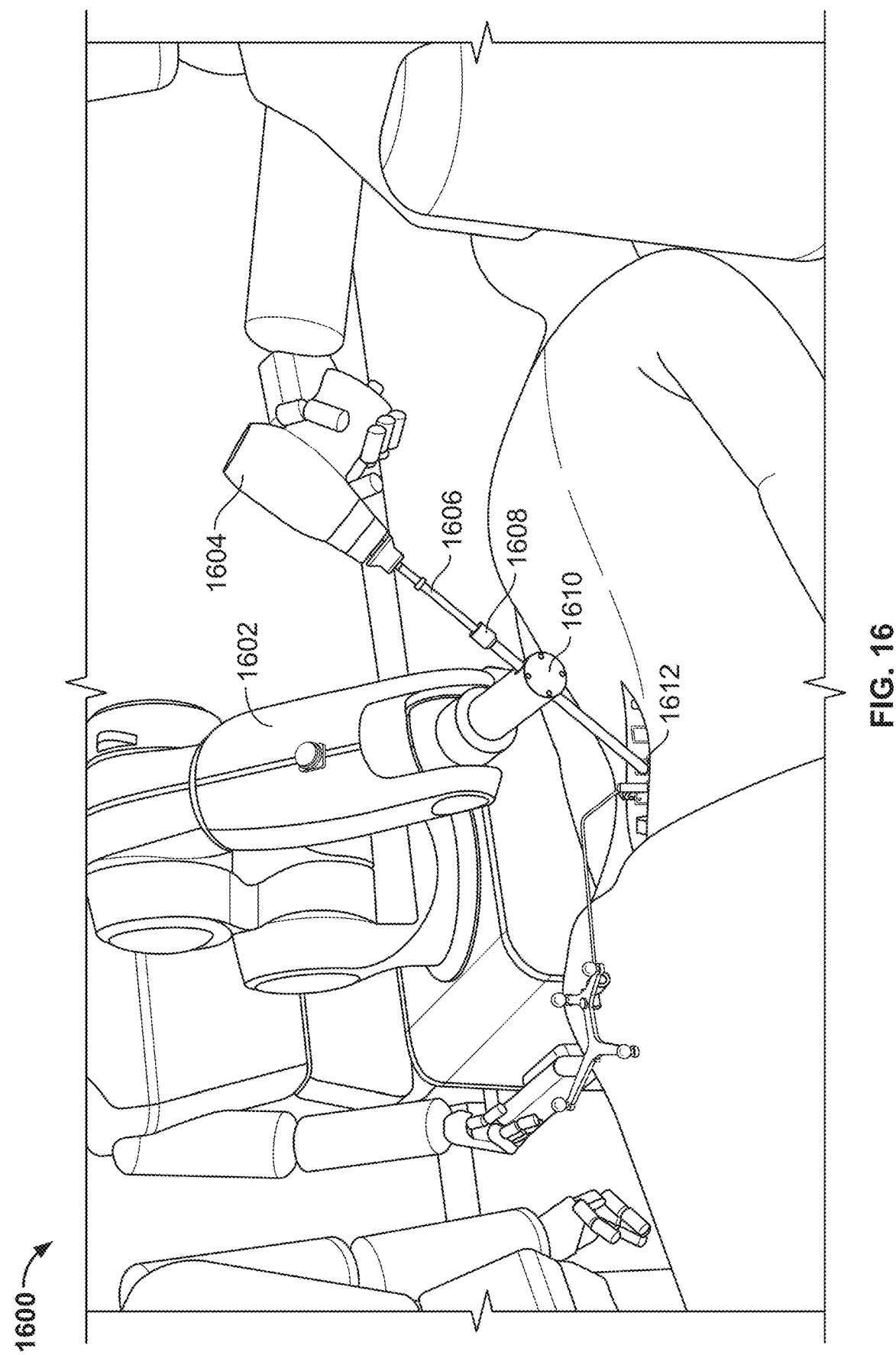
FIG. 16 is a diagram illustrating a surgeon performing a surgical procedure assisted by a surgical robotic system, in accordance with various embodiments of the disclosed technology.

FIG. 16 illustrates a surgeon performing a surgical procedure assisted by a surgical robotic system. Once the surgical tool guide 1608 has been positioned close to the target site 1612, the surgical robot is placed into an active holding position by the processor of the surgical system 1600. In some embodiments, the processor instructs the actuator to not allow the end effector to be moved regardless of the amount of force applied to manipulator 1602, end effector 1610, or tool guide 1608 as described in relation to FIG. 3. In some embodiments, movement of the end effector due to force and/or torque applied by the surgeon is compensated for in real time such that the end effector remains in the same, stable position.

In some embodiments, the surgical robot is placed into an active holding position by the processor of surgical system 1600 upon determining that the tool guide 1608 has been positioned within sufficient alignment with the target trajectory such that a tool positioned in the tool holder (end effector) makes contact with the patient at a target contact point 1612 in alignment with the target trajectory. This determination may be made in real time using images received from tracking detectors in real time. In some embodiments, the processor may determine that the tool guide 1608 has been positioned adequately close to the target site 1612 of the surgery by receiving an input signal, from force sensors located at the tip of tool guide 1608, indicating that the tip of the tool guide has touched the target site 1612.

Once the surgical system 1600 is placed in an active holding position, an operator/surgeon can insert a surgical tool 1606 into the tool guide 1608 (and/or maneuver a surgical tool that has already been placed in a 'resting' position within the tool guide, e.g., the surgeon can extend a drill bit deeper through the end effector tool guide such that contact with the vertebra is made). In some embodiments, insertion of the tool into the tool guide and/or maneuvering of a tool through the tool guide is disallowed unless the active holding position is in effect.

In the embodiment shown in FIG. 16, the robotic surgical system is being used for spinal fusion surgery. The surgical tool that is first inserted into tool guide 1608 is a surgical drill bit 1606. The surgical drill bit is used to prepare the hole in a vertebra for a screw to be placed fusing two vertebrae together using a surgical drill 1604. In some embodiments, the drill bit is electrically coupled to the surgical system 1600 such that force sensors at the tip of the drill bit 1606 provide haptic feedback, through the tool guide, to the user. The surgical system processor determines the magnitude of haptic feedback to be returned to the operator/surgeon upon determining how far the operator/surgeon has drilled into a no-go zone using drill bit 1606. The surgical system processor can determine how far the operator/surgeon has drilled into a no-go zone using drill bit 1606 using pressure sensors and position sensors (i.e., piezoelectric transducers). Such sensors located at the tip of the surgical tool (i.e., drill bit 1606) allow the surgeon also assist the surgeon/operator to properly align the drill bit with respect to the target site 1612. For example, the force sensors return electrical signals to the processor of the surgical system through the tool guide 1608, which is coupled to the end effector 1610. These sensor signals from the tip of the drill bit allow the processor to calculate a haptic feedback magnitude based on how well aligned the drill bit is with respect to the target surgical site 1612. A higher magnitude haptic feedback force is returned to the operator/surgeon, through the tool guide based on the degree of misalignment of the drill bit tip with respect to the surgical site 1612. In some embodiments, the surgical system processor may also display a measure of how well the drill bit is aligned on the display screen. In some implementations, the surgeon has direct control of the tool that is being inserted. For example, the surgeon may insert the tool into the guide and prepare the hole while being provided with direct force feedback in the axis of insertion.

Once the surgical hole is prepared, the user turns off the surgical drill 1604 and removes the drill bit 1606. The surgical robotic arm is removed from active holding mode and the operator/surgeon is allowed to withdraw the tool guide away from the target surgical site.

Figure 17:
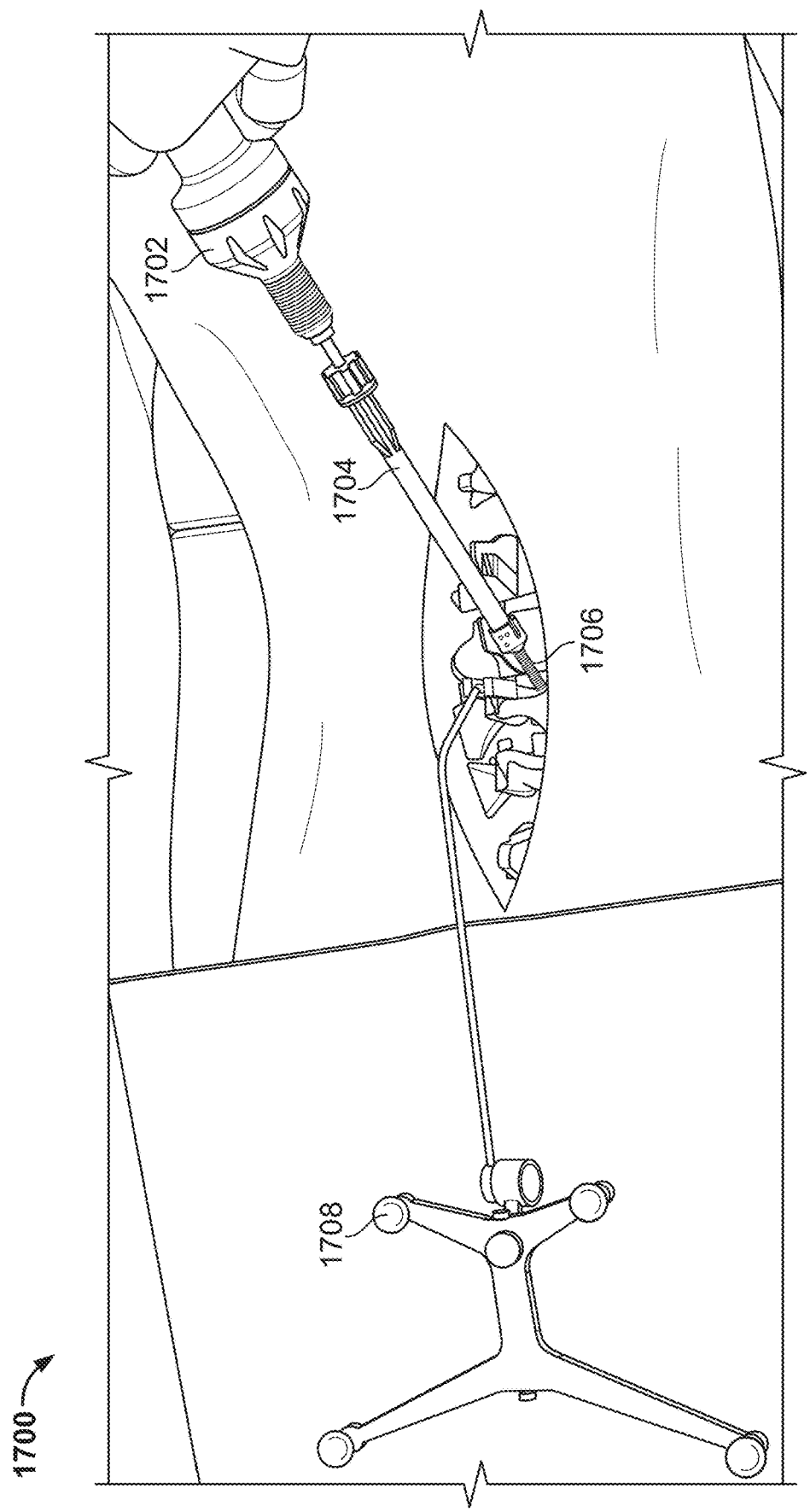
FIG. 17 is a diagram illustrating a surgeon performing a surgical procedure assisted by a surgical robotic system, in accordance with various embodiments of the disclosed technology.

FIG. 17 illustrates a surgeon performing another surgical procedure assisted by a surgical robotic system. Once the surgeon retracts the drill bit and end effector away from the surgical target site, the surgeon places a screw 1706 (e.g., pedicle screw) and screws it using a power screwdriver 1702. The screw may also be placed through the tool guide. In some embodiments, screw 1706 is attached to the power screwdriver 1702 through a tool guide 1704. In some embodiments, the tool guide 1704 moderates the screwing motion at a predetermined pace.

In some embodiments, the position of the surgical screw 1706 is monitored using the tracking detector. The tracking detector 1708 monitors the position of screw 1706 with respect to the vertebra. The surgical system processor calculates and displays a screw trajectory on the display screen using the position of the vertebra and the screw position. The process described above for drilling a hole and placing a screw in each vertebra is repeated using the surgical system until all the screws required for the spinal fusion surgery are screwed in.

Figure 18:
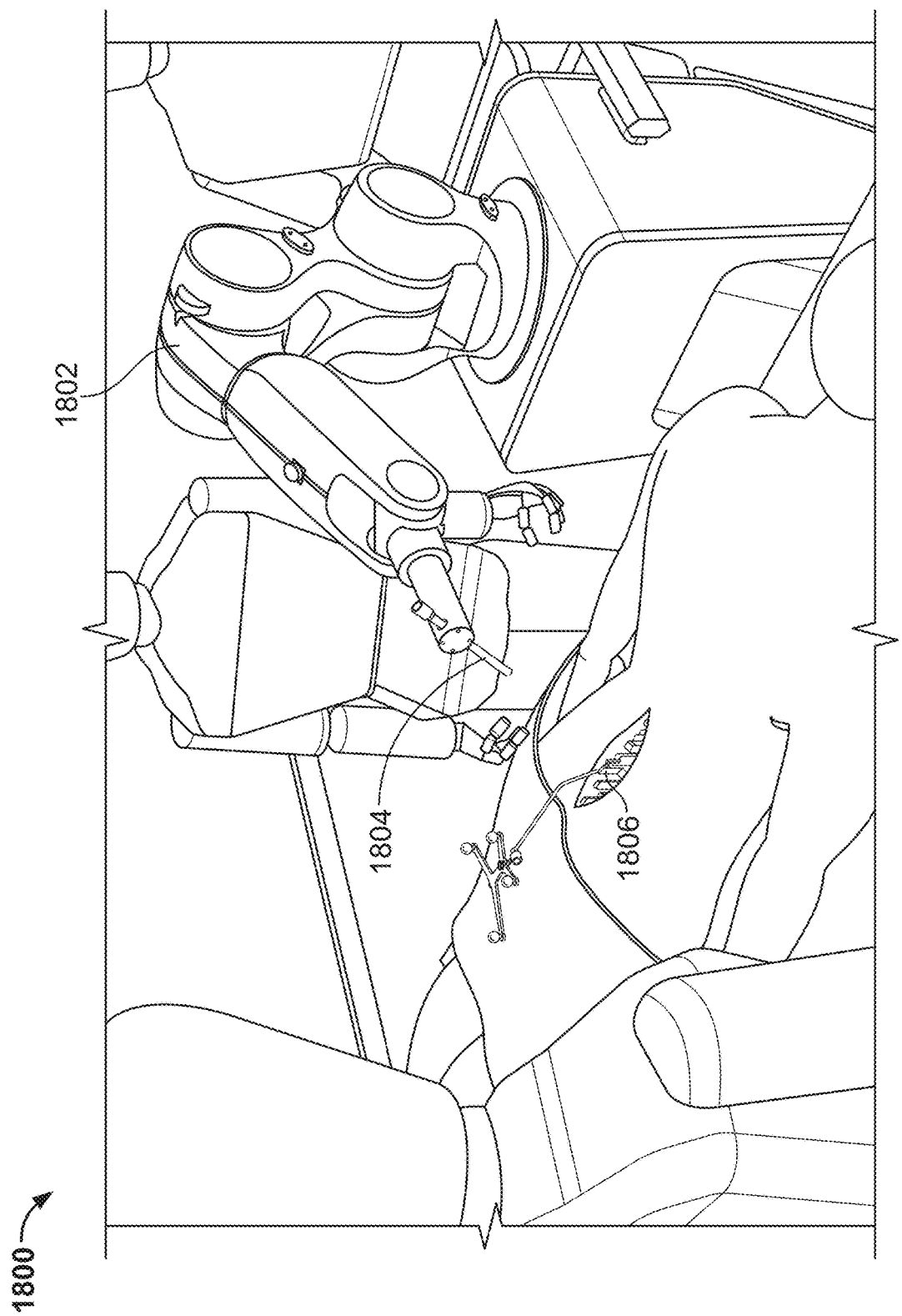
FIG. 18 is a diagram illustrating an example robotic surgical system withdrawing from an operating table upon completion of a surgical procedure, in accordance with various embodiments of the disclosed technology.

FIG. 18 illustrates an example robotic surgical system withdrawing from an operating table upon completion of a surgical procedure. Once all the screws have been placed in all the required vertebrae at the surgical site 1806 for the spinal surgery, the surgical process concludes. Upon conclusion of the surgical process, in some implementations, the operator of surgical system 1800 deactivates surgery mode of the surgical system 1800 by pressing the Off switch twice on the surgery mode subpanel of the surgical robot control panel. In some implementations, the operator may exit the operating mode by selecting an Off button and subsequently selecting the confirmation button within a predefined time window (e.g., 10 seconds). In some implementations, the user may move the end effector on the surgical robot arm 1802 to withdraw the tool guide 1804 along with the rest of the robot arm 1802 away from the surgical site 1804.

Figure 19:
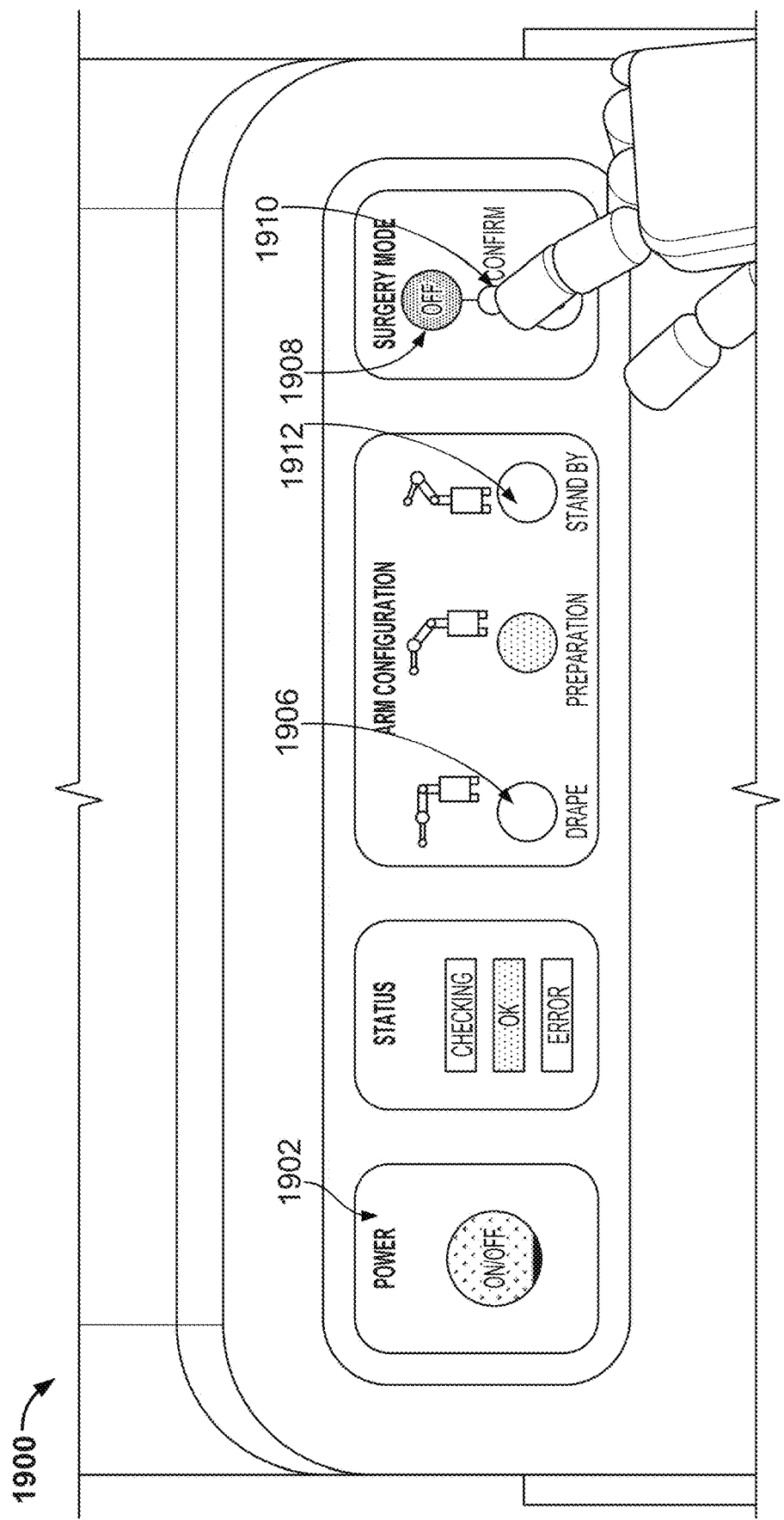
FIG. 19 is a diagram illustrating a nurse/member or medical personnel changing a robotic configuration using an example control panel of a robotic surgical system upon completion of a surgical procedure, in accordance with various embodiments of the disclosed technology.

FIG. 19 illustrates a surgeon or operator/assistant changing the robotic configuration using an example control panel 1900 of a robotic surgical system upon completion of a surgical procedure. In some implementations, upon conclusion of the surgical process, the operator of surgical system deactivates surgery mode by pressing the Off switch 1908 twice on the surgery mode subpanel of the surgical robot control panel. A confirmation light 1910 on the surgery mode subpanel may light up once the Off button 1908 is pressed once and is turned off when the Off button 1908 is pressed yet again. Requiring the operator to press the off button 1908 twice reduces the risk of the robot being accidentally being placed out of surgery mode as a result of an accidental button push.

Once the operator deactivates surgery mode, the surgical system processor instructs the mobile cart to release the stabilizing lock on the mobile cart of the surgical robot. The operator then moves the surgical robot away from the operating table to a cleaning area.

In some embodiments, once the surgical robot mobile cart is placed in the cleaning area, the operator places the surgical robot into drape configuration by activating the Drape switch 1906. The surgical robot arm changes its arm configuration to a draping configuration. The operator removes the sterile drape form the surgical robot and places the robot arm into a standby configuration by activating Standby switch 1912. Once the robot arm changes its arm configuration from a draping configuration to a standby configuration, the operator powers off the surgical robot by pressing the ON/OFF button 1902 and removes the power plug from the wall power socket. The operator then places the powered off surgical robot in storage.

In some embodiments, the surgical robot stores system logs for each surgical procedure in a memory unit such as memory 242 of FIG. 3. A maintenance worker may examine such logs while performing periodic maintenance and repair of the surgical robot.

FIGS. 20A through 20D illustrate example configurations of a surgical tool and surgical end effectors attached to a robotic arm of a robotic surgical system.

FIG. 20A illustrates a configuration of robotic arm 2000. The robot arm end effector 2004 is connected to a navigation lock 2006 through a tool connector 2010. The navigation lock 2006 is attached to a manipulator 2002 on one end and attached to the surgical tool (i.e., drill bit) on the other end. The robot arm controls the navigation lock 2006 and in result can control the displacement of the surgical tool 2008 in a controlled pace in response to a force applied by a user on the manipulator 2002. Such control is achieved as result of the optional communication between the navigation lock 2006 and the surgical system processor through connector 2010.

FIG. 20B illustrates a configuration of robotic arm 2020. In configuration 2020, the navigation lock 2026 connecting the manipulator, surgical tool, and robot end effector 2024, is connected to a linear guiding system 2022, through a connector 2030. The linear guiding system 2022, which is connected to the end effector 2024, is a movement rail that can displace the surgical tool, via the navigation lock 2026, in two to three dimensions. In some implementations, this provides the surgeon with direct force feedback along the insertion axis.

Figure 20D:
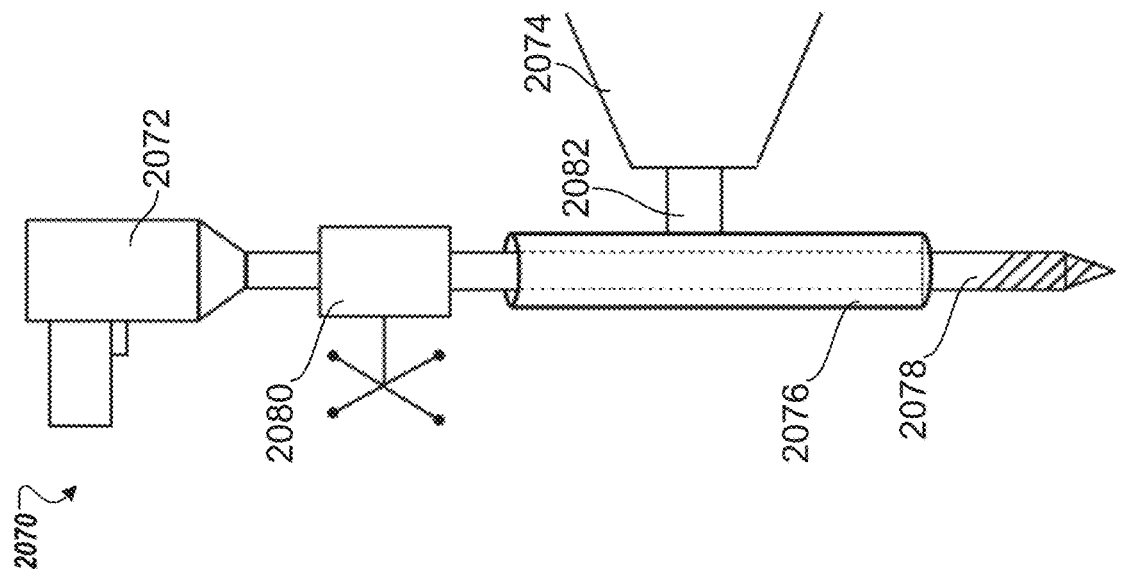
Figure 20C:
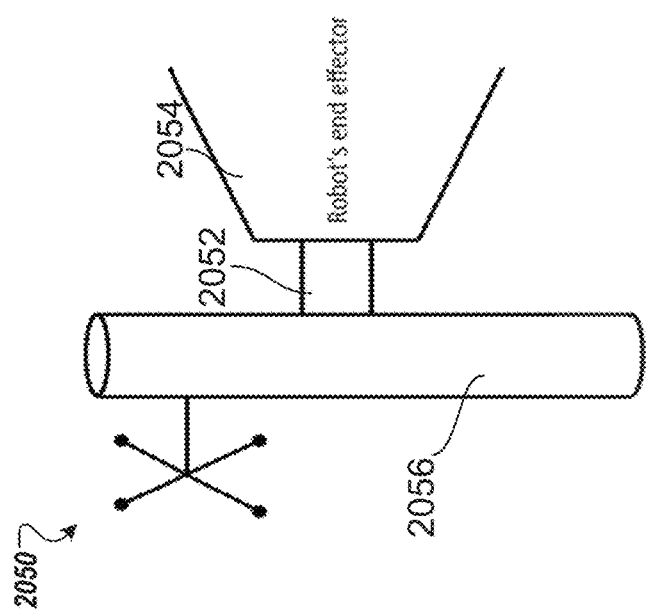

FIG. 20C illustrates a configuration of robotic arm 2050. In configuration 2050, a surgical tool guide 2056 is connected to the robot arm end effector through connector 2052. Connector 2052 provides optional communication between the surgical system processor and the surgical tool guide 2056.

FIG. 20D illustrates a configuration of robotic arm 2070. In configuration 2070, a surgical tool guide 2076 attached to a surgical tool 2078 is connected to a robot arm end effector 2074 through a connector 2082. The surgical tool is connected to a navigation lock 2080. The navigation lock is connected to a manipulator 2072 on the end that is not connected to the surgical tool. Such a configuration combines the features of configuration 2050, namely the surgical tool guide, with that of configuration 2000.

In some implementations, the navigation lock as shown in FIGS. 20A through 20D includes a navigation marker and a tool holder. The tool holder attaches to the robot arm and the navigation marker is used by a navigation system to monitor the position of the end effector and/or tool holder.

Figure 21:
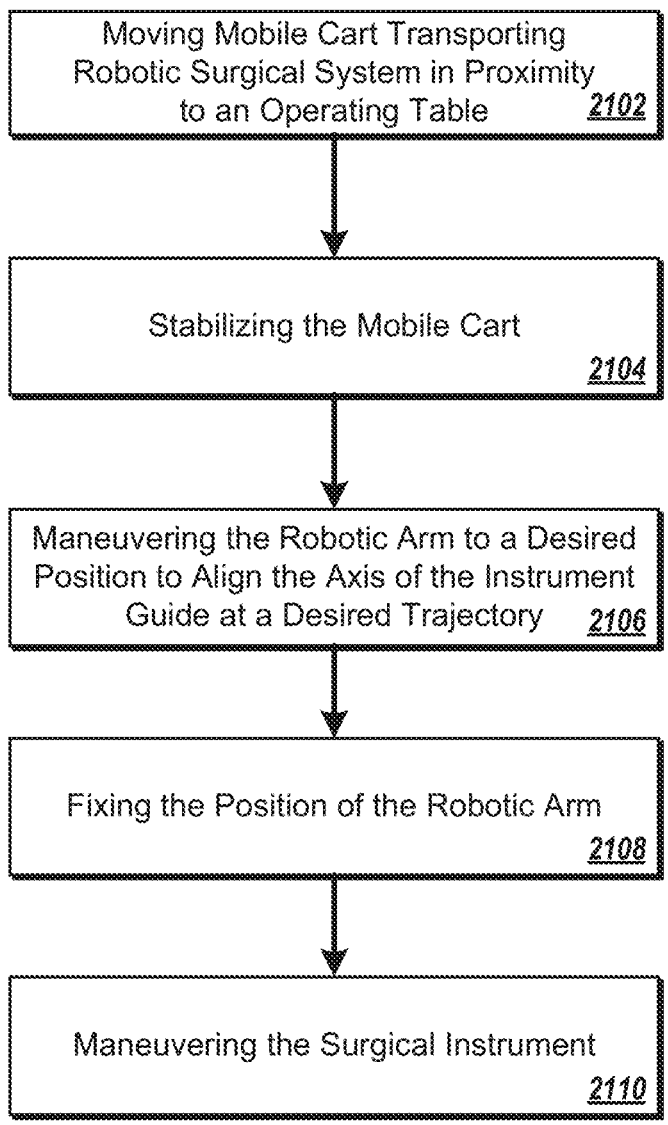
FIG. 21 is a flowchart of an example method of performing a surgery with a robotic surgical system.

FIG. 21 is a flowchart of an example method 2100 of performing a surgical procedure with a robotic surgical system, such as the robotic surgical system disclosed herein. In some implementations, the method 2100 includes moving a mobile cart transporting a robotic surgical system comprising a robotic arm in proximity to an operating table (2102). As described above, the robotic arm has an end effector comprising a surgical instrument guide attached thereto. The surgical instrument guide is, in some implementations, configured to hold and/or restrict movement of a surgical instrument therethrough.

The method 2100 may include stabilizing the mobile cart (2104). For safety reasons, the mobile cart is provided with a stabilization system that may be used during a surgical procedure performed with a surgical robot. The stabilization mechanism increases the global stiffness of the mobile cart relative to the floor in order to ensure the accuracy of the surgical procedure. Once stabilization is engaged, the mobile cart is secured in place on the operating room floor and cannot move.

After stabilizing the mobile cart, the robotic arm is maneuvered to a desired position to align an axis defined by the instrument guide at a desired trajectory in relation to a patient situation (2106). As described above, the surgical instrument guide may comprise a rigid hollow tubular structure having a first open end and a second open end. The structure may define the axis along which movement of a surgical instrument (fitted with a tool support) sliding through the structure is restricted.

The position of the robotic arm and, therefore, the position of the surgical instrument guide is fixed (2108) after the robotic arm is maneuvered to the desired position. After the position of the robotic arm is fixed, a surgical instrument is maneuvered in a manner that is constrained by the surgical instrument guide (2110). As described above, the surgical instrument may be fitted with a tool support shaped and sized to slide through the surgical instrument guide along the axis defined by the guide. The tubular structure of the surgical instrument guide may have an interior surface shaped and sized to accommodate the tool support sliding through the guide such that movement of the tool support is constrained in all directions except along the axis defined by the guide. The tubular structure may include a longitudinal notch along its length that is sized in relation to a peg to (i) permit a marker attached to the tool support via the peg to be viewable by a navigation camera along an entire range of movement of the tool support through the guide, (ii) constrain movement of the navigation marker in a fixed orientation along the axis defined by the guide, and (ii) permit the tool support to slide along the axis defined by the guide while the guide is held in a fixed position by the robotic surgical system. The marker (e.g., navigation marker) may be, for example, a navigation tracker such as the Dedicated NavLock™ tracker from Medtronic, Inc. of Minneapolis, Minn.

Figure 22:
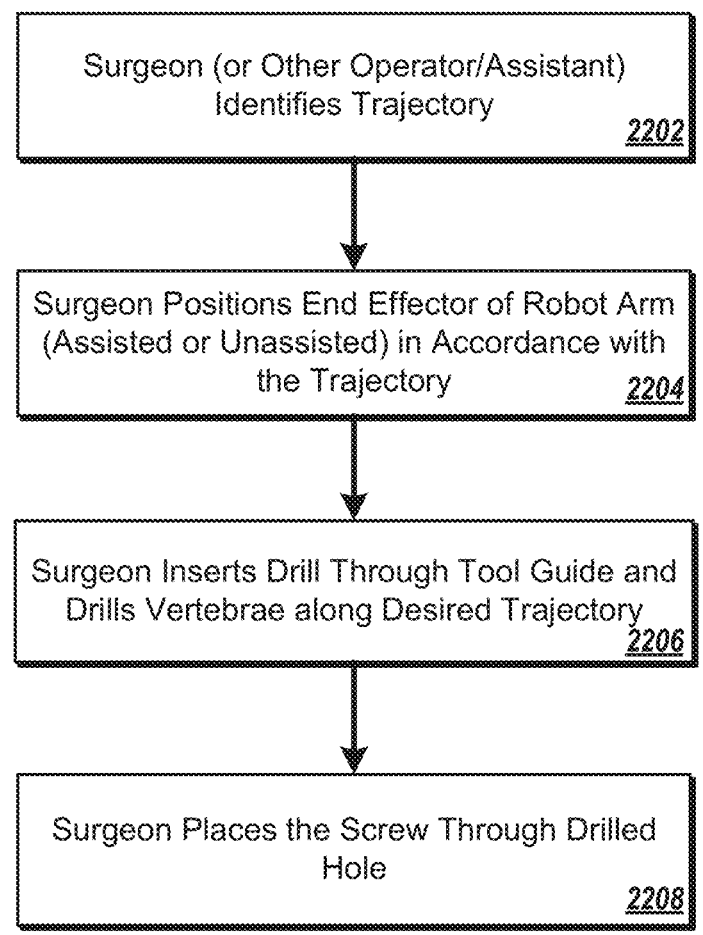
FIG. 22 is a flowchart of an example of a method for performing a minimally invasive surgery using a robotic surgical system as a drill guide.

FIG. 22 is an example of a method 2200 for performing a minimally invasive a surgical procedure using a robotic surgical system as a drill guide. The surgeon or other operator/assistant identifies a trajectory (2202). This includes complete identification of the trajectory done by the surgeon as well as computer assisted definition/identification of the trajectory (e.g., the computer of the robotic surgical system identifies/defines a trajectory which is presented to and/or approved by the surgeon). Next, the surgeon positions the end effector in accordance with the trajectory (2204). The positioning may be assisted or unassisted by the robotic surgical system. In some implementations, the surgeon may be assisted using various types of indications such as visual and/or sound indications. After the position of the robotic arm is fixed, a surgical instrument is maneuvered in a manner that is constrained by the surgical instrument guide. In this example, the surgeon drills through the tool guide (2206). In the case in which a drill guide is coupled to the end effector, an operator may insert a drill into the drill guide without moving the position of the end effector or drill guide. Thus, after carefully positioning the drill guide along a desired trajectory, an operator may accurately drill along the desired trajectory.

As described above, the surgical instrument (e.g., the drill) may be fitted with a tool support shaped and sized to slide through the surgical instrument guide along the axis defined by the guide. The tubular structure of the surgical instrument guide may have an interior surface shaped and sized to accommodate the tool support sliding through the guide such that movement of the tool support is constrained in all directions except along the axis defined by the guide. After drilling through the tool guide, the surgeon places the screw through the drilled hole (2208).

FIG. 23 describes an example method for performing a surgical procedure using a robotic surgical system. Prior to performing the surgical procedure, a virtual representation of a patient situation is generated (2302). The robot arm is placed into a surgical preparation configuration (2304). The robot mobile car is stabilized (2306) to ensure precise movements are performed by the robot. The robot arm is placed into a force control mode in which the surgeon positions the tool guide for alignment with a determined trajectory (2308). The tool may be manipulated according to the determined trajectory to perform the surgical operation (2310).

Figure 24A:
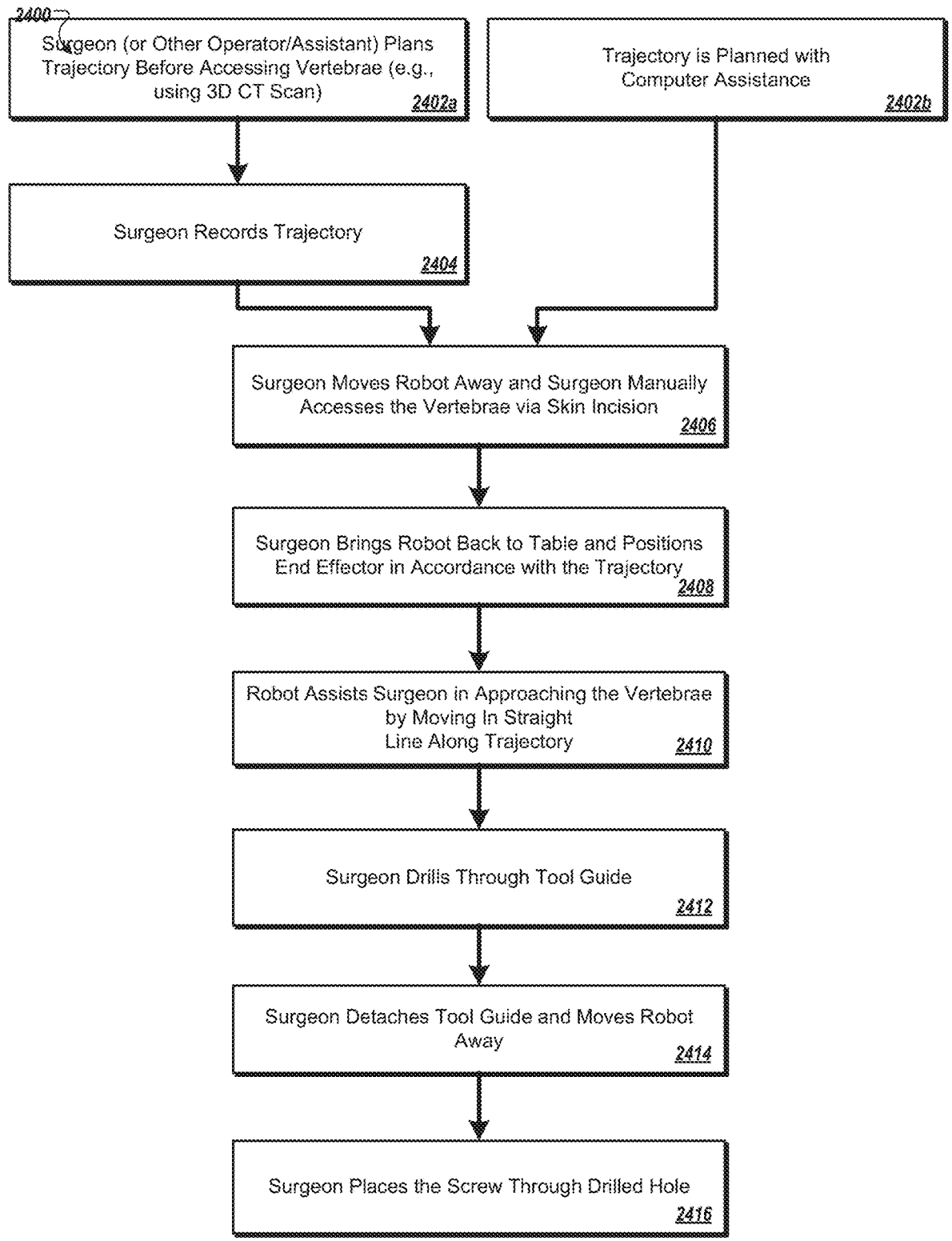
FIGS. 24A and 24B are flow charts describing example methods for performing minimally invasive surgery using a robotic surgical system, in accordance with various embodiments of the disclosed technology.

FIG. 24A describes another example method for performing a surgical procedure using a robotic surgical system. Specifically, FIG. 24A is an example of a method 2400 for performing a minimally invasive a surgical procedure using a robotic surgical system as a drill guide. The surgeon or other operator/assistant plans a trajectory before accessing vertebrae (2402*a*). The surgeon may plan the trajectory using a 3D CT scan and/or robot force control. After planning the trajectory, the surgeon records trajectory (2404) for later use.

Moreover, the system allows for a desired trajectory (e.g., for a drill guide during spinal surgery) to be set in a variety of manners based on the circumstances of the surgery. In some implementations, the surgical procedure is planned pre-operatively. In one example, the surgeon may define the desired trajectory (e.g., position of an implant) using imaging technology, such as CT images (e.g., 3D CT images). In the operating room the surgeon may be guided by the robotic system to accurately execute the planning. This may be achieved by robotic guidance of the surgical tools.

In another example, the computer of the robotic surgical system assists in defining/identifying the trajectory (2402*b*) (e.g., the computer of the robotic surgical system identifies/defines a trajectory which is presented to and/or approved by the surgeon or automatically approved). The computer of the robotic surgical system may analyze digital medical images to define the trajectory. The trajectory may be defined and/or displayed in relation to a marker, a vertebrae, or other physical landmark of the body, by additionally processing input received from a scanning system that identifies the location of such marker, vertebrae, or physical landmark during the surgical procedure, in real time. The trajectory may make use of scans conducted during the procedure, scans conducted prior to the procedure, or both. The scanning conducted prior to the surgical procedure may involve different equipment than scanning performed during the surgical procedure. The scanning may be conducted using a medical imaging device such as a computer tomography scanner, a magnetic resonance image scanner, a nuclear magnetic resonance image scanner, an ultrasound machine, a photoacoustic imager, cardiac sonographer, a thermographic camera, a tactile imager, a 3D fluoroscopy device, or the like.

The computer of the robotic surgical system may also use data regarding prior surgeries, data inputted by a surgeon (e.g., regarding areas to avoid), rankings or ratings for various trajectories that may be used, as well as other information to determine the trajectory. The determined trajectory may be stored by the robotic surgical system for later use during the surgery. For example, in the operating room the surgeon may be guided by the robotic system (e.g., robotic guidance of the surgical tools) to accurately execute at least a portion of the surgical procedure in accordance with the planned trajectory.

The surgeon moves the robot away and manually accesses the vertebrae via a skin incision (2406). Next, the surgeon brings the robot back to the table and positions the end effector in accordance with the recorded or planned trajectory (2408). As the surgeon positions the end effector, force feedback may be computed by processor and applied by actuator such that movement of the end effector is easier in direction of the recorded trajectory and a higher force is required to move the end effector away from the recorded trajectory. For example, the robot may guide the surgeon in the direction of the trajectory as the surgeon positions the end effector in accordance with the planned trajectory. In some implementations, the surgeon may be assisted using various types of indications such as visual and/or sound indications.

The robot assists the surgeon in approaching the vertebrae by moving in a straight line along the trajectory (2410). Next the surgeon drills through the tool guide (2412). After drilling through the tool guide, the surgeon detaches the tool guide and moves the robot away (2414). The surgeon then places the screw through the drilled hole (2416).

Figure 24B:
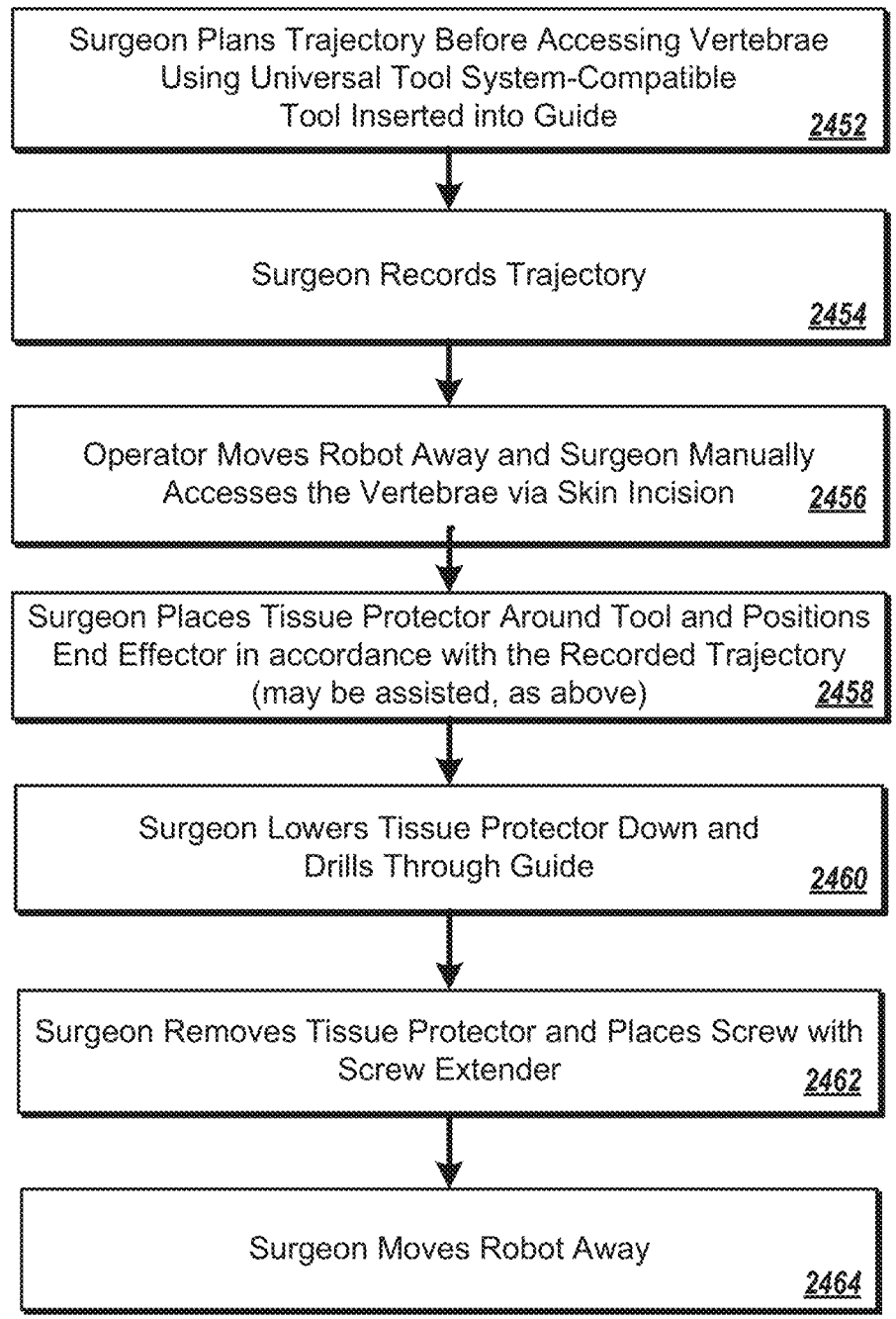

FIG. 24B is an example of a method 2450 of performing a minimally invasive a surgical procedure using a robotic surgical system as a drill guide and a universal surgical tools system (e.g., Medtronic's NavLock system). The surgeon plans a trajectory before accessing the vertebrae using a universal tool system-compatible tool inserted into the guide (2452). Next, the surgeon records the trajectory (2454). The operator moves the robot away and the surgeon manually accesses the vertebrae via a skin incision (2456). The surgeon places a tissue protector around the tool and positions the end effector in accordance with the recorded trajectory (may be assisted, as above) (2458). The surgeon lowers the tissue protector down and drills through the guide (2460). Next, the surgeon removes the tissue protector and places a screw with screw extender (2462). The surgeon then moves robot away (2464).

Figure 25:
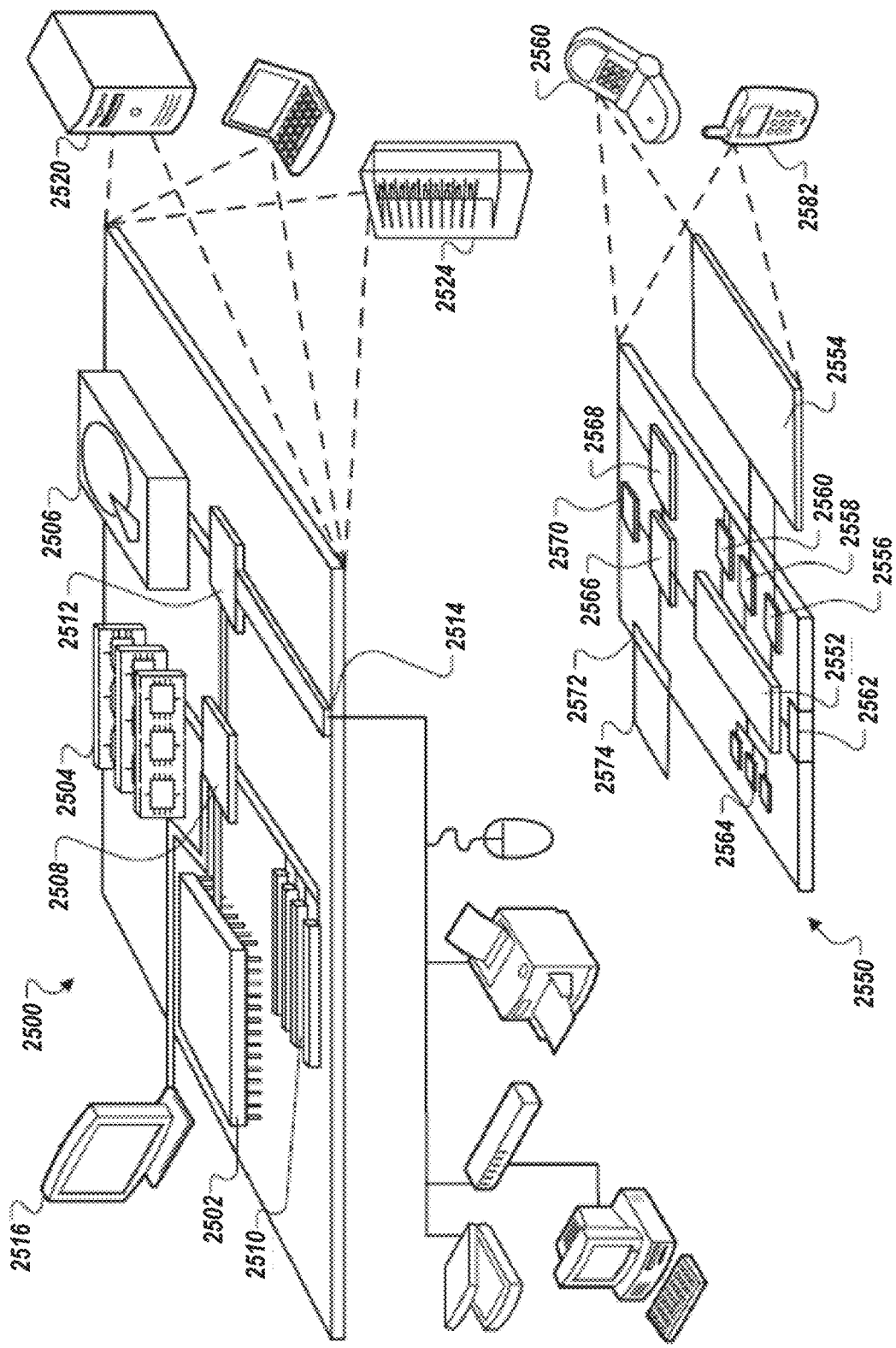
FIG. 25 is a block diagram of a computing device and a mobile computing device for use with a surgical robotic system, in accordance with various embodiments of the disclosed technology.

FIG. 25 shows an example of a computing device 2500 and a mobile computing device 2550 that can be used to implement the techniques performed by a processor of a surgical system such as computing system 302 and supervisory interlock system 356 of FIG. 3 and a memory unit such as memory unit 342 of FIG. 3 is described in this disclosure. The computing device 2500 is intended to represent various forms of digital computers, such as laptops, desktops, workstations, personal digital assistants, servers, blade servers, mainframes, and other appropriate computers. The mobile computing device 2550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 2500 includes a processor 2502, a memory 2504, a storage device 2506, a high-speed interface 2508 connecting to the memory 2504 and multiple high-speed expansion ports 2510, and a low-speed interface 2512 connecting to a low-speed expansion port 2514 and the storage device 2506. Each of the processor 2502, the memory 2504, the storage device 2506, the high-speed interface 2508, the high-speed expansion ports 2510, and the low-speed interface 2512, are interconnected using various busses, and may be mounted on a common motherboard or in other manners as appropriate. The processor 2502 can process instructions for execution within the computing device 2500, including instructions stored in the memory 2504 or on the storage device 2506 to display graphical information for a GUI on an external input/output device, such as a display 2516 coupled to the high-speed interface 2508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 2504 stores information within the computing device 2500. In some implementations, the memory 2504 is a volatile memory unit or units. In some implementations, the memory 2504 is a non-volatile memory unit or units. The memory 2504 may also be another form of computer-readable medium, such as a magnetic or optical disk.

The storage device 2506 is capable of providing mass storage for the computing device 2500. In some implementations, the storage device 2506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 2502), perform one or more methods, such as those described above. The instructions can also be stored by one or more storage devices such as computer- or machine-readable mediums (for example, the memory 2504, the storage device 2506, or memory on the processor 2502).

The high-speed interface 2508 manages bandwidth-intensive operations for the computing device 2500, while the low-speed interface 2512 manages lower bandwidth-intensive operations. Such allocation of functions is an example only. In some implementations, the high-speed interface 2508 is coupled to the memory 2504, the display 2516 (e.g., through a graphics processor or accelerator), and to the high-speed expansion ports 2510, which may accept various expansion cards (not shown). In the implementation, the low-speed interface 2512 is coupled to the storage device 2506 and the low-speed expansion port 2514. The low-speed expansion port 2514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 2500 may be implemented in a number of different forms, as shown in the figure. For example, it may be implemented as a standard server 2520, or multiple times in a group of such servers. In addition, it may be implemented in a personal computer such as a laptop computer 2522. It may also be implemented as part of a rack server system 2524. Alternatively, components from the computing device 2500 may be combined with other components in a mobile device (not shown), such as a mobile computing device 2550. Each of such devices may contain one or more of the computing device 2500 and the mobile computing device 2550, and an entire system may be made up of multiple computing devices communicating with each other.

The mobile computing device 2550 includes a processor 2552, a memory 2564, an input/output device such as a display 2554, a communication interface 2566, and a transceiver 2568, among other components. The mobile computing device 2550 may also be provided with a storage device, such as a micro-drive or other device, to provide additional storage. Each of the processor 2552, the memory 2564, the display 2554, the communication interface 2566, and the transceiver 2568, are interconnected using various buses, and several of the components may be mounted on a common motherboard or in other manners as appropriate.

The processor 2552 can execute instructions within the mobile computing device 2550, including instructions stored in the memory 2564. The processor 2552 may be implemented as a chipset of chips that include separate and multiple analog and digital processors. The processor 2552 may provide, for example, for coordination of the other components of the mobile computing device 2550, such as control of user interfaces, applications run by the mobile computing device 2550, and wireless communication by the mobile computing device 2550.

The processor 2552 may communicate with a user through a control interface 2558 and a display interface 2556 coupled to the display 2554. The display 2554 may be, for example, a TFT (Thin-Film-Transistor Liquid Crystal Display) display or an OLED (Organic Light Emitting Diode) display, or other appropriate display technology. The display interface 2556 may include appropriate circuitry for driving the display 2554 to present graphical and other information to a user. The control interface 2558 may receive commands from a user and convert them for submission to the processor 2552. In addition, an external interface 2562 may provide communication with the processor 2552, so as to enable near area communication of the mobile computing device 2550 with other devices. The external interface 2562 may provide, for example, for wired communication in some implementations, or for wireless communication in other implementations, and multiple interfaces may also be used.

The memory 2564 stores information within the mobile computing device 2550. The memory 2564 can be implemented as one or more of a computer-readable medium or media, a volatile memory unit or units, or a non-volatile memory unit or units. An expansion memory 2574 may also be provided and connected to the mobile computing device 2550 through an expansion interface 2572, which may include, for example, a SIMM (Single In Line Memory Module) card interface. The expansion memory 2574 may provide extra storage space for the mobile computing device 2550, or may also store applications or other information for the mobile computing device 2550. Specifically, the expansion memory 2574 may include instructions to carry out or supplement the processes described above, and may include secure information also. Thus, for example, the expansion memory 2574 may be provide as a security module for the mobile computing device 2550, and may be programmed with instructions that permit secure use of the mobile computing device 2550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 2552), perform one or more methods, such as those described above. The instructions can also be stored by one or more storage devices, such as one or more computer- or machine-readable mediums (for example, the memory 2564, the expansion memory 2574, or memory on the processor 2552). In some implementations, the instructions can be received in a propagated signal, for example, over the transceiver 2568 or the external interface 2562.

The mobile computing device 2550 may communicate wirelessly through the communication interface 2566, which may include digital signal processing circuitry where necessary. The communication interface 2566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 2568 using a radio-frequency. In addition, short-range communication may occur, such as using a Bluetooth®, Wi-Fi™, or other such transceiver (not shown). In addition, a GPS (Global Positioning System) receiver module 2570 may provide additional navigation- and location-related wireless data to the mobile computing device 2550, which may be used as appropriate by applications running on the mobile computing device 2550.

The mobile computing device 2550 may also communicate audibly using an audio codec 2560, which may receive spoken information from a user and convert it to usable digital information. The audio codec 2560 may likewise generate audible sound for a user, such as through a speaker, e.g., in a handset of the mobile computing device 2550. Such sound may include sound from voice telephone calls, may include recorded sound (e.g., voice messages, music files, etc.) and may also include sound generated by applications operating on the mobile computing device 2550.

The mobile computing device 2550 may be implemented in a number of different forms, as shown in the figure. For example, it may be implemented as a cellular telephone 2580. It may also be implemented as part of a smart-phone 2582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Figure 26:
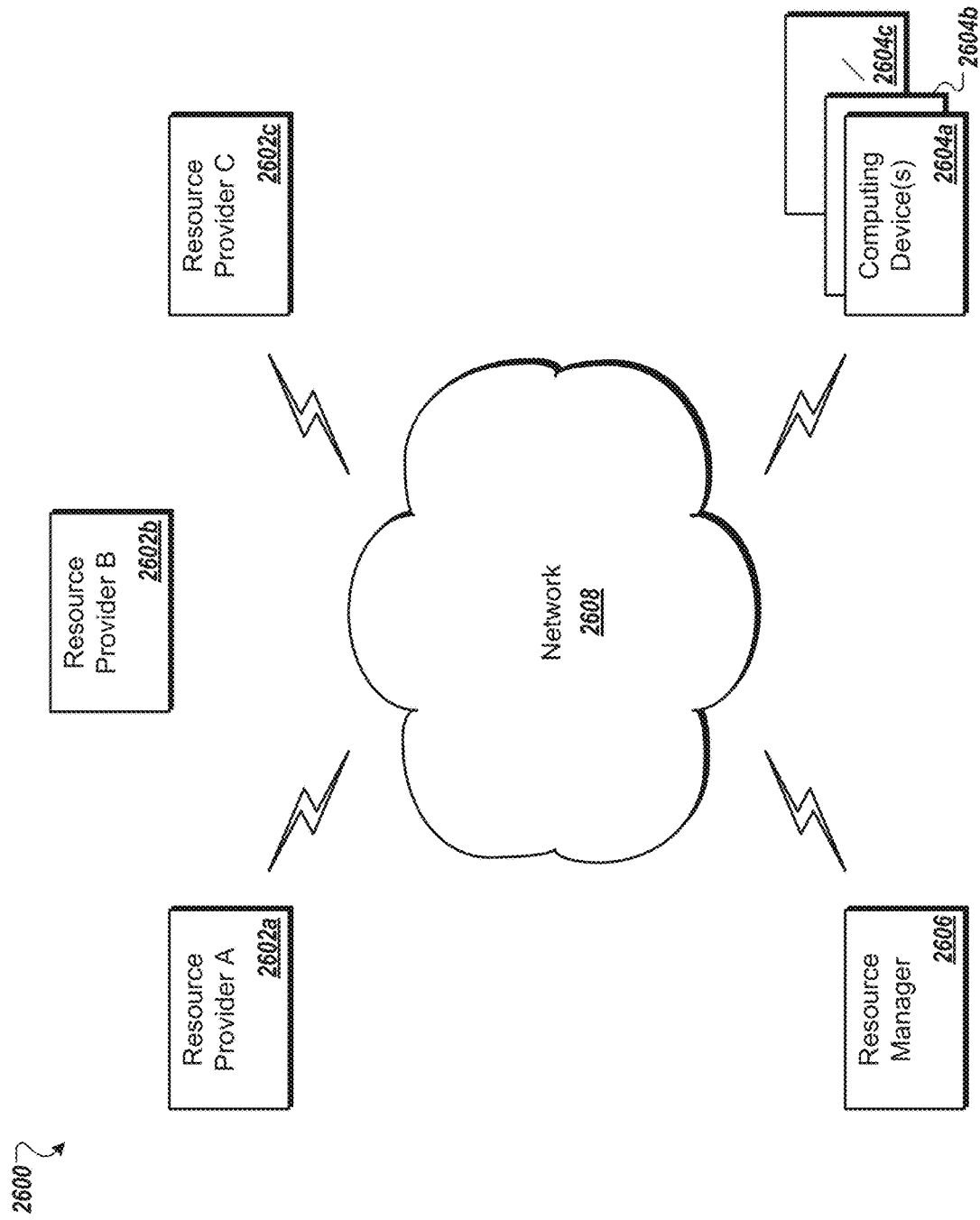
FIG. 26 is a block diagram of an example network environment for use with a surgical robotic system, in accordance with various embodiments of the disclosed technology.

As shown in FIG. 26, an implementation of a network environment 2600 over which various components of a surgical system such as surgical system 260 of FIG. 2 communicate with each other is shown and described. In brief overview, referring now to FIG. 26, a block diagram of an exemplary cloud computing environment 2600 is shown and described. The cloud computing environment 2600 may include one or more resource providers 2602a, 2602b, 2602c (collectively, 2602). Each resource provider 2602 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 2602 may be connected to any other resource provider 2602 in the cloud computing environment 2600. In some implementations, the resource providers 2602 may be connected over a computer network 2608. Each resource provider 2602 may be connected to one or more computing device 2604a, 2604b, 2604c (collectively, 2604), over the computer network 2608.

The cloud computing environment 2600 may include a resource manager 2606. The resource manager 2606 may be connected to the resource providers 2602 and the computing devices 2604 over the computer network 2608. In some implementations, the resource manager 2606 may facilitate the provision of computing resources by one or more resource providers 2602 to one or more computing devices 2604. The resource manager 2606 may receive a request for a computing resource from a particular computing device 2604. The resource manager 2606 may identify one or more resource providers 2602 capable of providing the computing resource requested by the computing device 2604. The resource manager 2606 may select a resource provider 2602 to provide the computing resource. The resource manager 2606 may facilitate a connection between the resource provider 2602 and a particular computing device 2604. In some implementations, the resource manager 2606 may establish a connection between a particular resource provider 2602 and a particular computing device 2604. In some implementations, the resource manager 2606 may redirect a particular computing device 2604 to a particular resource provider 2602 with the requested computing resource.

In view of the structure, functions and apparatus of the systems and methods described here, in some implementations, a system and method for performing robotic assisted surgery are provided. Having described certain implementations of methods and apparatus for performing robotic assisted surgery, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

What is claimed is:

1. An active, non-backdrivable robotic surgical system for performing surgery that permits a surgeon to manually move an end-effector of a robotic arm to a desired position during an operation, the system comprising:
   the robotic arm comprising the end-effector, wherein the robotic arm is active and non-backdrivable, wherein the robot arm includes non-backdrivable gears;
   a force sensor attached to the end-effector of the robotic arm;
   a manipulator attached to the end-effector that may be grasped by a hand of the surgeon, the manipulator comprising one or more user-selectable inputs that allow the surgeon to select between a plurality of modes of movement for the end-effector;
   an activation sensor that detects the presence of the hand of the surgeon on the manipulator, thereby reducing the likelihood that the end-effector is moved unintentionally;
   a tool holder attached to the robotic arm, wherein the tool holder is sized and shaped to hold a first surgical tool; and
   a processor and a non-transitory computer readable medium storing instructions thereon, wherein the instructions, when executed, cause the processor to:
      upon detecting, via the activation sensor, the hand of the surgeon is on the manipulator, determine whether a force applied by the surgeon exceeds a nonzero predetermined minimum threshold required for movement of the end-effector, as detected by the force sensor;
      permit controlled movement of the end effector in response to a force applied by the surgeon when the applied force exceeds the nonzero predetermined minimum threshold; and
      control displacement of the end-effector at a controlled pace in response to the applied force,
   an interlock system separate from the processor that is configured to control the movement of the end-effector, robotic arm, tool holder, and mobile cart,
   wherein the interlock system is configured to mechanically brake any movement of the robotic arm upon detection by the interlock system of an anomaly or problem during the surgical procedure and to resist any movement even in response to external forces to the robotic arm.

2. The system of claim 1, wherein the force sensor is attached to the robotic arm between the end-effector and the robotic arm.

3. The system of claim 1, wherein the manipulator allows movement of the end-effector by the surgeon with at least six degrees of freedom, wherein the six degrees of freedom are three degrees of translations and three degrees of rotations.

4. The system of claim 1, wherein during the operation, movement of the end-effector requires detection, by the activation sensor, of the hand of the surgeon on the manipulator.

5. The system of claim 1, wherein the force sensor is located between the robotic arm and the end-effector, and wherein the force sensor is for measuring forces and/or torques applied by the surgeon to a surgical tool held by the end-effector.

6. The system of claim 1, wherein the controlled movement of the end-effector in response to the force applied to the manipulator by the surgeon comprises controlling an actuator to move the end-effector in a direction corresponding to a direction of application of the force.

7. The system of claim 1, wherein the controlled movement of the end-effector in response to the force applied to the manipulator by the surgeon comprises moving the end-effector at a predetermined measured pace, wherein the predetermined measured pace is a steady, slow velocity.

8. The system of claim 1, comprising:
a tracking detector for real time detection of (i) a position of a surgical tool held by the robotic arm and (ii) a patient's position.

9. The system of claim 8, wherein the patient's position is a position of one or more markers arranged to be placed in spatial relation to one or more vertebrae.

10. The system of claim 1, wherein the instructions, when executed, cause the processor to:
access or generate a virtual representation of a patient's situation;
obtain a real-time (i) position of the first surgical tool held by the robotic arm and/or position of the end-effector and (ii) patient's position from a tracking detector;
determine a projected trajectory based on (a) the position of the first surgical tool held by the robotic arm and (b) the patient's position from the tracking detector; and
display a real-time representation of the projected trajectory of the first surgical tool position in relation to the real-time patient's position, wherein the steps of determining the projected trajectory and displaying the real-time representation of the projected trajectory are automatically updated as the position of the end-effector is changed, thereby providing visual feedback to the surgeon to assist the surgeon in positioning the end-effector at a desired position.

11. The system of claim 10, wherein the desired position is at least one of (i) identified by a surgeon without preoperative planning, (ii) planned with assistance of the robotic surgical system, and (iii) proposed by the robotic surgical system for approval by the surgeon.

12. The system of claim 10, wherein the desired position is planned during the operation.

13. The system of claim 1, wherein the one or more user-selectable inputs comprise one or more buttons.

14. The system of claim 1, wherein the robotic surgical system allows both robotically-assisted and unassisted positioning of the end-effector by the surgeon via the manipulator.

15. The system of claim 1, further comprising a mobile cart that permits the robotic surgical system to be moved in and out of operating room, wherein the mobile cart comprises a plurality of wheels for moving the robotic surgical system and a plurality of rigid legs on which the mobile cart sits to stabilize the robotic surgical system on an operating room floor, wherein either the plurality of wheels or the plurality of rigid legs are retractable.

16. The system of claim 15, wherein the plurality of wheels are retractable and the mobile cart rests on the plurality of rigid legs when the plurality of wheels are retracted.

17. The system of claim 15, wherein the plurality of rigid legs are retractable and the mobile cart rests on the plurality of wheels when the plurality of rigid legs are retracted.

18. The system of claim 1, wherein the end-effector can be positioned with at least four degrees of freedom.

19. The system of claim 1, wherein the first surgical tool is a drill bit tube sized and shaped to receive a drill bit, tap, screwdriver, or implant therethrough.

20. The system of claim 1, wherein the surgery is spinal surgery.

21. The system of claim 1, wherein the tool holder comprises a tool guide attached to the robotic arm and sized and shaped to slidably receive and/or hold the first surgical tool.

22. The system of claim 1, wherein the end-effector is sized and shaped to releasably hold the first surgical tool, allowing the first surgical tool to be removed and replaced with a second surgical tool.

23. The system of claim 1, wherein the instructions further cause the processor to:
upon entry of a user command, control an actuator to translate the end-effector an identified distance in an identified direction and/or to adjust an angle of rotation of the end-effector.

24. An active robotic surgical system for performing surgery that permits a surgeon to manually move an end-effector of a robotic arm to a desired position during an operation, the system comprising:
a force sensor attached to the end-effector of the robotic arm, wherein the robotic arm is active;
a manipulator that may be grasped by a hand of the surgeon to position the end-effector with at least four degrees of freedom, the manipulator comprising one or more user-selectable inputs that allow the surgeon to select between a plurality of modes of movement for the end-effector;
a tool holder attached to the robotic arm;
an activation sensor; and
a processor and a non-transitory computer readable medium storing instructions thereon, wherein the instructions, when executed, cause the processor to:
upon detecting, via the activation sensor, an activation by the surgeon, determine whether a force applied by the surgeon exceeds a nonzero predetermined minimum threshold required for movement of the end-effector, as detected by the force sensor; and
permit controlled movement of the end-effector in response to the force applied to the manipulator by the surgeon when the applied force exceeds the nonzero predetermined minimum threshold,
wherein the surgical robotic system includes an interlock system separate from the processor that is configured to control the movement of the end-effector and robotic arm,
wherein the interlock system is configured to mechanically brake any movement of the robotic arm upon detection by the interlock system of an anomaly or problem during the surgical procedure and to resist any movement even in response to external forces to the robotic arm.

25. The system of claim 1, wherein the manipulator is attached, via an intermediate structure, indirectly to the end-effector.

26. The system of claim 1, further comprising one or more buttons for selection by the surgeon of a type of movement of the end-effector that is permitted when the activation sensor detects the presence of the hand of the surgeon on the manipulator.

* * * * *